United States Patent
Ruella et al.

(10) Patent No.: US 12,227,588 B2
(45) Date of Patent: Feb. 18, 2025

(54) USE OF CD2/5/7 KNOCK-OUT ANTI-CD2/5/7 CHIMERIC ANTIGEN RECEPTOR T CELLS AGAINST T CELL LYMPHOMAS AND LEUKEMIAS

(71) Applicant: THE TRUSTEES OF THE UNIVERSITY OF PENNSYLVANIA, Philadelphia, PA (US)

(72) Inventors: Marco Ruella, Ardmore, PA (US); Saar Gill, Philadelphia, PA (US); Carl H. June, Merion Station, PA (US); Avery D. Posey, Philadelphia, PA (US); Daniel J. Powell, Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 18/620,748

(22) Filed: Mar. 28, 2024

(65) Prior Publication Data
US 2024/0228655 A1    Jul. 11, 2024

Related U.S. Application Data

(63) Continuation of application No. 18/304,843, filed on Apr. 21, 2023, which is a continuation of application No. 17/416,365, filed as application No. PCT/US2019/067613 on Dec. 19, 2019, now Pat. No. 11,673,964.

(60) Provisional application No. 62/782,131, filed on Dec. 19, 2018.

(51) Int. Cl.
| | |
|---|---|
| C07K 16/28 | (2006.01) |
| A61K 35/17 | (2015.01) |
| A61K 38/00 | (2006.01) |
| A61K 39/00 | (2006.01) |
| A61P 35/00 | (2006.01) |
| A61P 35/02 | (2006.01) |
| C07K 14/47 | (2006.01) |
| C07K 14/705 | (2006.01) |
| C07K 14/725 | (2006.01) |
| C12N 5/0783 | (2010.01) |

(52) U.S. Cl.
CPC ...... *C07K 16/2896* (2013.01); *A61K 39/4611* (2023.05); *A61K 39/4631* (2023.05); *A61K 39/464429* (2023.05); *A61P 35/00* (2018.01); *A61P 35/02* (2018.01); *C07K 14/70507* (2013.01); *C07K 14/7051* (2013.01); *C07K 14/70578* (2013.01); *C07K 14/70596* (2013.01); *C07K 16/2803* (2013.01); *C07K 16/2806* (2013.01); *C12N 5/0636* (2013.01); *A61K 38/00* (2013.01); *A61K 2039/505* (2013.01); *A61K 2239/38* (2023.05); *A61K 2239/48* (2023.05); *C07K 14/4748* (2013.01); *C07K 2317/565* (2013.01); *C07K 2317/622* (2013.01); *C07K 2317/92* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | |
|---|---|---|
| 5,951,983 A | 9/1999 | Bazin |
| 2015/0218640 A1 | 8/2015 | Brandon |
| 2018/0066034 A1 | 3/2018 | Ma |
| 2018/0346876 A1 | 12/2018 | Xiao |

FOREIGN PATENT DOCUMENTS

| | | |
|---|---|---|
| WO | 2010022737 A1 | 3/2010 |
| WO | 2017112877 A1 | 6/2017 |
| WO | 2017172981 A2 | 10/2017 |
| WO | 2017189959 | 11/2017 |
| WO | 2018102795 A2 | 6/2018 |
| WO | 2018178378 | 10/2018 |

OTHER PUBLICATIONS

International Search Report and Written Opinion issued in App. No. PCT/US2019/067613, mailing date Mar. 31, 2020, 16 pages.
Klitgaard, Josephine L., et al., "Combination of two anti-CD5 monoclonal antibodies synergistically induces complement-dependent cytotoxicity of chronic lymphocytic leukaemia cells", British Journal of Haematology, 2013, 163, 182-193.
Mamonkin, Maksim et al., "A T-cell-directed chimeric antigen receptor for the selective treatment of T-cell malignancies", Blood, 2015, 126(8):983-992.
Raikur et al. (Oncoimmunology. 2018 [published online Dec. 26, 2017], vol. 7, No. 3, e1407898 (14 pages) https://loi.org/10.1080/2162402X.2017.1407898). (Year: 2018).
Padilla, Olga, et al., "Genomic organization of the human CD5 gene", Immunogenetics, 2000, 51, 993-1001.
Zhenyu, Dai, et al., "The rational development of CD5-targeting biepitopic CARs with fully human heavy-chain-only antigen recognition domains", Molecular Therapy, 2021, 29(9):2707-2722.
European Search Report issued in App. No. EP19898610.1, mailing date Sep. 16, 2022, 13 pages.

*Primary Examiner* — Robert M Kelly
(74) *Attorney, Agent, or Firm* — Saul Ewing LLP; Kathryn Doyle

(57) ABSTRACT

The present invention includes compositions and methods for treating T cell lymphomas and leukemias. In certain aspects, the compositions and methods include CAR T cells targeting CD2, CD5, or CD7 and modified cells wherein CD2, CD5, or CD7 has been knocked-out.

22 Claims, 27 Drawing Sheets
Specification includes a Sequence Listing.

Anti-CD2 CARs
1. pTRPE MEDI507 CAR2(H2L)-BBz (C3028)
2. pTRPE MEDI507 CAR2(L2H)-BBz (C3043)
3. pTRPE OKT11 CAR2(H2L)-BBz (C3029)
4. pTRPE OKT11 CAR2(L2H)-BBz (C3030)
5. pTRPE T11-2 CAR2(H2L)-BBz (C3031)
6. pTRPE TS2_18.1.1 CAR2(H2L)-BBz (C3032)
7. pTRPE TS2_18.1.1 CAR2(L2H)-BBz (C3033)

Anti-CD5 CARs
1. pTRPE-17CAR5(H2L)-CD8H-BBz (C3054)
2. pTRPE-17CAR5(L2H)-CD8H-BBz (C3045)
3. pTRPE-34CAR5(H2L)-CD8H-BBz (C3052)
4. pTRPE-34CAR5(L2H)-CD8H-BBz (C3053)
5. pTRPE-9CAR5(H2L)-CD8H-BBz (C3048)
6. pTRPE-9CAR5(L2H)-CD8H-BBz (C3049)

USE OF CD2/5/7 KNOCK-OUT ANTI-CD2/5/7 CHIMERIC ANTIGEN RECEPTOR T CELLS AGAINST T CELL LYMPHOMAS AND LEUKEMIAS

CROSS-REFERENCE TO RELATED APPLICATION

The present application is a continuation of U.S. patent application Ser. No. 18/304,843, filed Apr. 21, 2023, which is a continuation of U.S. patent application Ser. No. 17/416,365, filed Jun. 18, 2021, now U.S. Pat. No. 11,673,964, which is a national stage application under 35 U.S.C. § 371 of International Application No. PCT/US2019/067613, filed Dec. 19, 2019, which claims priority under 35 U.S.C. § 119(e) to U.S. Provisional Patent Application No. 62/782,131, filed Dec. 19, 2018, which are hereby incorporated by reference in their entireties herein.

REFERENCE TO AN ELECTRONIC SEQUENCE LISTING

The XML file named "046483-7224US2.xml" created on Apr. 13, 2023, comprising 147,892 bytes, is incorporated herein by reference in its entirety.

BACKGROUND OF THE INVENTION

T cell lymphomas and leukemias are aggressive neoplasms derived from T cell progenitors or differentiated T cells. Mature or peripheral T cell lymphomas account for 10%-15% of all non-Hodgkin's lymphomas, or ~7,000-10,000 cases in the U.S. per year. T cell lymphomas and leukemias have poor prognoses and there are few available treatments. Chimeric antigen receptor T cell (CART) therapy has demonstrated efficacy for B cell neoplasms, but extending the success of CAR T cells to T cell malignancies is problematic because most target antigens are shared between normal and malignant cells, leading to CAR T cell fratricide.

A need exists for compositions and methods for treating T cell lymphomas and leukemias as well as methods for eliminating CAR T cell fratricide. The present invention addresses this need.

SUMMARY OF THE INVENTION

As described herein, the present invention relates to compositions and methods utilizing CAR T cells targeting CD2, CD5, or CD7 and modified cells wherein CD2, CD5, or CD7 has been knocked-out.

In one aspect, the invention includes a method of treating cancer in a subject in need thereof. The method comprises administering to the subject a first modified cell comprising a chimeric antigen receptor (CAR), wherein the CAR comprises an antigen binding domain, a transmembrane domain, and an intracellular domain, and administering to the subject a second modified cell wherein the endogenous CD5 gene has been knocked-out.

In another aspect, the invention includes a method of treating cancer in a subject in need thereof. The method comprises administering to the subject a first modified cell comprising a chimeric antigen receptor (CAR), wherein the CAR comprises an antigen binding domain capable of binding CD2, a transmembrane domain, and an intracellular domain, and administering to the subject a second modified cell wherein the endogenous CD2 gene has been knocked-out.

In yet another aspect, the invention includes a method of treating cancer in a subject in need thereof. The method comprises administering to the subject a first modified cell comprising a CAR, wherein the CAR comprises an antigen binding domain capable of binding CD5, a transmembrane domain, and an intracellular domain, and administering to the subject a second modified cell wherein the endogenous CD5 gene has been knocked-out.

In still another aspect, the invention includes a method of treating cancer in a subject in need thereof comprising administering to the subject a first modified cell comprising a CAR, wherein the CAR comprises an antigen binding domain capable of binding CD7, a transmembrane domain, and an intracellular domain, and administering to the subject a second modified cell wherein the endogenous CD7 gene has been knocked-out.

Another aspect of the invention includes a nucleic acid comprising a CAR, wherein the CAR comprises an antigen binding domain capable of binding CD2, a transmembrane domain, and an intracellular domain.

Yet another aspect of the invention includes a nucleic acid comprising a CAR, wherein the CAR comprises an antigen binding domain capable of binding CD5, a transmembrane domain, and an intracellular domain.

Still another aspect of the invention includes a vector comprising any of the nucleic acids disclosed herein.

In another aspect, the invention includes a cell comprising any of the nucleic acids disclosed herein or any of the vectors disclosed herein.

In yet another aspect, the invention includes a composition comprising a first modified cell comprising a chimeric antigen receptor (CAR), wherein the CAR comprises an antigen binding domain that targets CD2, a transmembrane domain, and an intracellular domain, and a second modified cell wherein the endogenous CD2 gene has been knocked-out.

In still another aspect, the invention includes a composition comprising a first modified cell comprising a chimeric antigen receptor (CAR), wherein the CAR comprises an antigen binding domain that targets CD5, a transmembrane domain, and an intracellular domain, and a second modified cell wherein the endogenous CD5 gene has been knocked-out.

In another aspect, the invention includes a composition comprising a first modified cell comprising a chimeric antigen receptor (CAR), wherein the CAR comprises an antigen binding domain that targets CD7, a transmembrane domain, and an intracellular domain, and a second modified cell wherein the endogenous CD7 gene has been knocked-out.

Another aspect of the invention includes a composition comprising a first modified cell comprising a chimeric antigen receptor (CAR), wherein the CAR comprises an antigen binding domain, a transmembrane domain, and an intracellular domain, and a second modified cell wherein the endogenous CD5 gene has been knocked-out.

In various embodiments of the above aspects or any other aspect of the invention delineated herein, the endogenous gene is knocked-out using a CRISPR method. In certain embodiments, the CRISPR method is a CRISPR/Cas9 method. In certain embodiments, the CRISPR/Cas9 method utilizes an sgRNA comprising the nucleotide sequence of SEQ ID NO: 23. In certain embodiments, the CRISPR/Cas9 method utilizes an sgRNA comprising the nucleotide sequence selected from the group consisting of SEQ ID NO: 22-24.

In certain embodiments, the antigen binding domain of the CAR is capable of binding an antigen selected from the group consisting of CD5, CD19, CD2, CD7, a tumor-specific antigen (TSA), a tumor associated antigen (TAA), a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin, telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, mesothelin, MART-1/MelanA (MART-I), gp100 (Pmel 17), tyrosinase, TRP-1, TRP-2, MAGE-1, MAGE-3, BAGE, GAGE-1, GAGE-2, p15, Ras, BCR-ABL, E2A-PRL, H4-RET, IGH-IGK, MYL-RAR, EBVA, HPV antigen E6, HPV antigen E7, TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In certain embodiments, the antigen binding domain of the CAR comprises a complementarity determining region (CDR) comprising the amino acid sequence selected from the group consisting of SEQ ID NOs: 31-36, 43-48, 53-58, 65-70, 83-88, and 95-100. In certain embodiments, the antigen binding domain of the CAR comprises a complementarity determining region (CDR) comprising the amino acid sequence selected from the group consisting of SEQ ID NOs: 31-36, 43-48, 53-58, and 65-70. In certain embodiments, the antigen binding domain of the CAR comprises a complementarity determining region (CDR) comprising an amino acid sequence selected from the group consisting of SEQ ID NOs: 83-88 and 95-100.

In certain embodiments, the antigen binding domain of the CAR comprises a heavy chain variable region comprising an amino acid sequence selected from the group consisting of SEQ ID NOs: 29, 41, 51, 63, 75, 81, and 93. In certain embodiments, the antigen binding domain of the CAR comprises a light chain variable region comprising an amino acid sequence selected from the group consisting of SEQ ID NOs: 30, 42, 52, 64, 76, 82, and 94.

In certain embodiments, the antigen binding domain of the CAR comprises a heavy chain variable region comprising the amino acid sequence selected from the group consisting of SEQ ID NOs: 29, 41, 51, and 63. In certain embodiments, the antigen binding domain of the CAR comprises a light chain variable region comprising the amino acid sequence selected from the group consisting of SEQ ID NOs: 30, 42, 52, and 64.

In certain embodiments, the antigen binding domain of the CAR comprises a heavy chain variable region comprising the amino acid sequence selected from the group consisting of SEQ ID NOs: 75, 81, and 93. In certain embodiments, the antigen binding domain of the CAR comprises a light chain variable region comprising the amino acid sequence selected from the group consisting of SEQ ID NOs: 76, 82, and 94.

In certain embodiments, the antigen binding domain of the CAR comprises an scFv comprising an amino acid sequence selected from the group consisting of SEQ ID NOs: 27, 28, 39, 40, 50, 61, 62, 73, 74, 79, 80, 91, and 92. In certain embodiments, the antigen binding domain of the CAR comprises an scFv comprising the amino acid sequence selected from the group consisting of SEQ ID NOs: 27, 28, 39, 40, 50, 61, and 62. In certain embodiments, the antigen binding domain of the CAR comprises an scFv comprising the amino acid sequence selected from the group consisting of SEQ ID NOs: 73, 74, 79, 80, 91, and 92.

In certain embodiments, the CAR comprises an amino acid sequence selected from the group consisting of SEQ ID NOs: 25, 26, 37, 38, 49, 59, 60, 71, 72, 77, 78, 89, and 90. In certain embodiments, the CAR comprises an amino acid sequence selected from the group consisting of SEQ ID NOs: 25, 26, 37, 38, 49, 59, and 60. In certain embodiments, the CAR comprises an amino acid sequence selected from the group consisting of SEQ ID NOs: 71, 72, 77, 78, 89, and 90.

In certain embodiments, the CAR is encoded by a nucleic acid sequence selected from the group consisting of SEQ ID NOs: 1-13. In certain embodiments, the CAR is encoded by a nucleic acid sequence selected from the group consisting of SEQ ID NOs: 1-7. In certain embodiments, the CAR is encoded by a nucleic acid sequence selected from the group consisting of SEQ ID NOs: 8-13.

In certain embodiments, the CAR further comprises a suicide gene. In certain embodiments, the suicide gene is iCaspase9.

In certain embodiments, the first and or second modified cell is a T cell.

In certain embodiments, the cancer comprises a T cell lymphoma or a T cell leukemia. In certain embodiments, the cancer is selected from the group consisting of acute myeloid leukemia (AML), T-cell acute lymphoblastic leukemia (T-ALL), acute lymphoblastic leukemia (ALL), and chronic lymphocytic leukemia (CLL).

In certain embodiments, the composition comprises a pharmaceutically acceptable carrier.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

NHL (or T-ALL) CART (either CART2/5/7, e.g. CART2) and CD2/5/7 knocked out normal T cells. The CART will destroy tumor cells but will also kill normal T cells. The infusion of CD2/5/7 (or other tumor target) KO normal T cells will provide CART-resistant T cell immunity until the CART cells are depleted.

Figure 4:
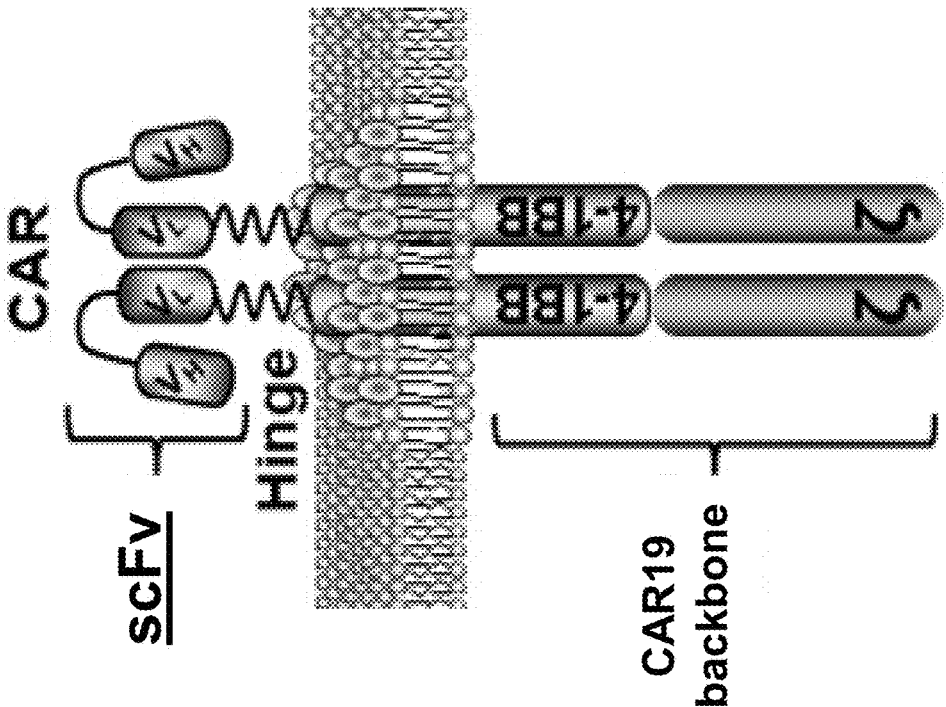

FIG. 4 illustrates anti-CD2 and anti-CD5 CAR constructs used herein. All constructs have a lentiviral pTRPE 4-1BB CD3zeta backbone.

Figure 5:
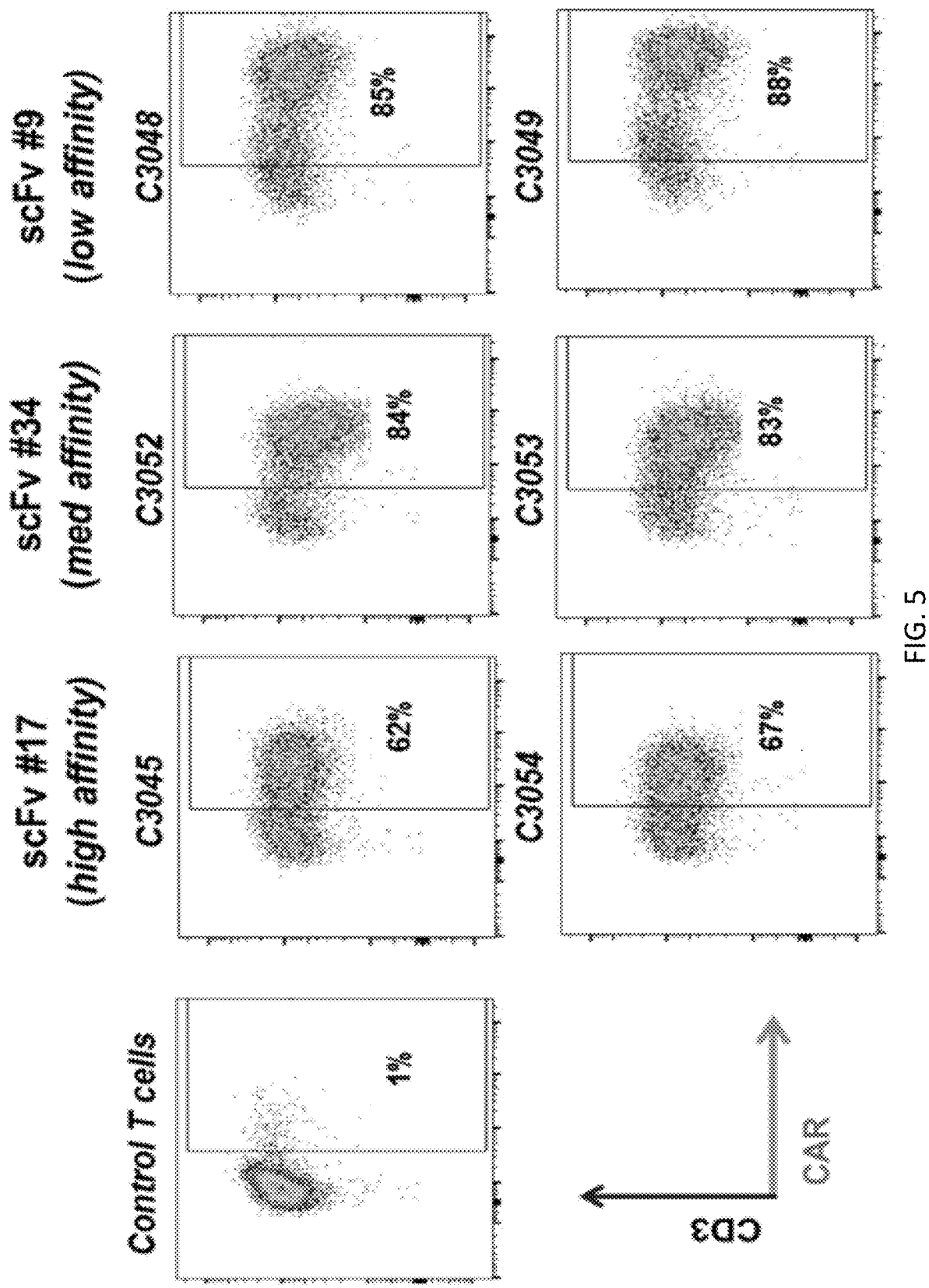

FIG. 5 illustrates CART transduction efficiency in T cells. Six different CAR5 constructs were generated using single-chain variable fragments (scFvs) with high (#17), medium (#34) and low (#9) affinity. T cells were activated with anti-CD3/CD28 beads (Dynabeads) and 24 hours later lentiviral vectors were added at a MOI of 3. Dynabeads were removed at day 6. CART cells were frozen when the mean volume was below 350 fl. CAR expression (goat-anti-mouse Fab antibody) was tested at day 6.

Figure 6:
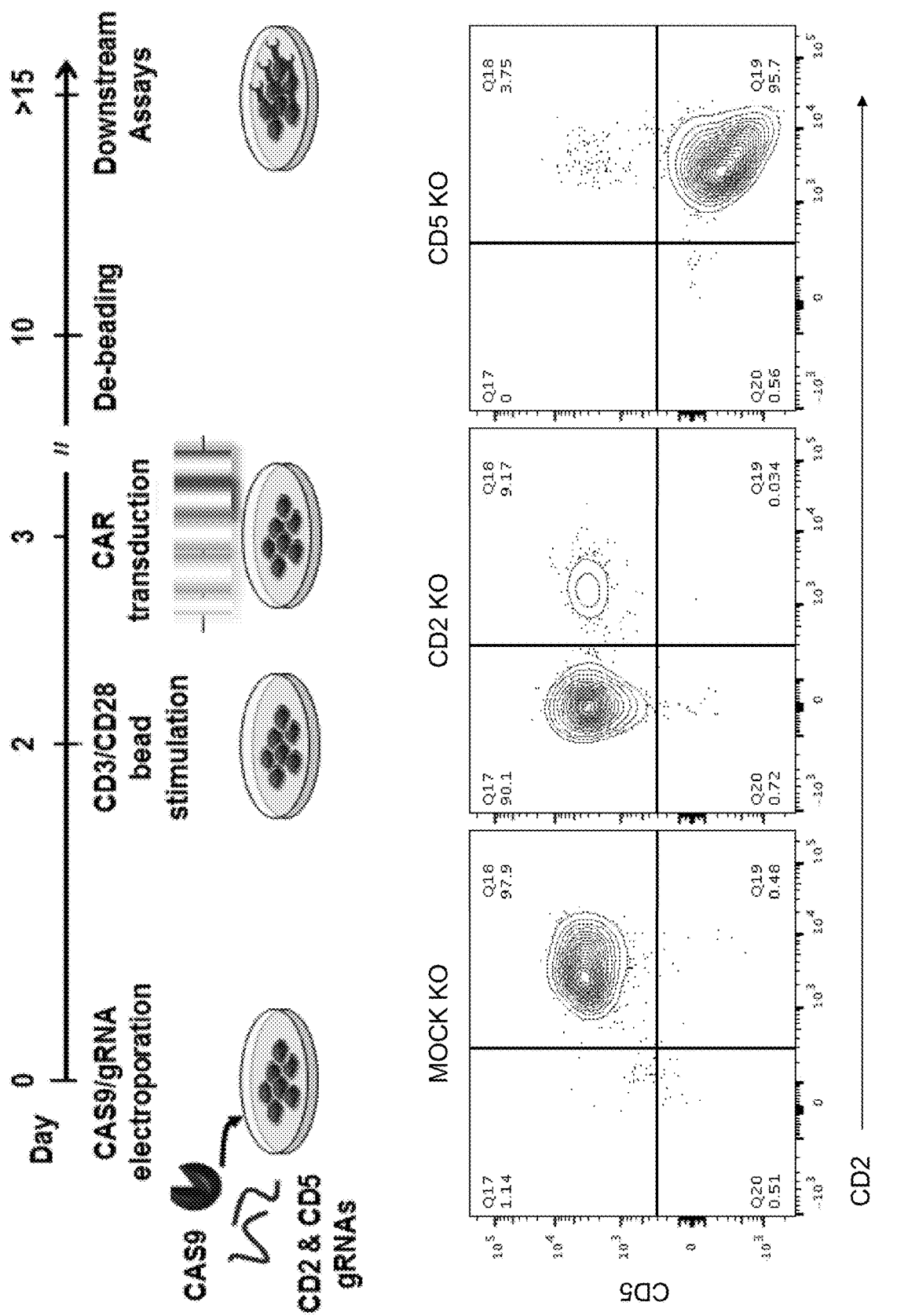

FIG. 6 illustrates the CD5 (or CD2, or CD7) KO manufacturing process and CRISPR-Cas9 KO efficiency.

Figure 7:
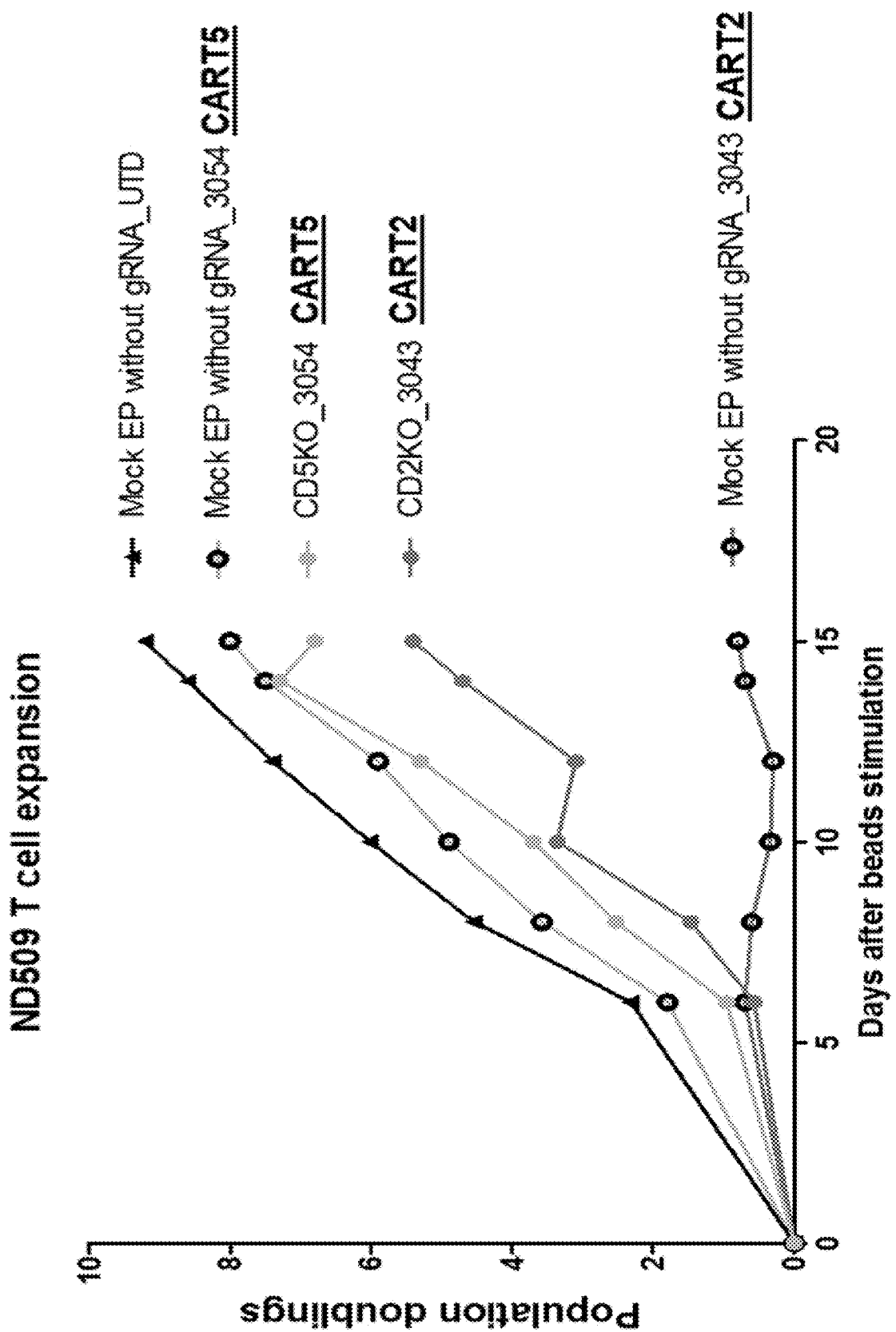

FIG. 7 illustrates expansion curves of several CART groups. Without CD2 KO CART2 cells would not expand. With KO CART2 and CART5 reach about 5-8 population doublings.

Figure 8:
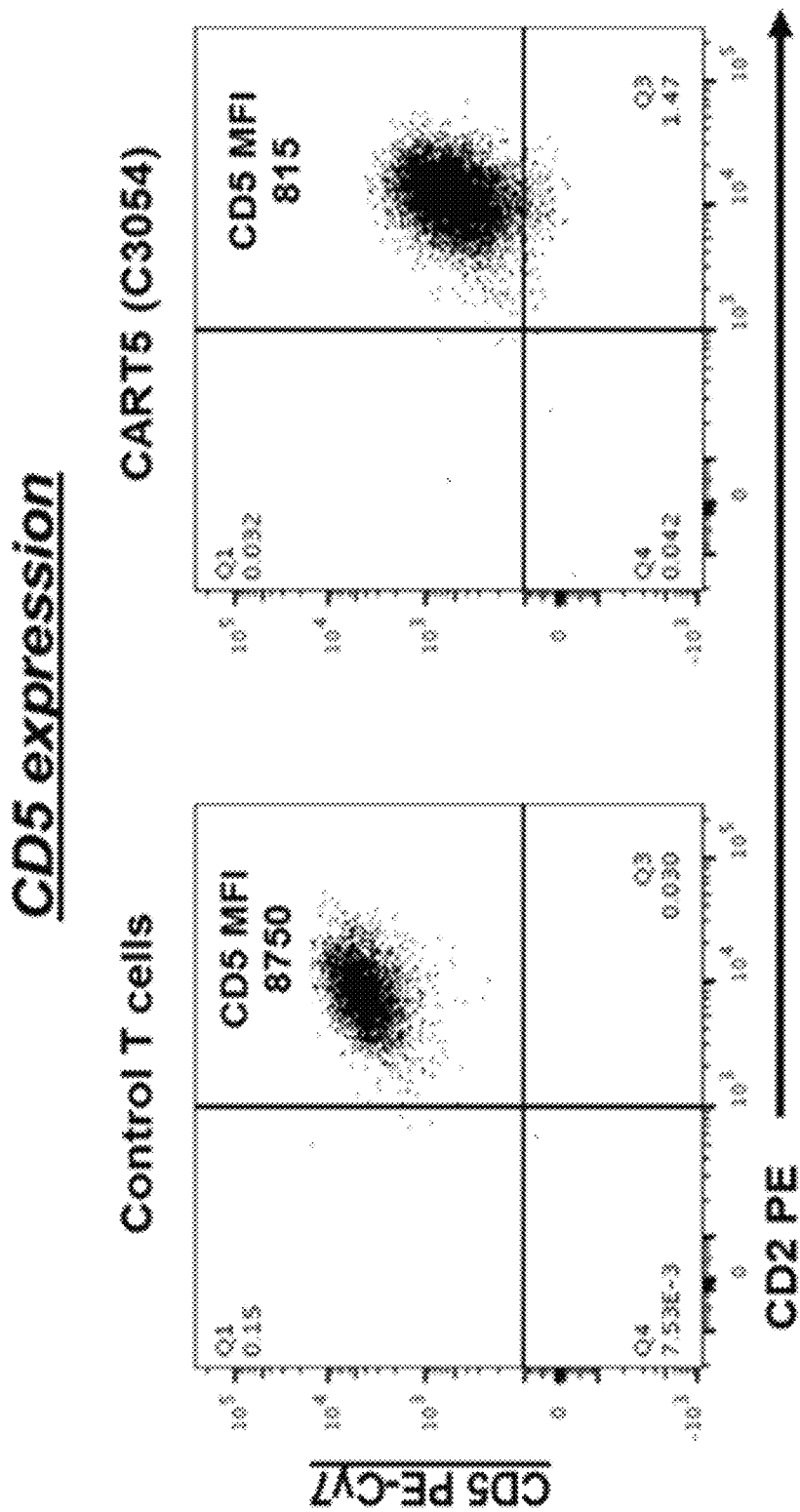

FIG. 8 illustrates the finding that without CRISPR-Cas9 KO of CD5, the CD5 mean fluorescence intensity (MFI) was 10 folds less in CART5 as compared to control T cells, while there was no change in another pan T-cell marker such as CD2.

Figure 9:
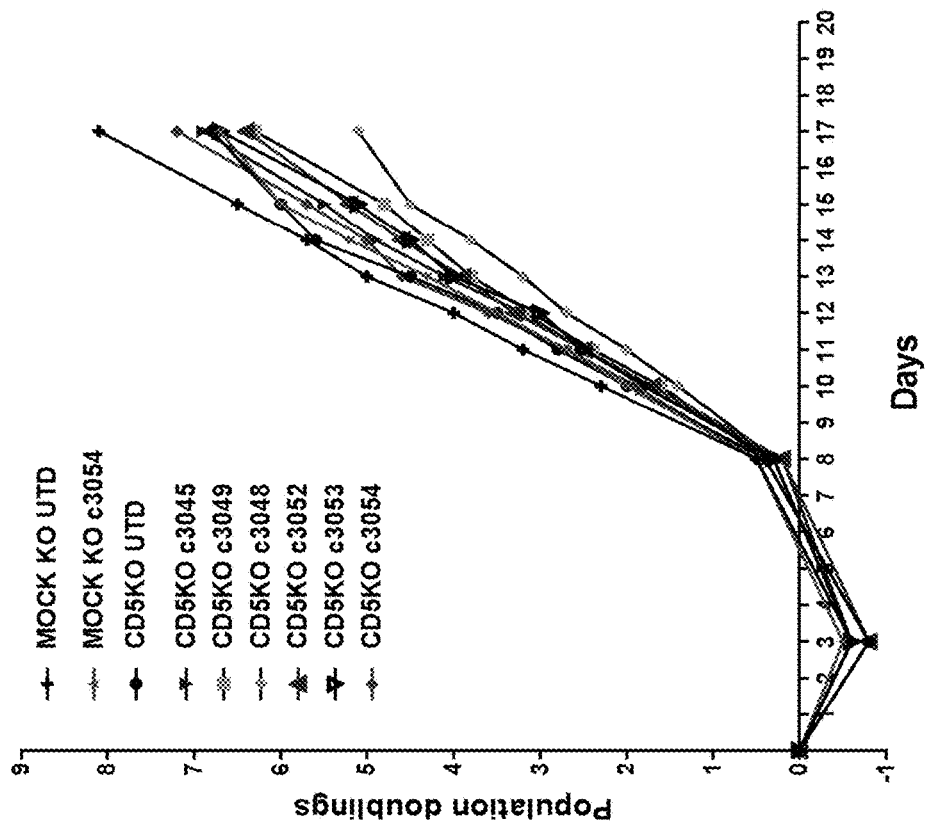
Figure 9:
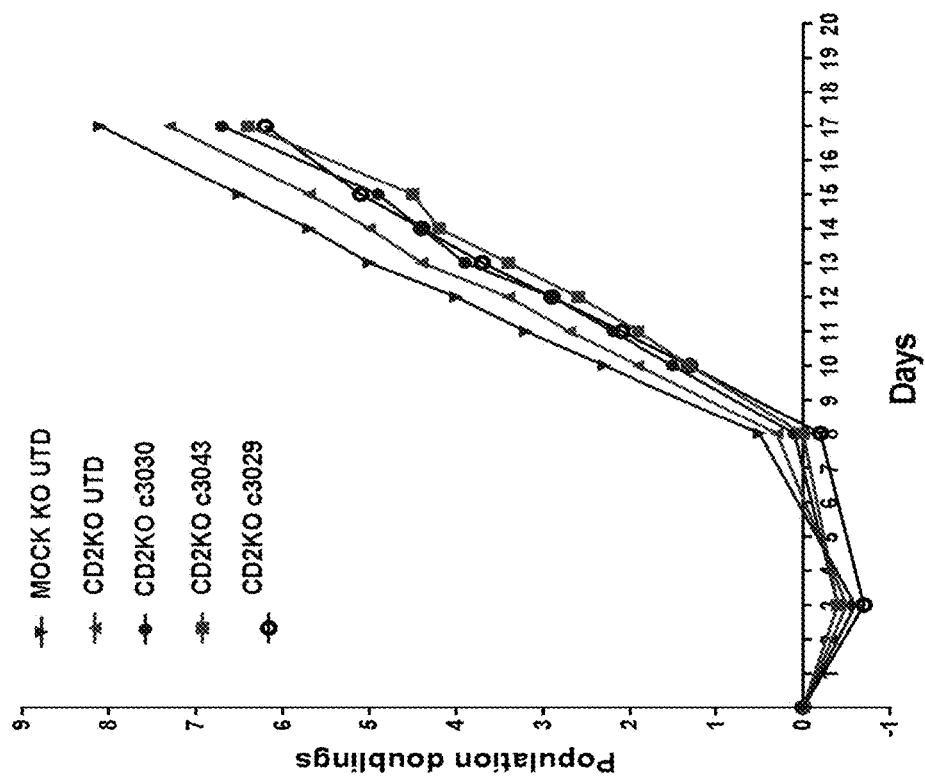

FIG. 9 illustrates CART2 and CART5 expansion curves. T cell concentration was measured using Coulter Counter.

Figure 10:
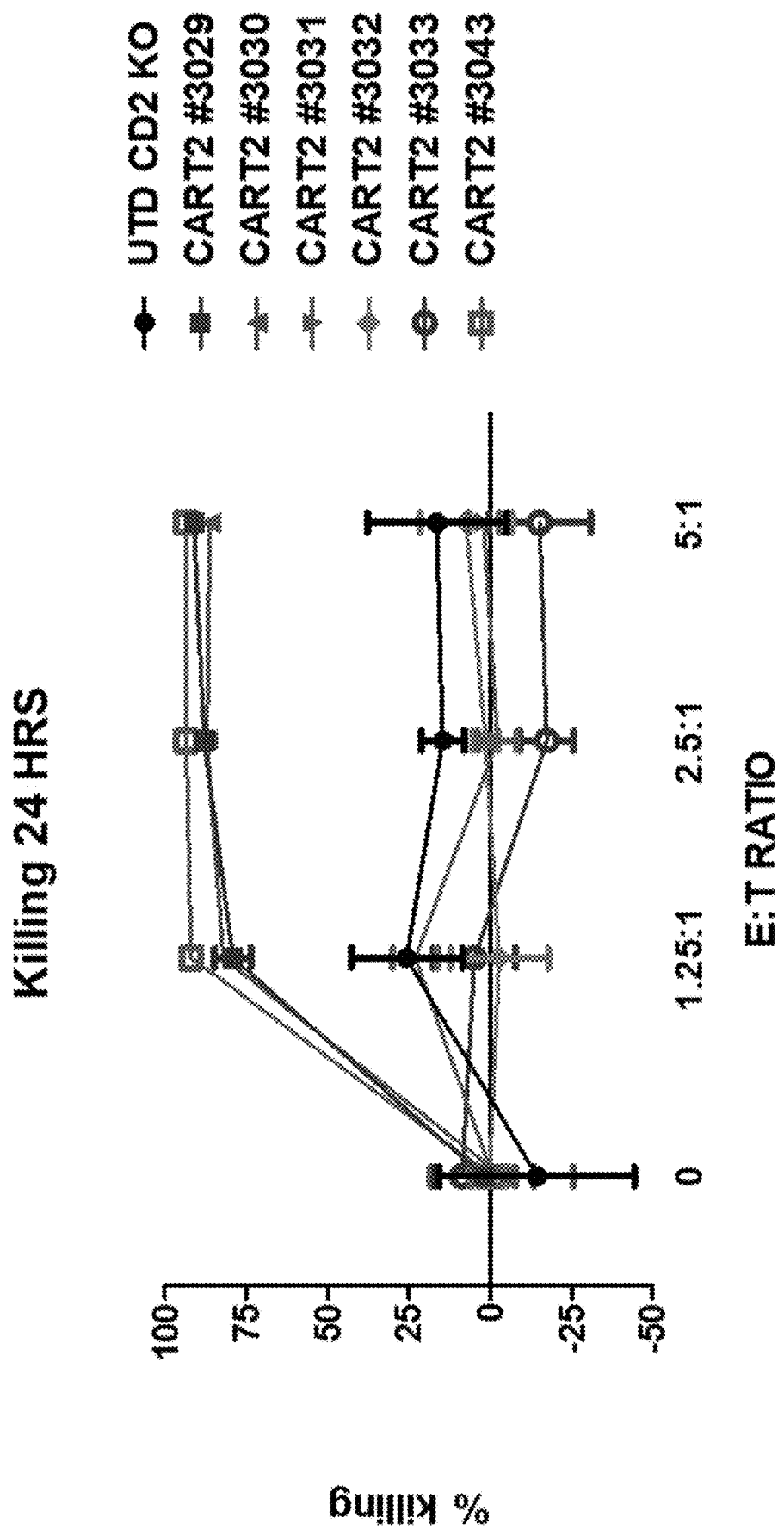

FIG. 10 illustrates results from an experiment wherein six different CAR2 constructs were challenged in vitro by co-culturing them with luciferase+ Jurkat cells (T-cell leukemia cell line). At 24 hours, total killing was measured as relative reduction in luminescence. Only C3029, C3030 and C3043 showed anti-tumor effects.

Figure 11:
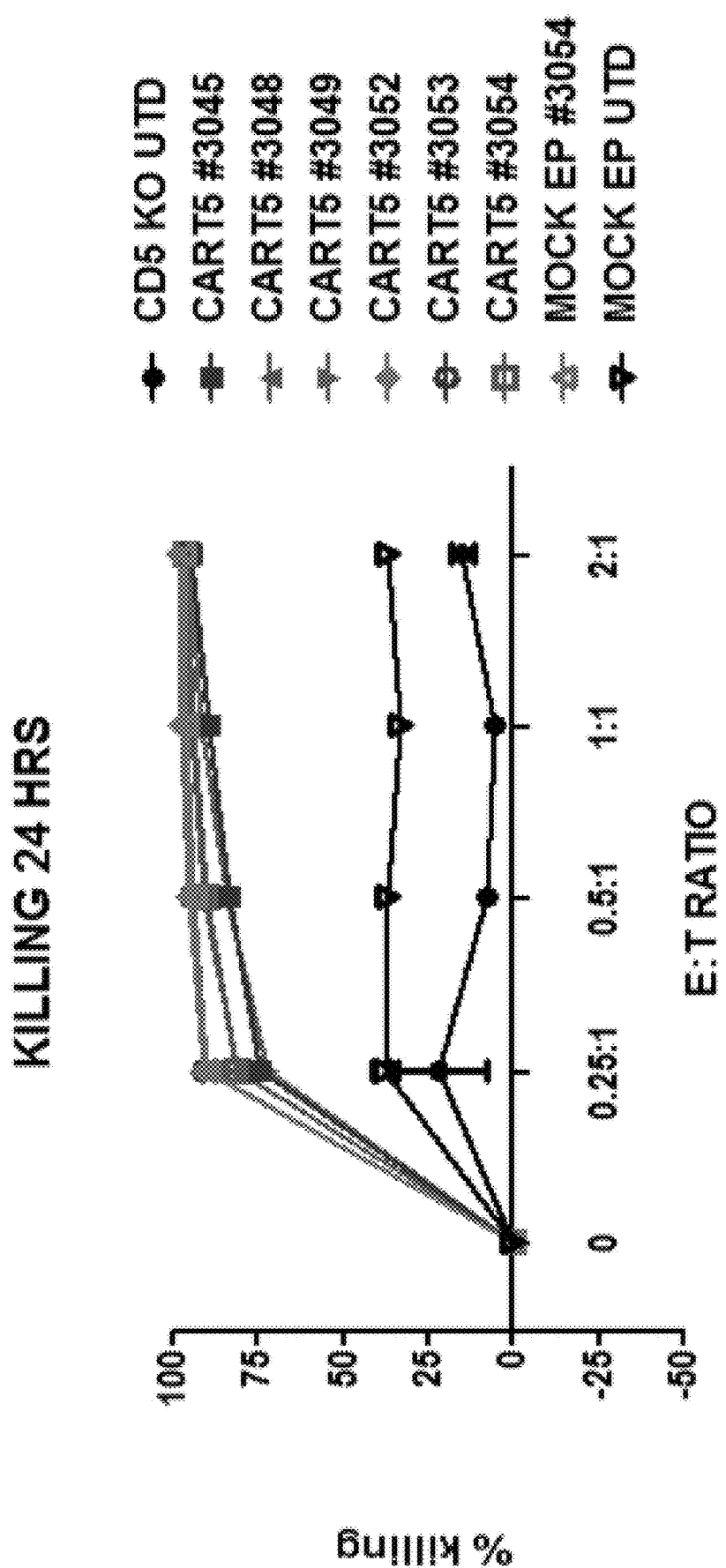

FIG. 11 illustrates results from an experiment wherein six different CAR5 constructs were challenged in vitro by co-culturing them with luciferase+ Jurkat cells (T-cell leukemia cell line). At 24 hours, total killing was measured as relative reduction in luminescence. All the CAR5 constructs showed similar anti-tumor effects.

Figure 12:
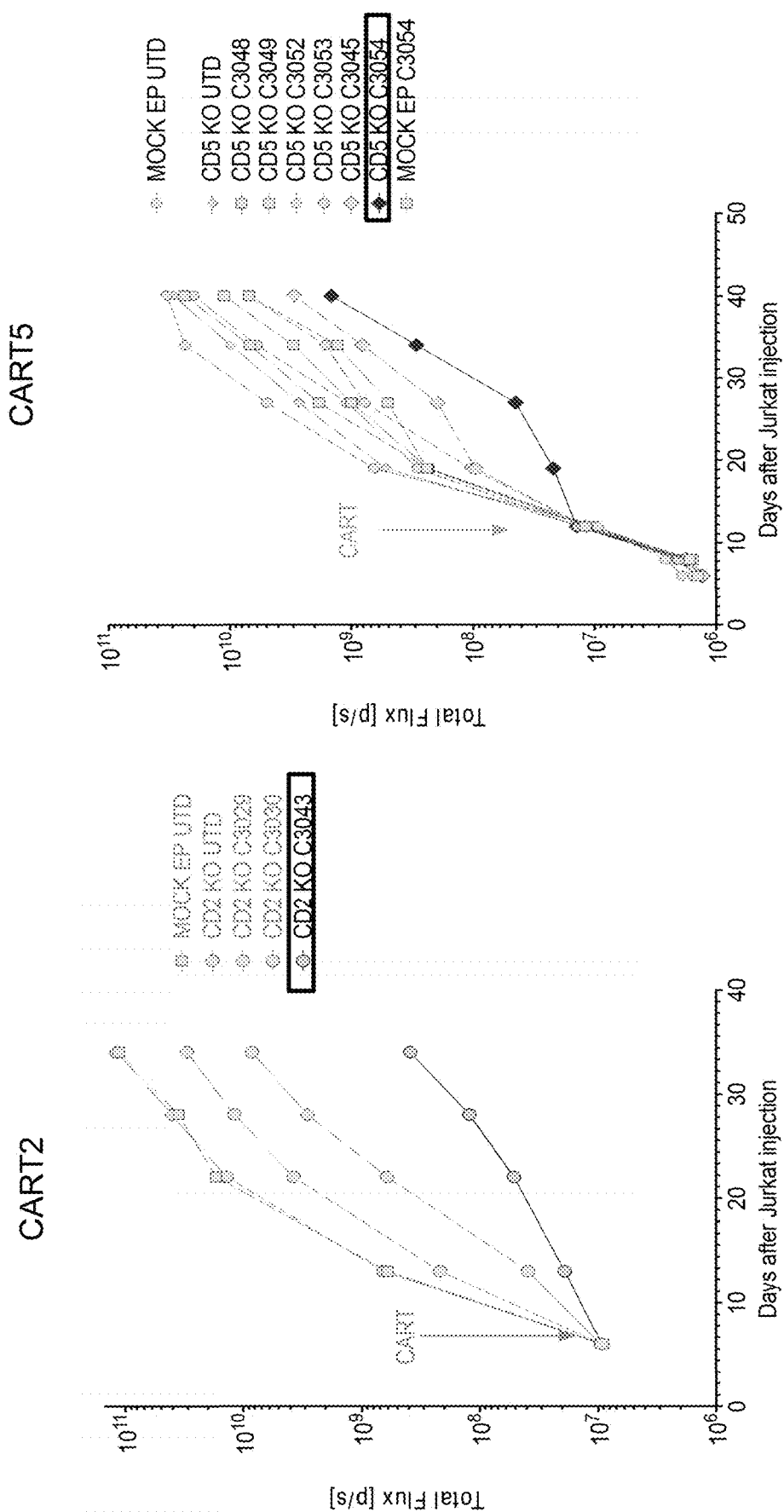

FIG. 12 illustrates the in vivo efficacy of CART2 and CART5. NSG mice were engrafted with Luciferase+ Jurkat cells and mice were randomized to receive control T cells or CART2 or CART5 ($1\times10^6$) at day 7. Mice were imaged weekly using the IVIS Xenogen Spectrum and analyzed with LivingImage software. CART2 C3043 and CART5 C3054 were the most effective.

Figure 13:
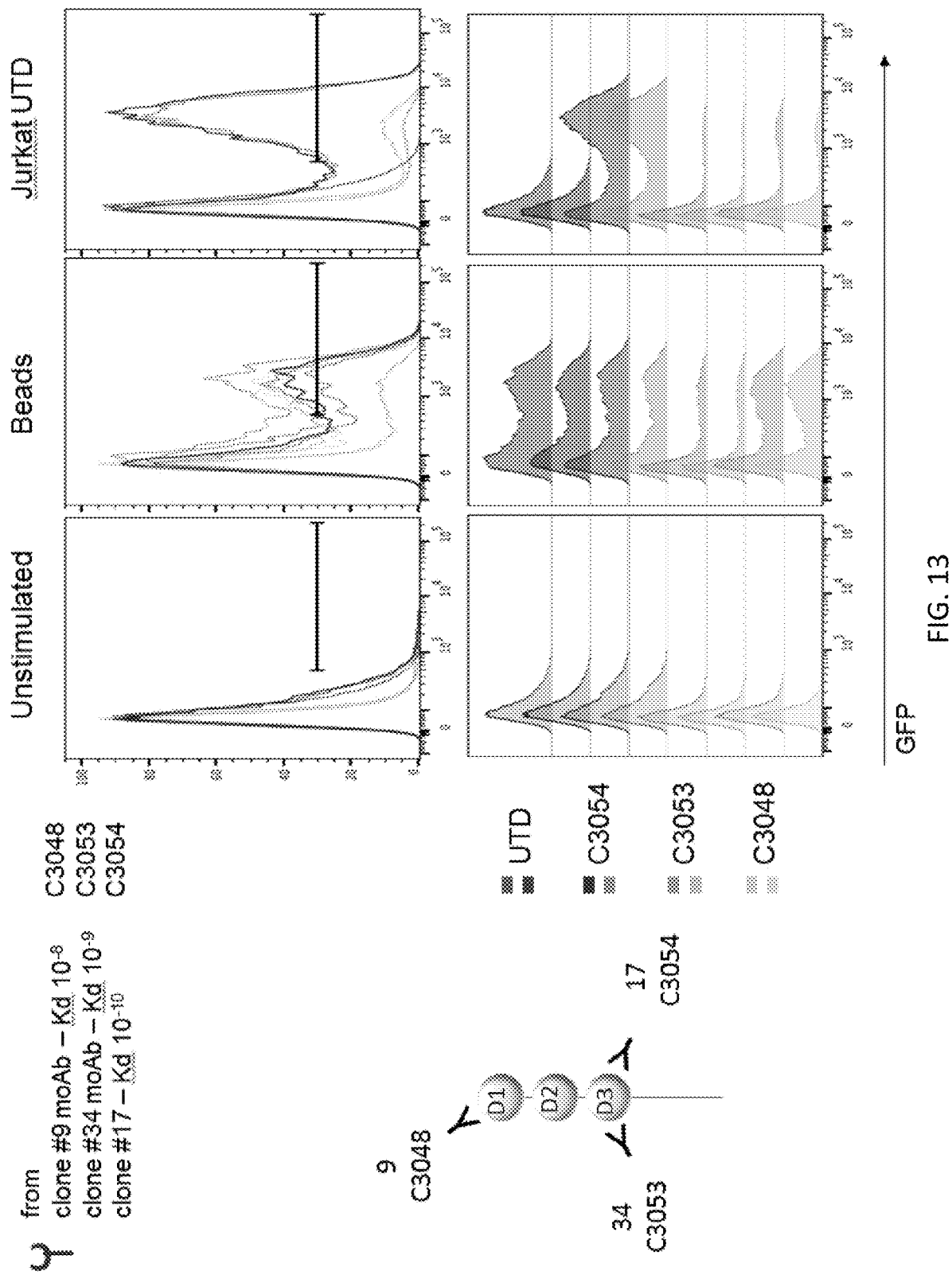

FIG. 13 illustrates results from an experiment wherein Jurkat cells were transduced with different CAR5 constructs (targeted epitope and affinity shown to the left) and with a GFP-NFAT reporter then co-cultured with CD5+ tumor cells (or controls) for 24 hours. The lead CART5 (C3054) showed increased NFAT activation.

Figure 14:
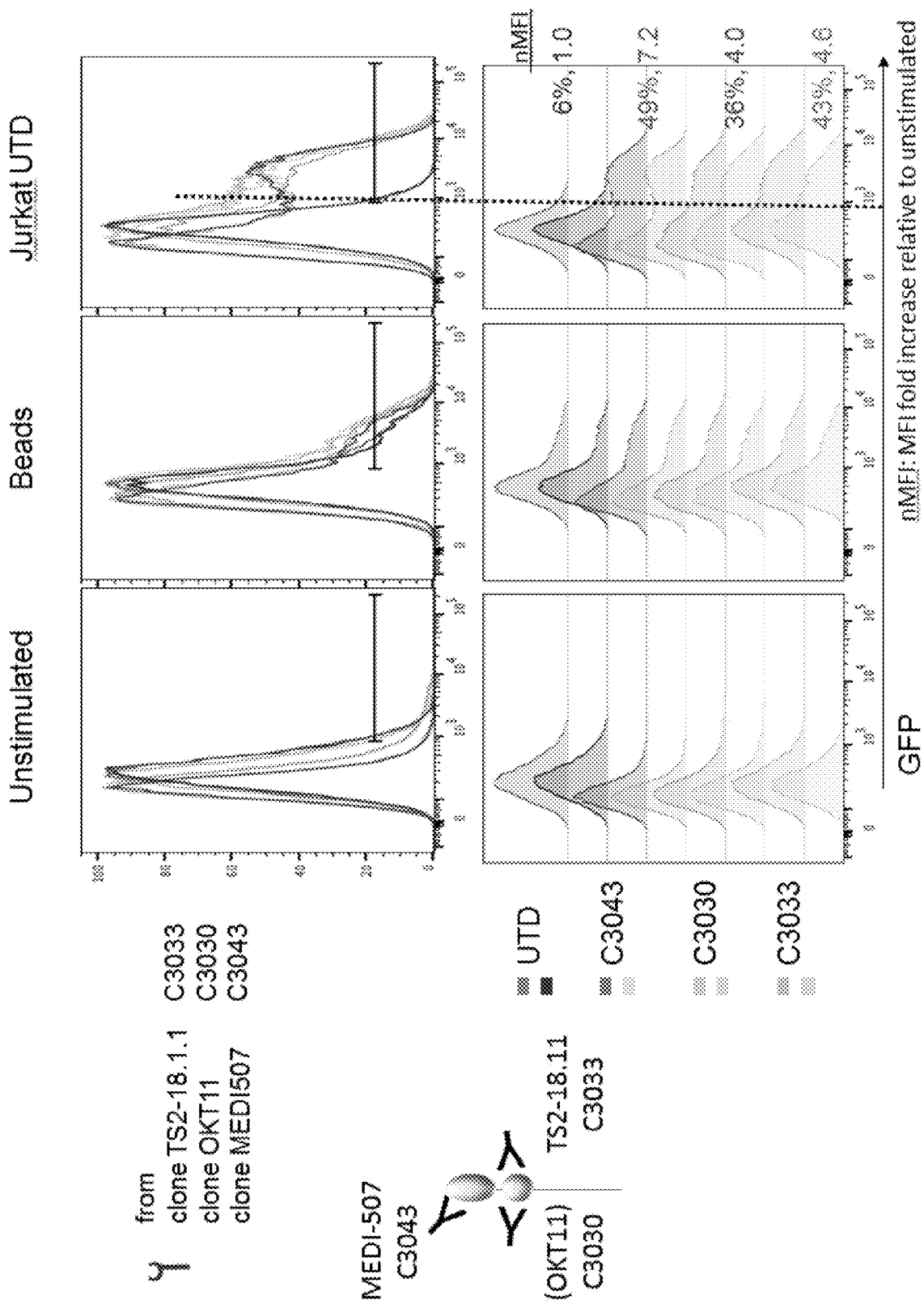

FIG. 14 illustrates results from an experiment wherein Jurkat cells were transduced with the different CAR2 constructs and with a GFP-NFAT reporter then co-cultured with CD2+ tumor cells (or controls) for 24 hours. The lead CART2 (C3043) showed increased NFAT activation.

Figure 15:
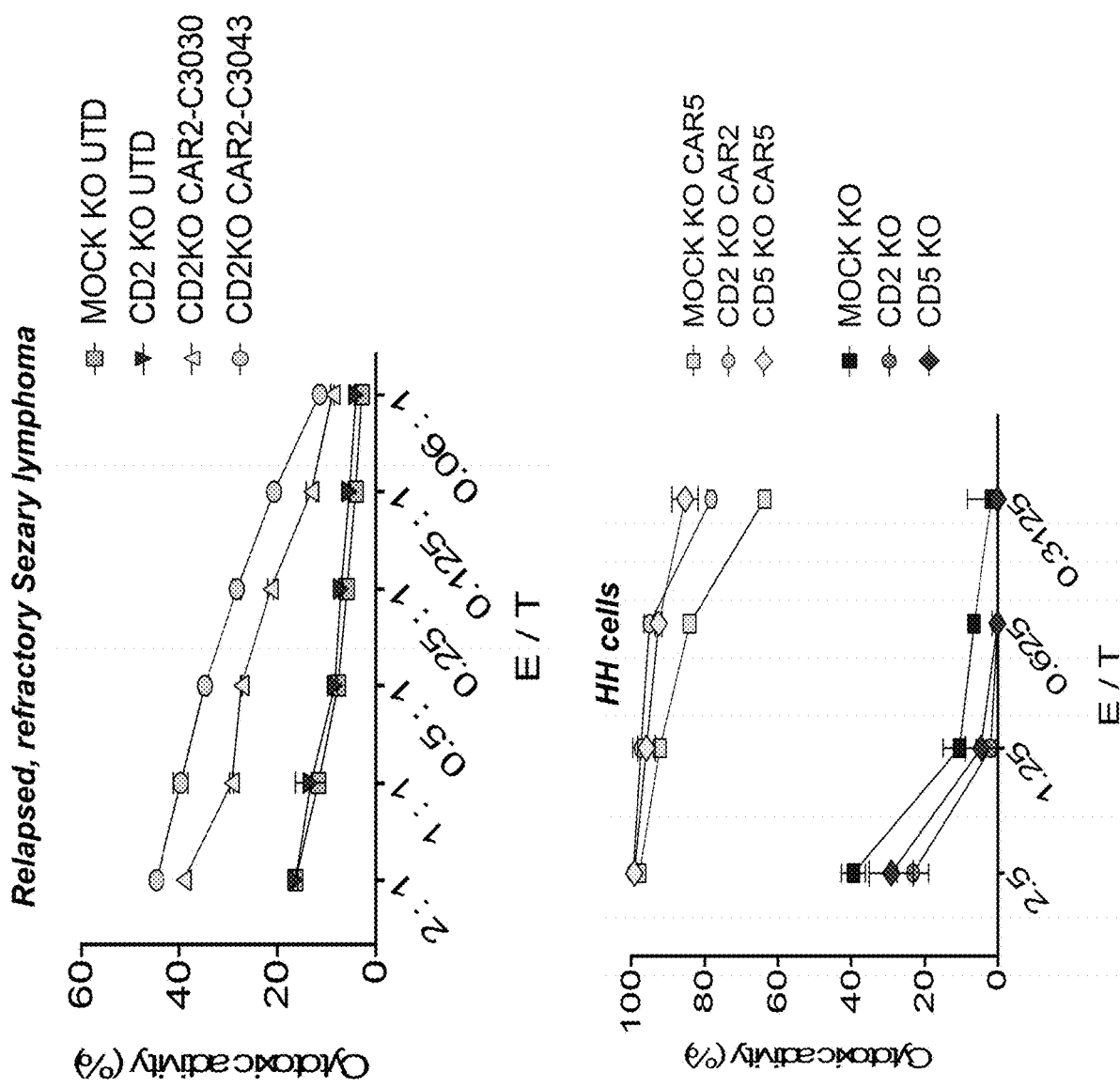

FIG. 15 illustrates CART2 and CART5 activity against cutaneous T cell lymphoma. Results from 24-hour killing assays are shown. CART2 cells are active against primary Sezary cells (leukemic Cutaneous T Cell Lymphoma) and the HH Sezary cell line. Also CART5 were active against HH cells.

Figure 16:
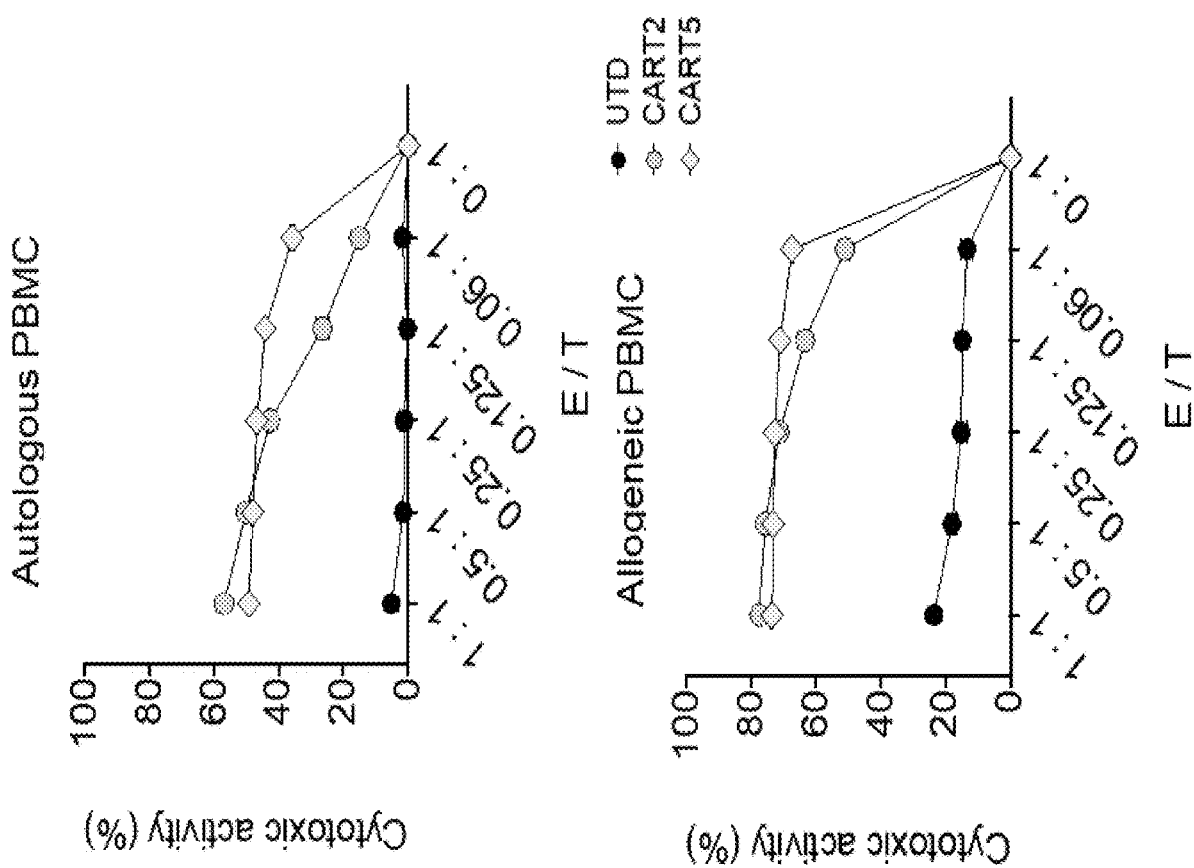

FIG. 16 illustrates the finding that CART2 and CART5 can recognize normal T cells (autologous top and allogeneic bottom) and kill them.

Figure 17:
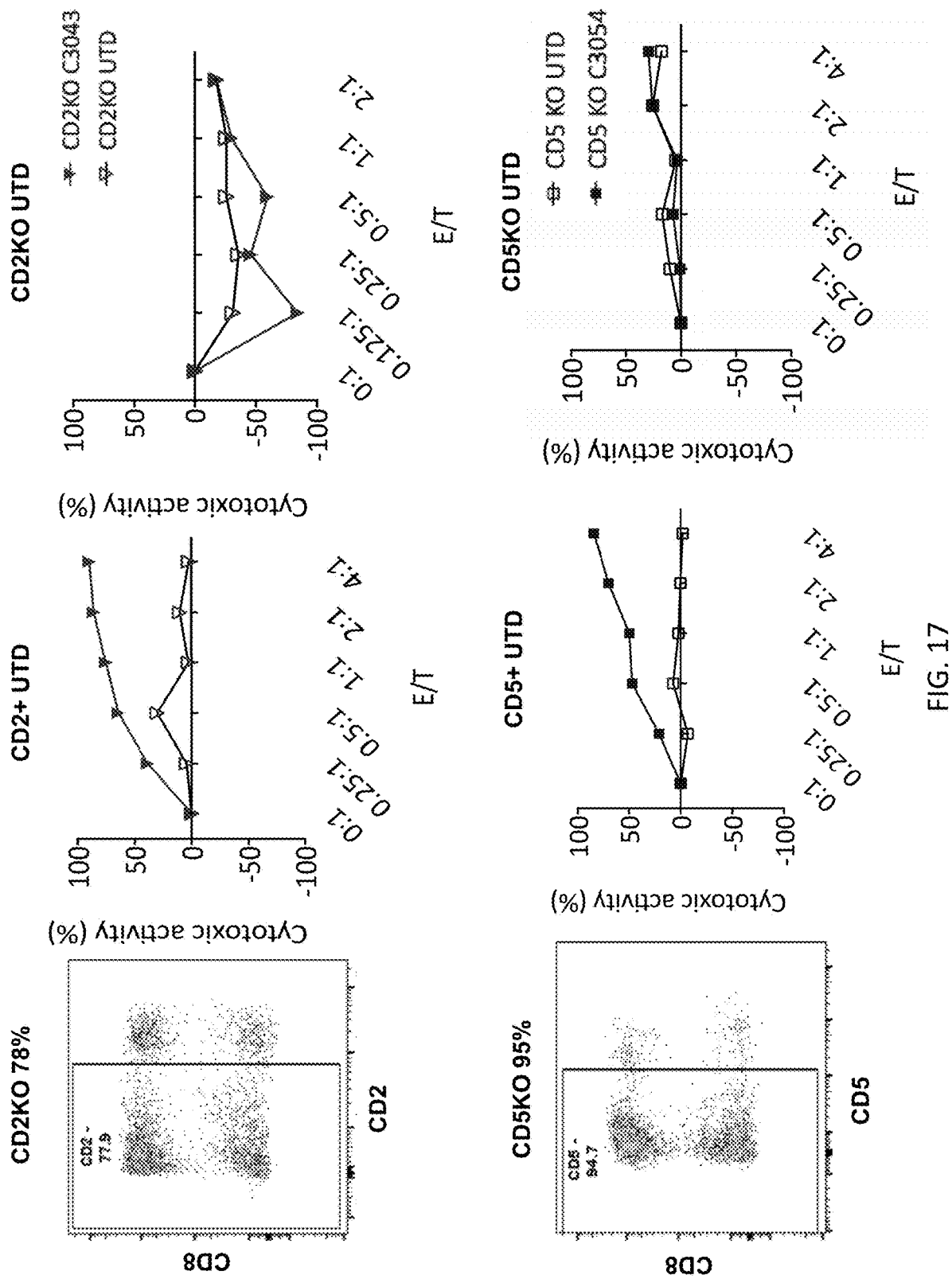

FIG. 17 illustrates the finding that removal of the CAR target protects normal T cells from CART killing. CD5 KO but not WT normal T cells are resistant to CART5 killing. Normal resting T cells are recognized and killed by CART2 (top) and CART5 (bottom). Efficient KO of CD2 or CD5 from normal T cells using CRISPR-Cas9 lead to resistance to CART2 or CART5 killing respectively.

Figure 18:
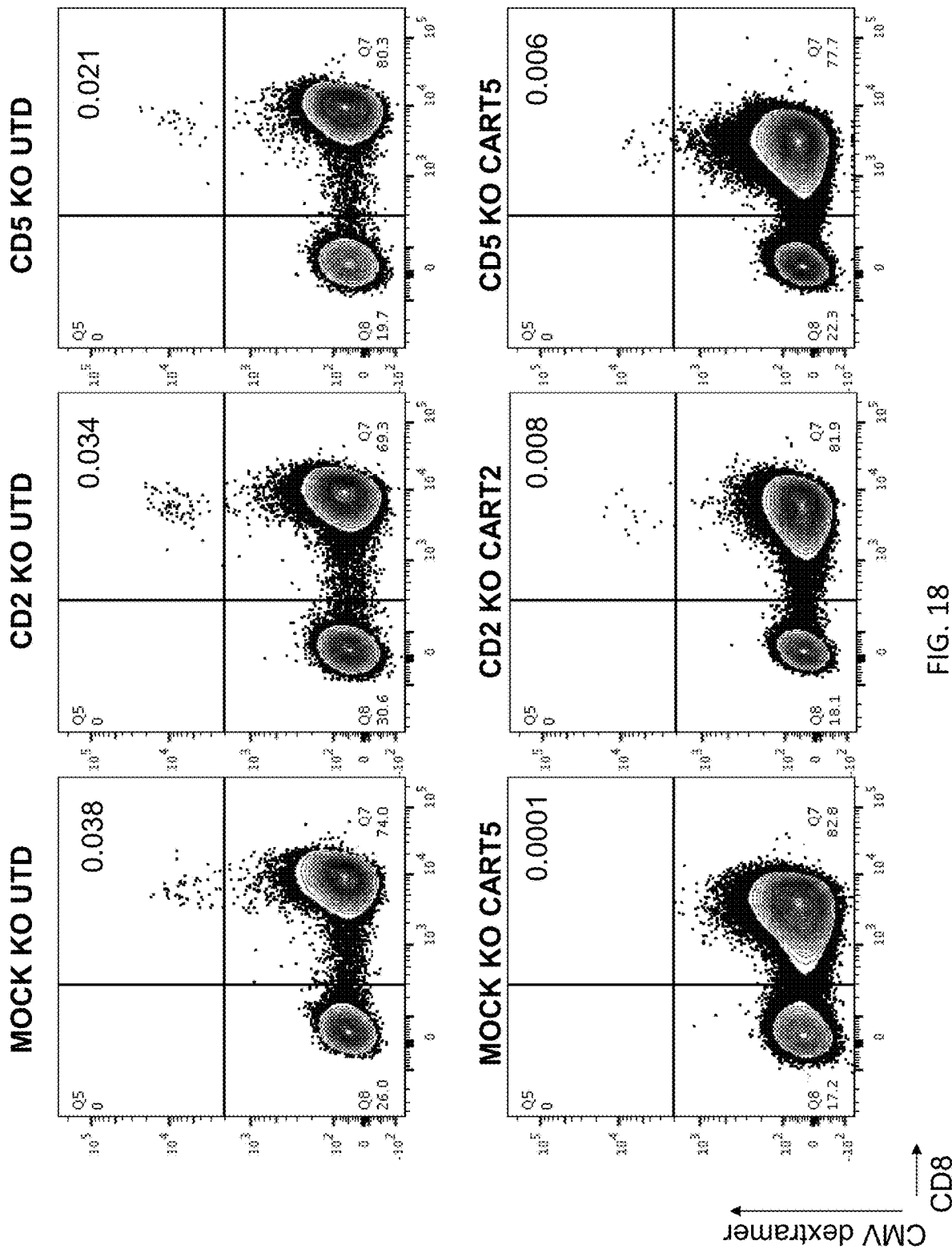

FIG. 18 illustrates the finding that CMV-specific T cells are present in CD2KO and CD5KO normal T cell products. CD2 and CD5 KO normal T cells maintain the ability to recognize CMV peptides and produce cytokines. (HLA-A-02:01-CMV PP65 NLVPMVATV dextramer (SEQ ID NO: 101); ICS after 4 h exposure to CETF peptides. After secondary culture with CMV-peptide pulsed APC).

Figure 19:
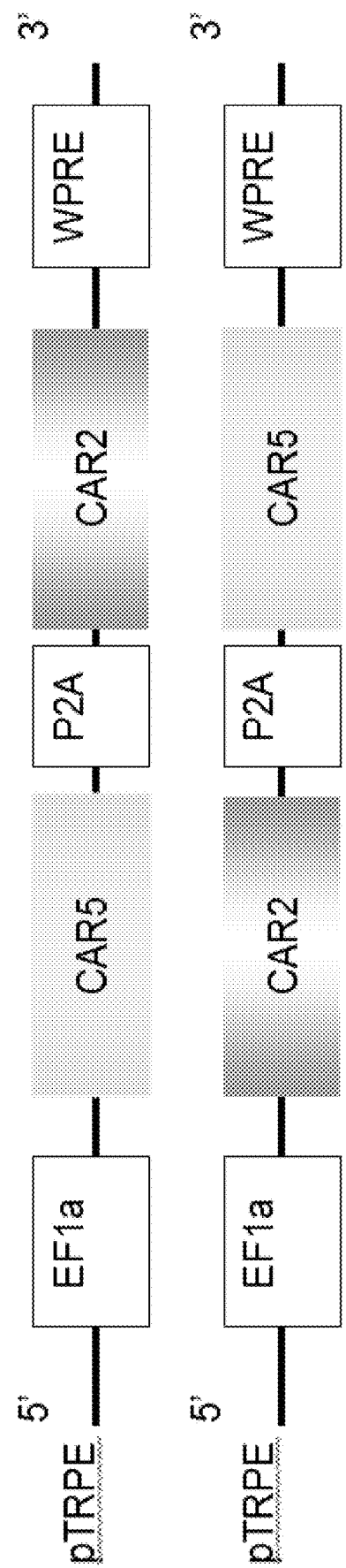

FIG. 19 illustrates the development of dual specific CAR T cells. Two lentiviral constructs were generated that included the CAR5 (C3054) and CAR2 (C3043) linked by a P2A sequence. Gene expression is driven by an EF1alpha promoter. The CAR5 constructs have 4-1BB costimulatory and CD3zeta signaling domains.

Figure 20A:
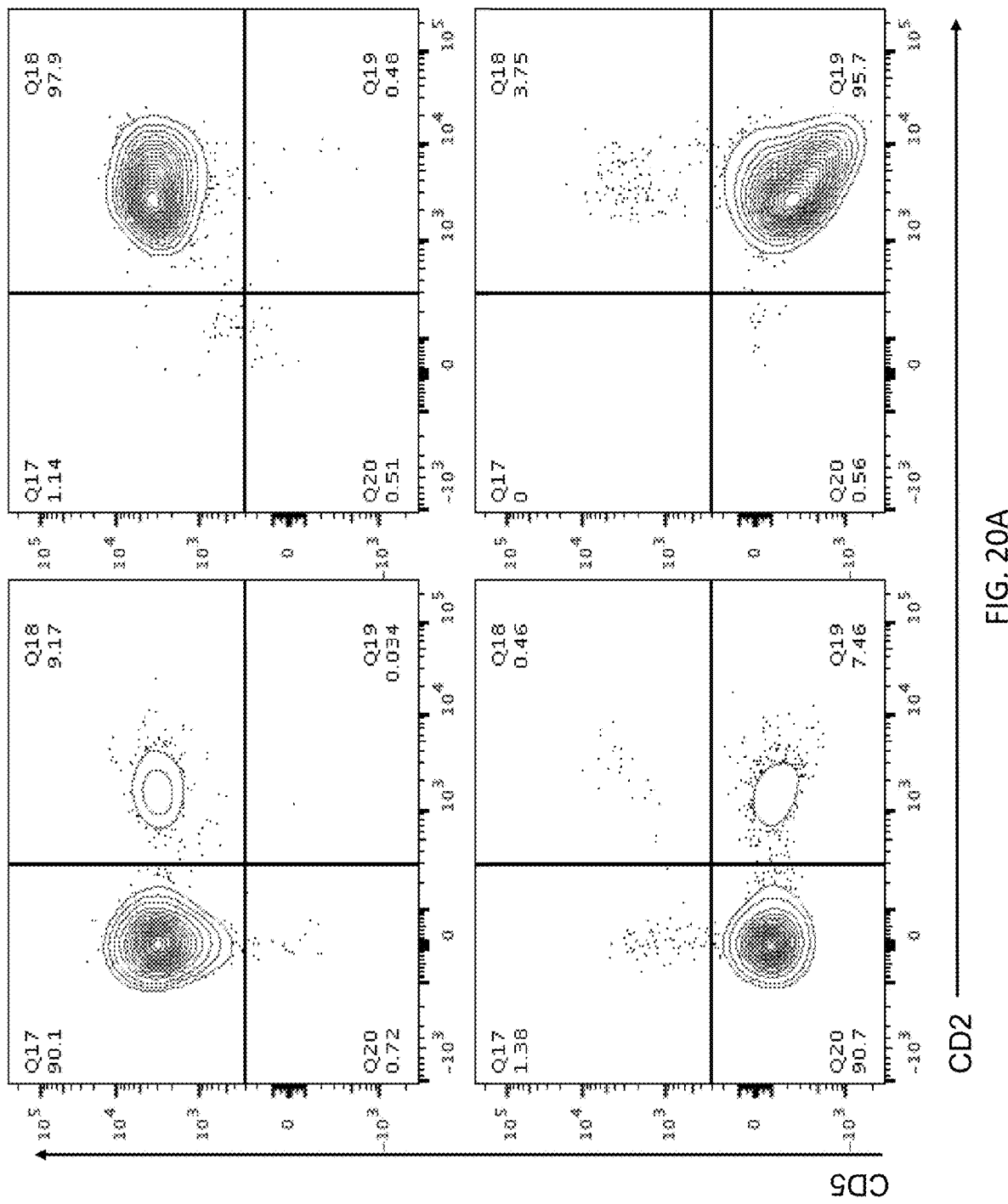
Figure 20B:
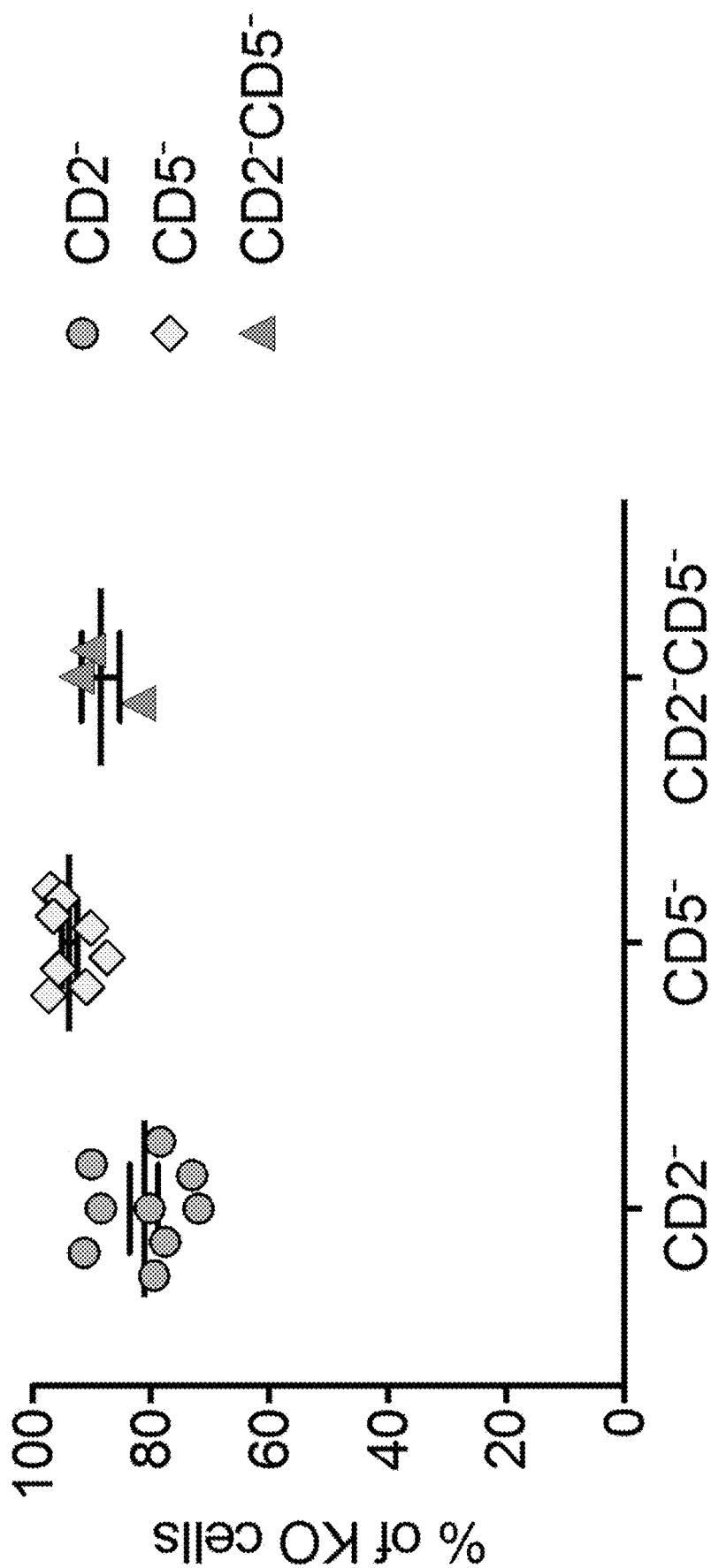

FIGS. 20A-20B illustrate dual KO CART cells. Efficient knock-out of both CD2 and CD5 in normal T cells as shown by flow cytometry.

Figure 21:
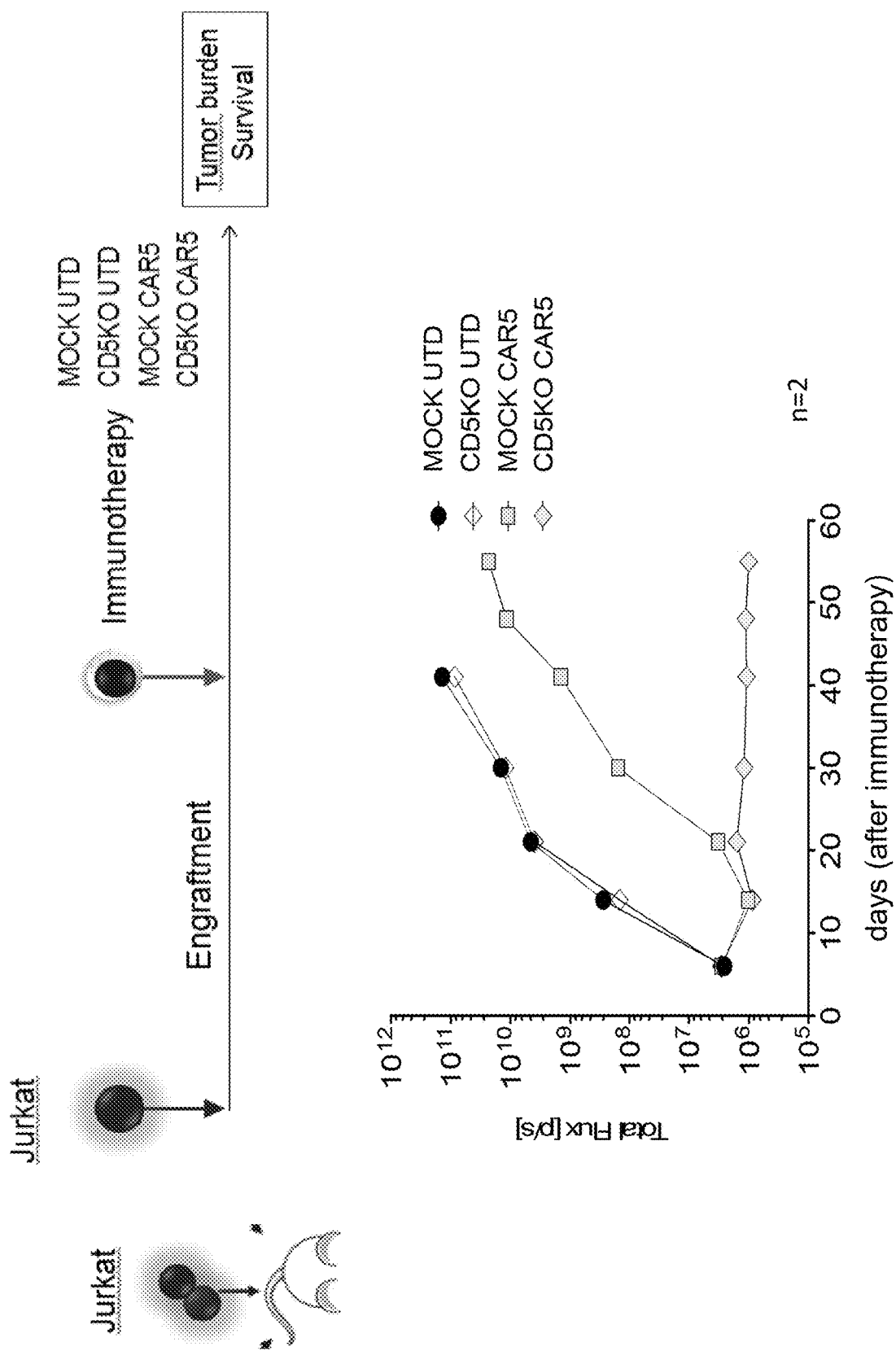

FIG. 21 illustrates the finding that CD5 KO CART5 are more effective than CD5+ CART5 in vivo. CD5 KO increases CART5 anti-tumor efficacy. In a Jurkat T-ALL xenograft model using NSG mice, CD5 KO CART5 ($2\times10^6$ cells/mouse) lead to complete long-term complete responses and longer survival as compared to WT CART5.

Figure 22:
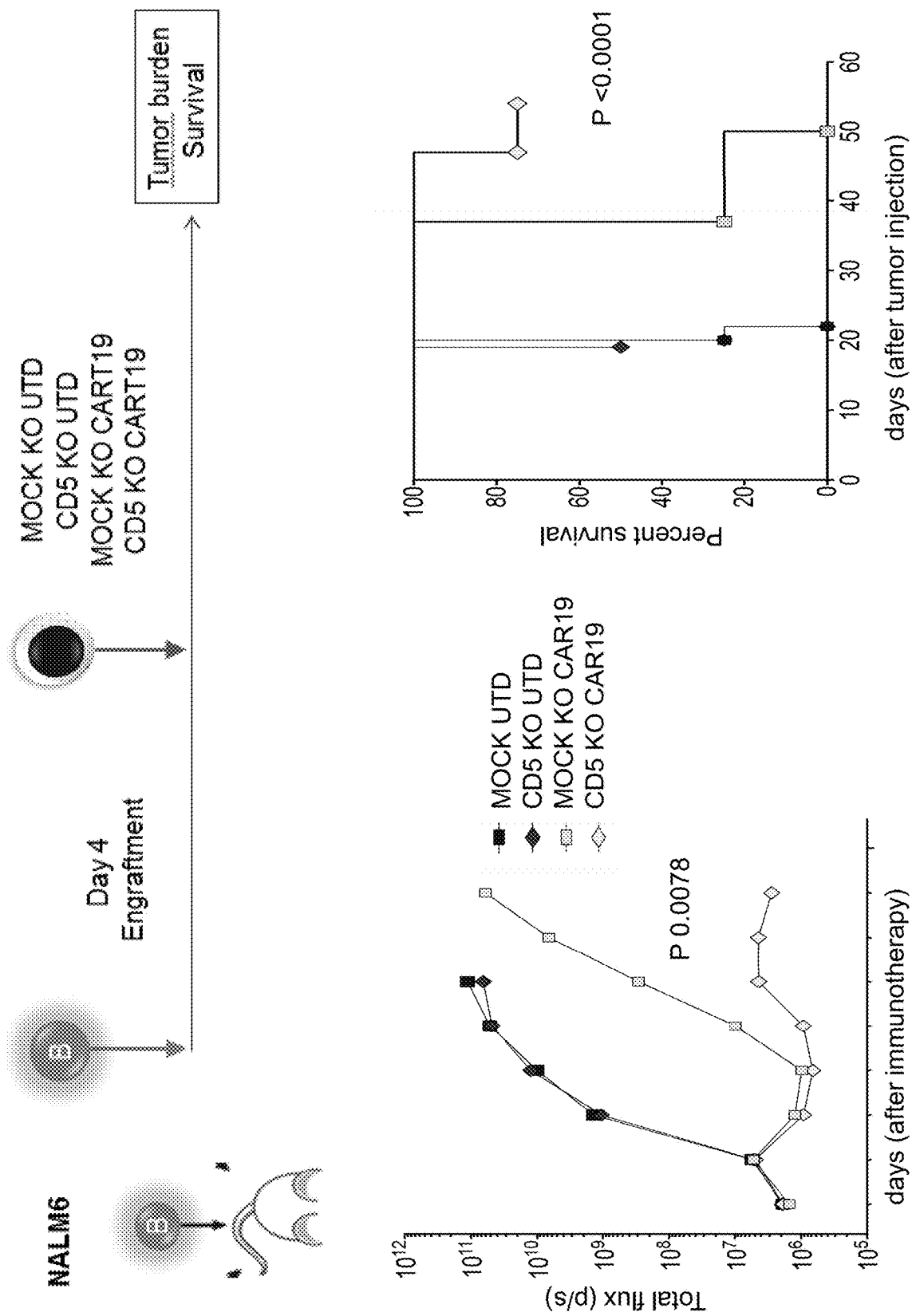

FIG. 22 illustrates the finding that CD5 KO CART19 are more effective than CD5+ CART19 in vivo. CD5 KO increases CART19 anti-tumor efficacy. In a NALM6 B-ALL xenograft model, CD5 KO CART19 have drastically higher tumor control as compared to WT CART19.

Figure 23B:
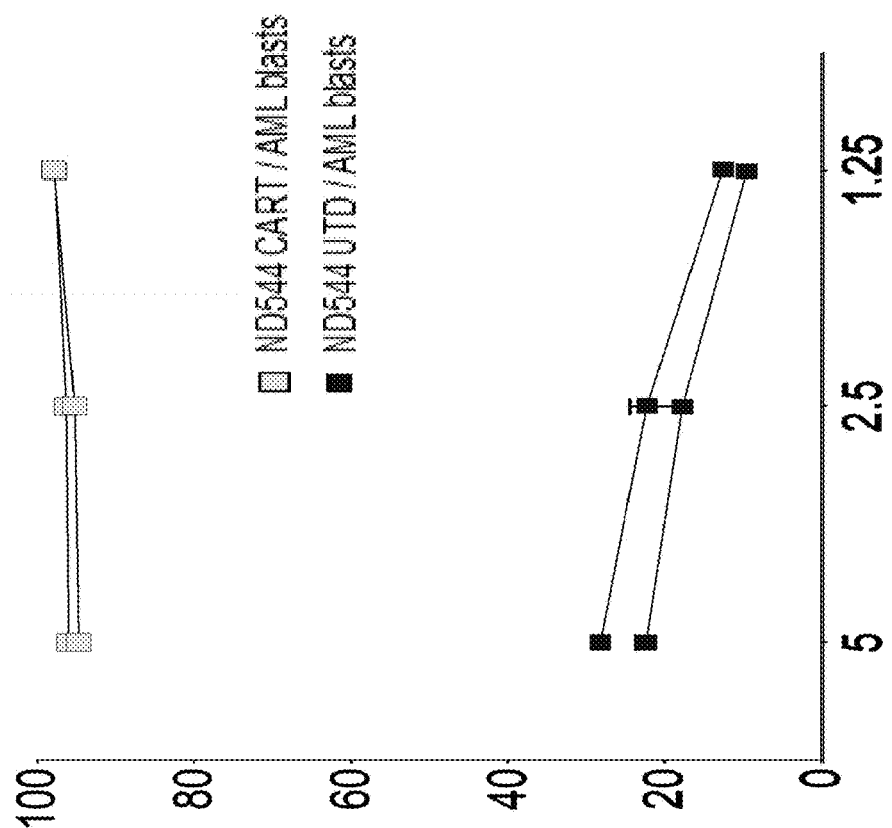
Figure 23A:
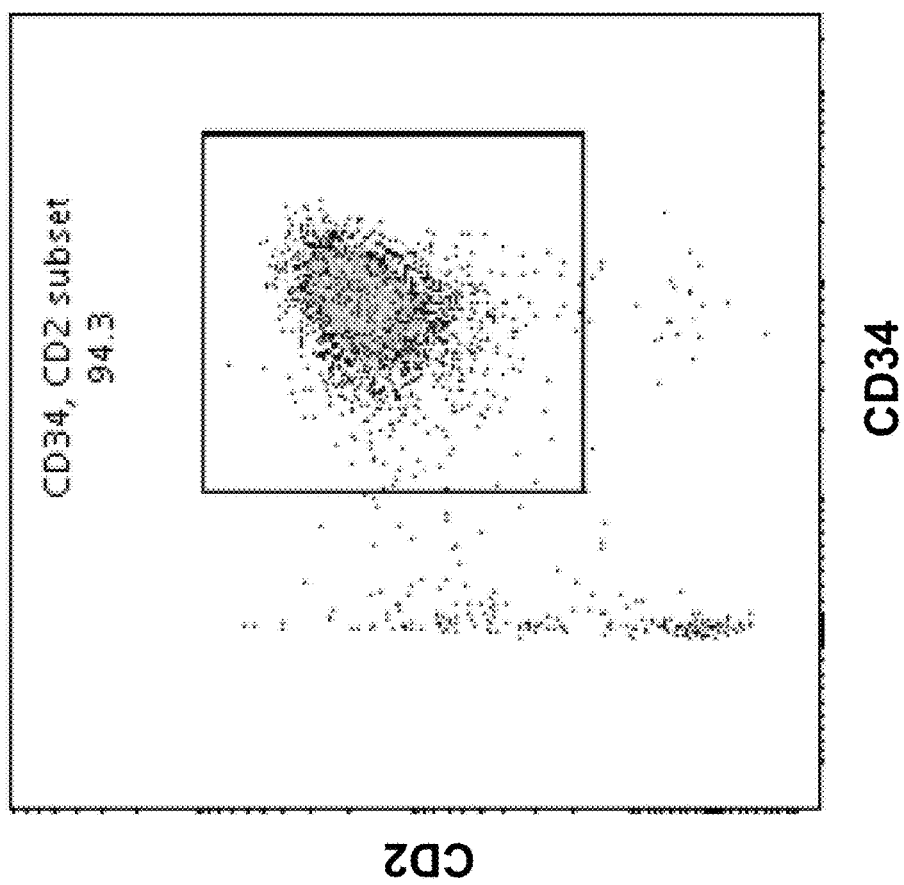

FIGS. 23A-23B illustrate the finding that CART5 and CART2 can target 20% of AML. FIG. 23A illustrates CD2 expression in AML. FIG. 23B illustrates results from a 24 hour killing assay. CART2 cells were co-cultured with CD2+ AML cells and showed significant killing at 24 hours.

Figure 24:
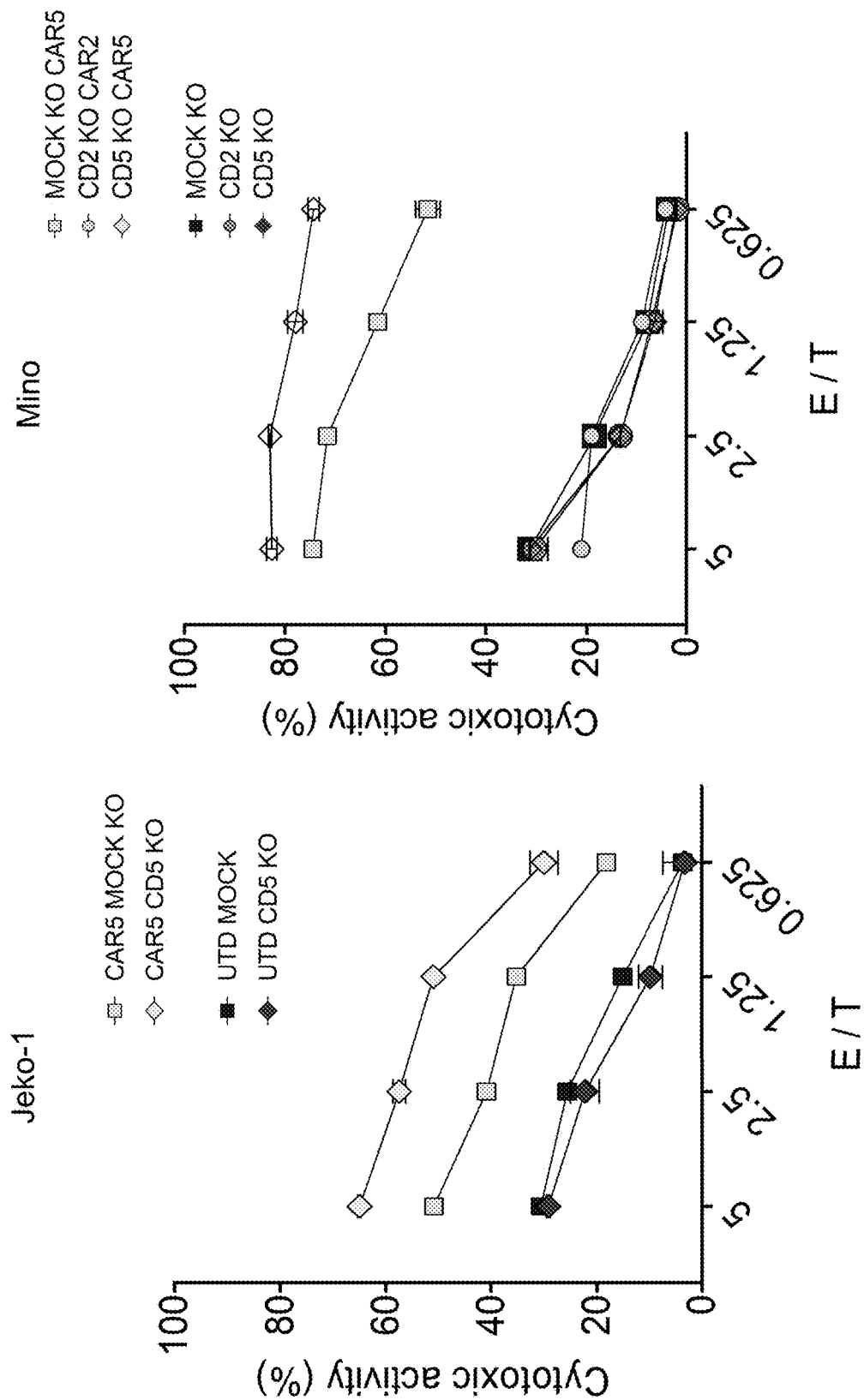

FIG. 24 illustrates the finding that CART5 can target 100% of CLL and MCL. Results are from cytotoxicity assays showing that CART5 cells can recognize and kill CD5+ MCL cell lines (Jeko-1 and Mino).

Figure 25:
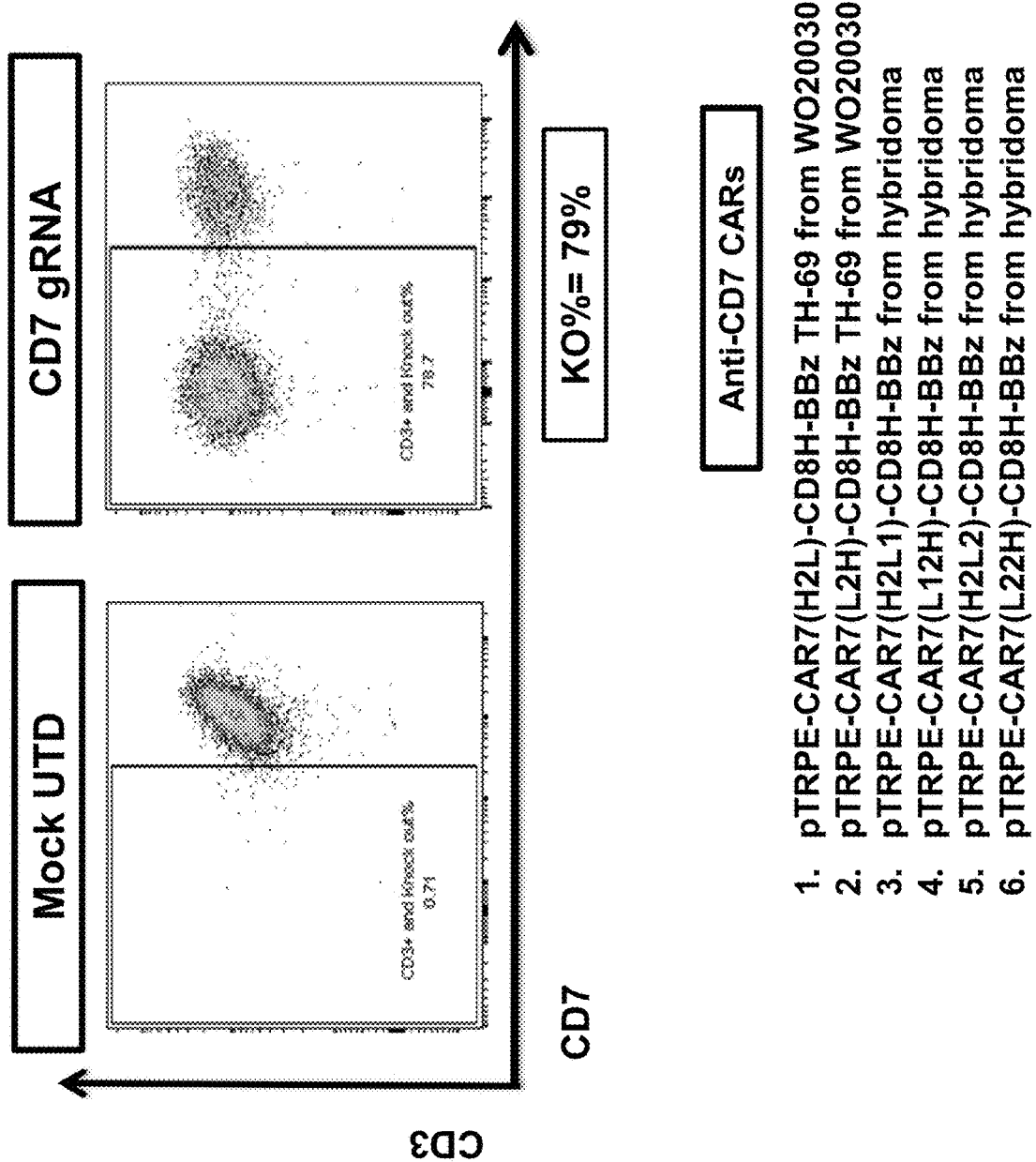

FIG. 25. illustrates development of a sgRNA to knock-out CD7 in T cells (top) and the generation of six CAR constructs against CD7.

Figure 26:
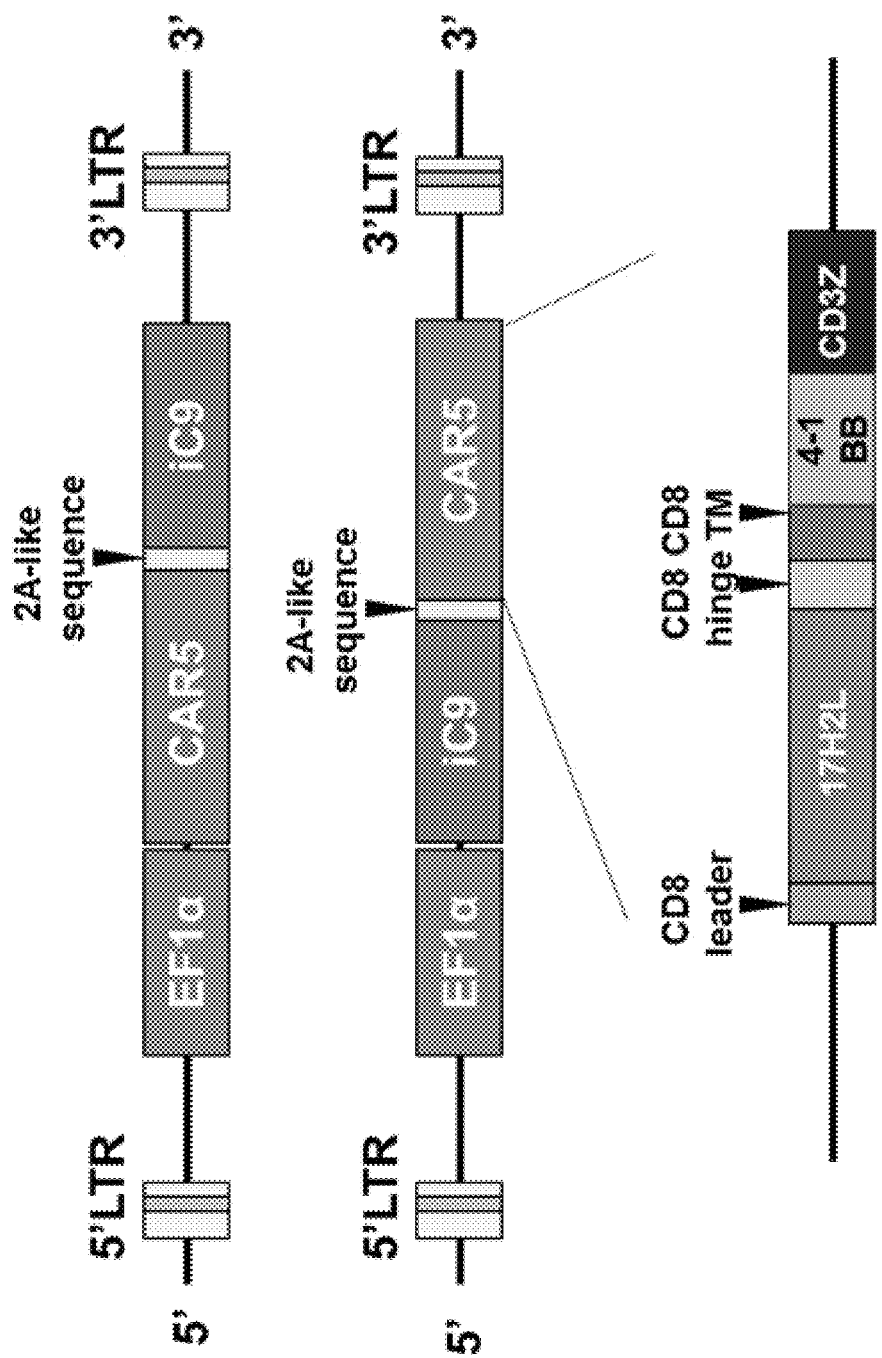

FIG. 26 illustrates Casp9-CAR5 lentiviral constructs used herein. Two lentiviral constructs were generated that included the CAR5 (C3054), a P2A sequence and then the iCaspase9 suicide gene (iC9) or iC9-P2A-C3054. Gene expression is driven by an EF1alpha promoter. The CAR5 construct has 4-1BB costimulatory and CD3zeta signaling domains.

DETAILED DESCRIPTION

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +20% or +10%, more preferably +5%, even more preferably +1%, and still more preferably +0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. Kappa and lambda light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

"Allogeneic" refers to any material derived from a different animal of the same species.

"Xenogeneic" refers to any material derived from an animal of a different species.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs has specificity to a selected target, for example a B cell surface receptor. CARs may also comprise an intracellular activation domain, a transmembrane domain and an extracellular domain comprising a tumor associated antigen binding region. In some aspects, CARs comprise an extracellular domain comprising an anti-B cell binding domain fused to CD3-zeta transmembrane and intracellular domain The term "cleavage" refers to the breakage of covalent bonds, such as in the backbone of a nucleic acid molecule or the hydrolysis of peptide bonds. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

When "an immunologically effective amount," or "therapeutic amount" is indicated, the precise amount of the compositions of the present invention to be administered can be determined by a physician or researcher with consideration of individual differences in age, weight, tumor size, extent of infection or metastasis, and condition of the patient (subject).

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

This disclosure describes three chimeric antigen receptors (CARs) that target T cell neoplasms as well as a method to prevent fratricide of healthy T cells. T cell lymphomas and leukemias are aggressive neoplasms derived from T cell progenitors or differentiated T cells. Mature or peripheral T-cell lymphomas account for 10%-15% of all non-Hodgkin's lymphomas, or ~7,000-10,000 cases in the U.S/yr. T cell lymphomas and leukemias have poor prognoses and there are few available treatments. CART therapy has demonstrated efficacy for B-cell neoplasms, but until now, extending the success of chimeric antigen receptor (CAR) T cells to T-cell malignancies has been problematic because most target antigens are shared between normal and malignant cells, leading to CAR T cell fratricide. Herein CRISPR-Cas editing is used to remove the target antigen from healthy T cells, protecting them from CART cell therapy and eliminating the potentially fatal immunosuppression that would result from elimination of the T-cell compartment.

In certain embodiments, the CARs target the T cell antigens CD2, CD5 and CD7. In certain embodiments, CRISPR-Cas knock-out of the CD2, CD5, or CD7 target in healthy T cells prevents the killing of healthy T cells during manufacturing and subsequent CART therapy.

Methods of Treatment

The present invention includes a method for treating a T cell lymphoma or T cell leukemia in a subject in need thereof. In another aspect, the invention includes a method for preventing CAR T cell fratricide in a subject in need thereof.

In certain embodiments, the method comprises administering to the subject a first modified cell comprising a chimeric antigen receptor (CAR), wherein the CAR comprises an antigen binding domain that targets CD2, a transmembrane domain, and an intracellular domain, and administering to the subject a second modified cell wherein the endogenous CD2 gene has been knocked-out.

In certain embodiments, the method comprises administering to the subject a first modified cell comprising a CAR, wherein the CAR comprises an antigen binding domain that targets CD5, a transmembrane domain, and an intracellular domain, and administering to the subject a second modified cell wherein the endogenous CD5 gene has been knocked-out.

In certain embodiments, the method comprises administering to the subject a first modified cell comprising a CAR, wherein the CAR comprises an antigen binding domain that targets CD7, a transmembrane domain, and an intracellular domain, and administering to the subject a second modified cell wherein the endogenous CD7 gene has been knocked-out.

In certain embodiments, the method comprises administering to the subject a first modified cell comprising a chimeric antigen receptor (CAR), wherein the CAR comprises an antigen binding domain, a transmembrane domain, and an intracellular domain, and administering to the subject a second modified cell wherein the endogenous CD5 gene has been knocked-out.

In certain embodiments, the method comprises administering to the subject a modified cell comprising a chimeric antigen receptor (CAR), wherein the CAR comprises an antigen binding domain, a transmembrane domain, and an intracellular domain, and wherein the endogenous CD5 gene has been knocked-out in the cell.

In the various embodiments of the methods disclosed herein, the subject can be administered any of the CARs disclosed herein. The CAR can be specific for any tumor associated antigen (TAA) or tumor specific antigen (TSA) known to one of ordinary skill in the art.

In certain embodiments, the CAR comprises a complementarity determining region (CDR) comprising the amino acid sequence selected from the group consisting of SEQ ID NOs: 31-36, 43-48, 53-58, 65-70, 83-88, and 95-100. In certain embodiments, the CAR comprises an antigen binding domain comprising a heavy chain variable region comprising an amino acid sequence selected from the group consisting of SEQ ID NOs: 29, 41, 51, 63, 75, 81, and 93 and/or a light chain variable region comprising an amino acid sequence selected from the group consisting of SEQ ID NOs: 30, 42, 52, 64, 76, 82, and 94. In certain embodiments, the CAR comprises an scFv comprising an amino acid sequence selected from the group consisting of SEQ ID NOs: 27, 28, 39, 40, 50, 61, 62, 73, 74, 79, 80, 91, and 92.

In certain embodiments, the subject is administered a CAR, wherein the CAR comprises a nucleic acid sequence encoded by any one of SEQ ID NOs: 1-13. In certain embodiments, the CAR comprises an amino acid sequence selected from the group consisting of SEQ ID NOs: 25, 26, 37, 38, 49, 59, 60, 71, 72, 77, 78, 89, and 90.

In certain embodiments, the first and or second modified cell is a T cell. In certain embodiments, the cancer comprises a T cell lymphoma or a T cell leukemia. Types of cancers that can be treated with the compositions and methods of the present invention include but are not limited to non-Hodgkins's lymphoma and subtypes thereof including peripheral T-cell lymphoma (PTCL). Angioimmunoblastic T-cell lymphoma (AITL), anaplastic lymphoma kinase (ALK)-negative anaplastic large cell lymphoma (ALCL, ALK−), Natural killer/T-cell lymphoma (NKTCL), Adult T-cell leukemia/lymphoma (ATLL), ALCL ALK+, enteropathy-type T-cell, hepatosplenic T-cell, subcutaneous panniculitis-like, and unclassifiable PTCL.

In certain embodiments, the endogenous gene (e.g. CD2, CD5, and CD7) is knocked-out using a CRISPR/Cas9 method. In certain embodiments, the CRISPR/Cas9 method utilizes an sgRNA targeting CD2, CD5, and/or CD7. In certain embodiments, the sgRNA comprises the nucleotide sequence selected from the group consisting of SEQ ID NOs: 22-24.

In certain embodiments, the CAR of present invention further comprises a suicide gene. One non-limiting example of a suicide gene is the inducible caspase 9 gene (iCaspase9, iCasp9 or iC9). The iCaspase9 suicide gene system is based on the fusion of human caspase 9 to a modified human FK-binding protein, allowing conditional dimerization using a small-molecule drug (e.g. AP1903). When exposed to a synthetic dimerizing drug, the iCaspase9 becomes activated and leads to the rapid apoptosis of cells expressing this construct (e.g. the CAR T cell) (Zhou et al. (2015) *Methods Mol Biol*. 1317: 87-105). Another example of a suicide gene is the HSV-tk gene (Bordingnon et al. (1995) *Human Gene Therapy*, vol. 6, no. 6., pp 813-819). The HSV-tk gene can be co-expressed in the CAR T cell, and upon expression it turns the non-toxic prodrug GCV into GCV-triphosphate, leading to cell death by halting DNA replication.

Compositions

One aspect of the invention includes a composition comprising a first modified cell comprising a chimeric antigen receptor (CAR), wherein the CAR comprises an antigen binding domain that targets CD2, a transmembrane domain, and an intracellular domain, and a second modified cell wherein the endogenous CD2 gene has been knocked-out.

Another aspect of the invention includes a composition comprising a first modified cell comprising a CAR, wherein the CAR comprises an antigen binding domain that targets CD5, a transmembrane domain, and an intracellular domain, and a second modified cell wherein the endogenous CD5 gene has been knocked-out.

Yet another aspect of the invention includes a composition comprising a first modified cell comprising a CAR, wherein the CAR comprises an antigen binding domain that targets CD7, a transmembrane domain, and an intracellular domain, and a second modified cell wherein the endogenous CD7 gene has been knocked-out.

In certain embodiments, the CAR is encoded by a nucleic acid sequence selected from the group consisting of SEQ ID NOs: 1-13. In certain embodiments, the endogenous genes have been knocked-out using a CRISPR/Cas system. In certain embodiments, the CRISPR/Cas9 system comprises a gRNA comprising a nucleic acid sequence selected from the group consisting of SEQ ID NOs: 22-24.

The invention further includes the composition of the invention and a pharmaceutically acceptable carrier.

Chimeric Antigen Receptor (CAR)

The present invention provides a chimeric antigen receptor (CAR) comprising an antigen binding domain, a transmembrane domain, and an intracellular domain. In certain embodiments, the invention comprises a CAR comprising an antigen binding domain capable of binding CD2, a transmembrane domain, and an intracellular domain.

Antigen Binding Domain

In one embodiment, the CAR of the invention comprises a target-specific binding element otherwise referred to as an antigen binding domain. The choice of antigen binding domain depends upon the type and number of ligands that define the surface of a target cell. For example, the antigen binding domain may be chosen to recognize a ligand that acts as a cell surface marker on target cells associated with a particular disease state (e.g. T cell lymphoma or leukemia).

In one embodiment, the CAR of the invention can be engineered to target a tumor antigen. The antigens discussed herein are merely included by way of example. The list is not intended to be exclusive and further examples will be readily apparent to those of skill in the art. Tumor antigens are proteins that are produced by tumor cells that elicit an immune response, particularly T-cell mediated immune responses. The selection of the antigen binding domain of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/ MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

Depending on the desired antigen to be targeted, the CAR of the invention can be engineered to include the appropriate antigen binding domain that is specific to the desired antigen target. For example, if CD2 is the desired antigen that is to be targeted, an antibody for CD2 can be used as the antigen binding domain for incorporation into the CAR of the invention.

In certain embodiments, the antigen binding domain of the CAR targets CD2. In certain embodiments, the antigen binding domain of the CAR targets CD5. In certain embodiments, the antigen binding domain of the CAR targets CD7.

In some embodiments, the antigen binding domain in the CAR of the invention is anti-CD2 scFV. In some embodiments, the antigen binding domain in the CAR of the invention is anti-CD5 scFV. In some embodiments, the antigen binding domain in the CAR of the invention is anti-CD7 scFV. In some embodiments, the antigen binding domain is an anti-CD2 antibody. In some embodiments, the antigen binding domain is an anti-CD5 antibody. In some embodiments, the antigen binding domain is an anti-CD7 antibody.

In certain embodiments, the antigen binding domain comprises a heavy chain variable region that comprises three heavy chain complementarity determining regions (HCDRs) and a light chain variable region that comprises three light chain complementarity determining regions (LCDRs).

In certain embodiments, the invention comprises a CAR comprising an antigen binding domain capable of binding CD2, wherein the antigen binding domain comprises a complementarity determining region (CDR) comprising the amino acid sequence of any one of SEQ ID NOs: 31, 32, 33, 34, 35, 36, 43, 44, 45, 46, 47, 48, 53, 54, 55, 56, 57, 58, 65, 66, 67, 68, 69, or 70.

In certain embodiments, the CAR comprises an antigen binding domain capable of binding CD2, wherein HCDR1 comprises the amino acid sequence of SEQ ID NO: 31, HCDR2 comprises the amino acid sequence of SEQ ID NO: 32, HCDR3 comprises the amino acid sequence of SEQ ID NO: 33, LCDR1 comprises the amino acid sequence of SEQ ID NO: 34, LCDR2 comprises the amino acid sequence of SEQ ID NO: 35, and LCDR3 comprises the amino acid sequence of SEQ ID NO: 36.

In certain embodiments, the CAR comprises an antigen binding domain capable of binding CD2, wherein HCDR1 comprises the amino acid sequence of SEQ ID NO: 43, HCDR2 comprises the amino acid sequence of SEQ ID NO: 44, HCDR3 comprises the amino acid sequence of SEQ ID NO: 45, LCDR1 comprises the amino acid sequence of SEQ ID NO: 46, LCDR2 comprises the amino acid sequence of SEQ ID NO: 47, and LCDR3 comprises the amino acid sequence of SEQ ID NO: 48.

In certain embodiments, the CAR comprises an antigen binding domain capable of binding CD2, wherein HCDR1 comprises the amino acid sequence of SEQ ID NO: 65, HCDR2 comprises the amino acid sequence of SEQ ID NO: 66, HCDR3 comprises the amino acid sequence of SEQ ID NO: 67, LCDR1 comprises the amino acid sequence of SEQ ID NO: 68, LCDR2 comprises the amino acid sequence of SEQ ID NO: 69, and LCDR3 comprises the amino acid sequence of SEQ ID NO: 70.

In certain embodiments, the CAR comprises an antigen binding domain capable of binding CD2, wherein the antigen binding domain comprises a heavy chain variable region comprising the amino acid sequence of SEQ ID NO: 29 and/or a light chain variable region comprising the amino acid sequence of SEQ ID NO: 30. In certain embodiments, the antigen binding domain comprises a heavy chain variable region comprising the amino acid sequence of SEQ ID NO: 41 and/or a light chain variable region comprising the amino acid sequence of SEQ ID NO: 42. In certain embodiments, the antigen binding domain comprises a heavy chain variable region comprising the amino acid sequence of SEQ ID NO: 51 and/or a light chain variable region comprising the amino acid sequence of SEQ ID NO: 52. In certain embodiments, the antigen binding domain comprises a heavy chain variable region comprising the amino acid sequence of SEQ ID NO: 63 and/or a light chain variable region comprising the amino acid sequence of SEQ ID NO: 64.

In certain embodiments, the CAR comprises an antigen binding domain capable of binding CD2, wherein the antigen binding domain is a scFv comprising the amino acid sequence set forth in any one of SEQ ID NOs: 27, 28, 39, 40, 50, 61, or 62.

In certain embodiments, the invention comprises a CAR comprising an antigen binding domain capable of binding CD5, wherein the antigen binding domain comprises a complementarity determining region (CDR) comprising the amino acid sequence of any one of SEQ ID NOs: 83, 84, 85, 86, 87, 88, 95, 96, 97, 98, 99, or 100.

In certain embodiments, the CAR comprises an antigen binding domain capable of binding CD5, wherein HCDR1 comprises the amino acid sequence of SEQ ID NO: 83, HCDR2 comprises the amino acid sequence of SEQ ID NO: 84, HCDR3 comprises the amino acid sequence of SEQ ID NO: 85, LCDR1 comprises the amino acid sequence of SEQ ID NO: 86, LCDR2 comprises the amino acid sequence of SEQ ID NO: 87, and LCDR3 comprises the amino acid sequence of SEQ ID NO: 88.

In certain embodiments, the CAR comprises an antigen binding domain capable of binding CD5, wherein HCDR1 comprises the amino acid sequence of SEQ ID NO: 95, HCDR2 comprises the amino acid sequence of SEQ ID NO: 96, HCDR3 comprises the amino acid sequence of SEQ ID NO: 97, LCDR1 comprises the amino acid sequence of SEQ ID NO: 98, LCDR2 comprises the amino acid sequence of SEQ ID NO: 99, and LCDR3 comprises the amino acid sequence of SEQ ID NO: 100.

In certain embodiments, the CAR comprises an antigen binding domain capable of binding CD5, wherein the antigen binding domain comprises a heavy chain variable region comprising the amino acid sequence of SEQ ID NO: 75 and/or a light chain variable region comprising the amino acid sequence of SEQ ID NO: 76. In certain embodiments, the heavy chain variable region comprises the amino acid sequence of SEQ ID NO: 81 and/or a light chain variable region comprises the amino acid sequence of SEQ ID NO: 82. In certain embodiments, the heavy chain variable region comprises the amino acid sequence of SEQ ID NO: 93 and/or a light chain variable region comprises the amino acid sequence of SEQ ID NO: 94.

In certain embodiments, the CAR comprises an antigen binding domain capable of binding CD5, wherein the antigen binding domain is a scFv comprising the amino acid sequence set forth in any one of SEQ ID NOs: 73, 74, 79, 80, 91, or 92.

Tolerable variations of the antigen binding domain sequences will be known to those of skill in the art. For example, in some embodiments the antigen binding domain comprises an amino acid sequence that has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NOs: 27, 28, 29, 30, 31, 32, 33, 34, 35, 36, 39, 40, 41, 42, 43, 44, 45, 46, 47, 48, 50, 51, 52, 53, 54, 55, 56, 57, 58, 61, 62, 63, 64, 65, 66, 67, 68, 69, 70, 73, 74, 75, 76, 79, 80, 81, 82, 83, 84, 85, 86, 87, 88, 91, 92, 93, 94, 95, 96, 97, 98, 99, or 100.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain in the CAR of the invention is a CD8 transmembrane domain. In one embodiment, the CD8 transmembrane domain comprises the nucleic acid sequence of SEQ ID NO: 14. In one embodiment, the CD8 transmembrane domain comprises the nucleic acid sequence that encodes the amino acid sequence of SEQ ID NO: 15. In another embodiment, the CD8 transmembrane domain comprises the amino acid sequence of SEQ ID NO: 15.

In some instances, the transmembrane domain of the CAR of the invention comprises the CD8a hinge domain. In one embodiment, the CD8 hinge domain comprises the nucleic acid sequence of SEQ ID NO: 16. In one embodiment, the CD8 hinge domain comprises a nucleic acid sequence that encodes the amino acid sequence of SEQ ID NO: 17. In another embodiment, the CD8 hinge domain comprises the amino acid sequence of SEQ ID NO: 17.

Between the antigen binding domain and the transmembrane domain of the CAR, or between the intracellular domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

Intracellular Domain

The intracellular domain or otherwise the cytoplasmic domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular domain" refers to the portion of a protein which transduces the effector function signal and directs the cell to perform a specialized function. While usually the entire intracellular domain can be employed, in many cases it is not necessary to use the entire chain. To the extent that a truncated portion of the intracellular domain is used, such truncated portion may be used in place of the intact chain as long as it transduces the effector function signal. The term intracellular domain is thus meant to include any truncated portion of the intracellular domain sufficient to transduce the effector function signal.

Preferred examples of intracellular domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the intracellular domain of the CAR can be designed to comprise the CD3-zeta signaling domain by itself or combined with any other desired intracellular domain(s) useful in the context of the CAR of the invention. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include, but are not limited to, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention is exemplified primarily with 4-1BB as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR of the invention is designed to comprise the signaling domain of 4-1BB and the signaling domain of CD3-zeta, wherein the signaling domain of 4-1BB comprises the nucleic acid sequence set forth in SEQ ID NO: 18 and the signaling domain of CD3-zeta comprises the nucleic acid sequence set forth in SEQ ID NO: 19.

In one embodiment, the intracellular domain in the CAR of the invention is designed to comprise the signaling domain of 4-1BB and the signaling domain of CD3-zeta, wherein the signaling domain of 4-1BB comprises a nucleic acid sequence that encodes the amino acid sequence of SEQ ID NO: 20 and the signaling domain of CD3-zeta comprises a nucleic acid sequence that encodes the amino acid sequence of SEQ ID NO: 21.

In one embodiment, the intracellular domain in the CAR of the invention is designed to comprise the signaling domain of 4-1BB and the signaling domain of CD3-zeta, wherein the signaling domain of 4-1BB comprises the amino acid sequence set forth in SEQ ID NO: 20 and the signaling domain of CD3-zeta comprises the amino acid sequence set forth in SEQ ID NO: 21.

In one embodiment, the anti-CD2 CAR comprises the amino acid sequence set forth in any one of SEQ ID NOs: 25, 26, 37, 38, 49, 59, or 60. In one embodiment, the anti-CD2 CAR is encoded by a nucleic acid sequence selected from the group consisting of SEQ ID NOs: 1-7. In one embodiment, the anti-CD5 CAR comprises the amino acid sequence set forth in any one of SEQ ID NOs: 71, 72, 77, 78, 89, or 90. In one embodiment, the anti-CD5 CAR is encoded by a nucleic acid sequence selected from the group consisting of SEQ ID NOs: 8-13.

Tolerable variations of the CAR sequences will be known to those of skill in the art. For example, in some embodiments the CAR comprises an amino acid sequence that has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NO: 25, 26, 37, 38, 49, 59, 60, 71, 72, 77, 78, 89, or 90. In some embodiments the CAR is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least or 99% sequence identity to the nucleic acid sequence set forth in SEQ ID NO: 1, 2, 3, 4, 5, 6, 7, 8, 9, 10, 11, 12, or 13.

The invention should be construed to include any one of: a CAR, a nucleic acid encoding a CAR, a vector comprising a nucleic acid encoding a CAR, a cell comprising a CAR, a cell comprising a nucleic acid encoding a CAR, and a cell comprising a vector comprising a nucleic acid encoding a CAR.

```
CD2-MEDI507H2L-3028 CAR (SEQ ID NO: 1)
ggatccCAAGTCCAACTGGTGCAATCAGGCGCAGAAGTCCAACGACCGGGGGCCAG
TGTTAAAGTGTCTTGTAAAGCCTCCGGGTACATTTTTACTGAGTACTATATGTACT
GGGTCAGACAGGCCCCAGGGCAAGGTTTGGAACTTGTCGGACGCATAGATCCCG
AAGACGGTTCTATAGATTACGTTGAGAAGTTCAAAAAGAAAGTCACACTTACTG
CGGACACATCTAGTAGCACCGCATATATGGAACTGAGCAGTCTCACCTCAGACG
ACACCGCAGTGTACTATTGCGCTCGCGGAAAGTTTAACTATAGGTTCGCGTACTG
GGGACAGGGGACACTGGTGACTGTTAGCAGCggtggcggagggagcggcggtggaggaagcggag
gcggaggttccGACGTTGTGATGACGCAAAGTCCCCCGTCACTCCTTGTTACTCTCGGC
CAGCCAGCGTCTATCTCTTGCCGGTCAAGCCAGAGCTTGCTCCACTCTAGTGGTA
ACACGTATTTGAACTGGTTGCTGCAAAGGCCTGGACAATCTCCTCAGCCCCTGAT
CTATTTGGTTAGCAAACTGGAAAGTGGTGTTCCAGACAGATTTTCAGGGTCTGGA
TCAGGCACTGATTTCACTCTGAAGATCTCCGGGGTAGAGGCCGAGGACGTGGGA
GTCTATTACTGCATGCAGTTTACTCACTATCCTTATACCTTTGGTCAAGGGACGA
AACTGGAGATCAAAtccgga
```

CD2-OKT11H2L-3029 CAR (SEQ ID NO: 2)
ggatccCAAGTTCAGCTTCAGCAACCAGGTGCTGAATTGGTCCGCCCTGGAACTAGC
GTTAAACTGTCTTGTAAGGCATCCGGTTATACGTTTACAAGTTATTGGATGCACT
GGATTAAGCAAAGGCCCGAACAAGGCCTTGAATGGATTGGGAGAATTGATCCCT
ACGATAGCGAGACACACTACAATGAAAAATTTAAAGATAAGGCCATCCTCAGCG
TAGATAAGAGCAGTTCTACCGCATACATACAGCTCTCAAGCCTGACGTCAGATG
ACTCAGCCGTTTATTATTGCTCAAGGCGGGACGCTAAATACGACGGCTATGCGCT
TGACTACTGGGGACAAGGCACCACTTTGACAGTCTCCAGTggtggcggagggagcggcggt
ggaggaagcggaggcggaggttccGATATAGTTATGACGCAAGCAGCACCCTCTGTACCTGT
GACACCGGGTGAATCCGTTAGTATCTCATGCCGCTCTTCTAAAACCCTCTTGCAT
TCTAACGGCAATACATATTTGTATTGGTTCCTTCAACGACCAGGACAATCACCGC
AAGTGCTTATTTATAGGATGTCTAACTTGGCTAGTGGGGTGCCAAATAGGTTCAG
TGGGTCTGGATCTGAGACAACTTTCACGTTGAGAATAAGTAGGGTGGAAGCTGA
AGACGTCGGTATATACTGTATGCAGCATTTGGAGTACCCTTACACTTTCGGG
GGAGGTACTAAGCTCGAAATTAAAtccgga CD2-OKT11L2H-3030 CAR (SEQ ID NO: 3)
ggatccGATATAGTTATGACGCAAGCAGCACCCTCTGTACCTGTGACACCGGGTGAA
TCCGTTAGTATCTCATGCCGCTCTTCTAAAACCCTCTTGCATTCTAACGGCAATAC
ATATTTGTATTGGTTCCTTCAACGACCAGGACAATCACCGCAAGTGCTTATTTAT
AGGATGTCTAACTTGGCTAGTGGGGTGCCAAATAGGTTCAGTGGGTCTGGATCTG
AGACAACTTTCACGTTGAGAATAAGTAGGGTGGAAGCTGAAGACGTCGGTATAT
ACTACTGTATGCAGCATTTGGAGTACCCTTACACTTTCGGGGGAGGTACTAAGCT
CGAAATTAAAggtggcggagggagcggcggtggaggaagcggaggcggaggttccCAAGTTCAGCTTCA
GCAACCAGGTGCTGAATTGGTCCGCCCTGGAACTAGCGTTAAACTGTCTTGTAAG
GCATCCGGTTATACGTTTACAAGTTATTGGATGCACTGGATTAAGCAAAGGCCCG
AACAAGGCCTTGAATGGATTGGGAGAATTGATCCCTACGATAGCGAGACACACT
ACAATGAAAAATTTAAAGATAAGGCCATCCTCAGCGTAGATAAGAGCAGTTCTA
CCGCATACATACAGCTCTCAAGCCTGACGTCAGATGACTCAGCCGTTTATTATTG
CTCAAGGCGGGACGCTAAATACGACGGCTATGCGCTTGACTACTGGGGACAAGG
CACCACTTTGACAGTCTCCAGTtccgga CD2-T11-2-H2L-3031 CAR (SEQ ID NO: 4)
ggatccCAAGTTCAATTGCAGCAACCGGGTGCCGAGTTGGTAAGGCCCGGTGCGTC
AGTCAAACTTAGTTGTAAAGCTAGTGGGTACACTTTTACTACGTTCTGGATGAAT
TGGGTGAAGCAACGACCAGGCCAAGGTCTGGAATGGATCGGCATGATTGACCCG
TCTGACTCAGAAGCTCATTACAACCAGATGTTCAAGGACAAGGCGACTCTGACT
GTTGATAAAAGCTCAAGCACCGCCTACATGCAGCTCAGTAGCCTCACATCCGAG
GATTCCGCAGTGTACTATTGCGCGAGGGGACGAGGGTATGACGGCGATGCG
ATGGACTATTGGGGACAGGGGACCAGCGTAACAGTCAGTAGTggtggcggagggagcgg
cggtggaggaagcggaggcggaggttccGATATAGTTATGACCCAGTCTCCCGCCTCTCTGGCC
GTTAGCTTGGGACAACGCGCTACCATCTCTTACCGAGCGTCTAAGTCCGTCAGTA
CAAGCGGTTATAGTTACATGCACTGGAACCAGCAAAAGCCCGGACAACCTCCGA
GACTCCTGATTTATTTGGTCTCTAACCTTGAGTCAGGTGTCCCAGCCAGATTCTCC
GGCTCTGGAAGCGGCACTGACTTTACATTGAACATTCACCCCGTGGAGGAGGAA
GACGCTGCTACCTACTATTGCATGCAATTCACGCACTATCCCTACACATTCGGGG
GGGGCACGAAATTGGAAATCAAAtccgga CD2-TS2-18.1.1-H2L-3032 CAR (SEQ ID NO: 5)
ggatccGAGGTTCAGCTTGAGGAGAGTGGGGGAGGTTTGGTAATGCCAGGTGGGTC
TTTGAAACTCAGTTGCGCGGCGTCAGGCTTCGCATTTTCCTCCTACGATATGTCCT
GGGTCAGACAGACACCCGAGAAGCGGCTGGAATGGGTCGCTTACATTTCCGGGG
GAGGATTCACGTACTACCCGGATACAGTAAAGGGGAGATTTACTCTGAGCCGGG
ACAACGCTAAGAATACCCTCTATCTCCAGATGTCCTCTTTGAAGAGTGAAGACAC
AGCGATGTATTACTGTGCGAGACAAGGGGCCAATTGGGAGCTGGTTTACTGGGG
CCAGGGGACGACATTGACGGTTTCTAGCggtggcggagggagcggcggtggaggaagcggaggcgg
aggttccGACATTGTAATGACACAATCACCTGCTACACTTAGCGTGACTCCAGGTGA
TCGGGTATTCCTGAGCTGCCGCGCATCACAAAGTATATCCGACTTCCTGCACTGG
TATCAGCAGAAATCTCACGAAAGTCCCAGGCTGCTGATTAAATACGCTTCCCAG
AGTATTAGTGGTATCCCCTCACGATTTTCTGGCAGCGGGAGCGGTAGTGACTTCA
CTCTTTCTATAAACTCCGTCGAGCCAGAAGACGTGGGGGTGTATCTTTGCCAAAA
TGGACACAATTTTCCACCAACCTTTGGTGGGGGCACCAAACTCGAAATAAAGtccg
ga CD2-TS2-18.1.1-L2H-3033 CAR (SEQ ID NO: 6)
ggatccGACATTGTAATGACACAATCACCTGCTACACTTAGCGTGACTCCAGGTGAT
CGGGTATTCCTGAGCTGCCGCGCATCACAAAGTATATCCGACTTCCTGCACTGG
ATCAGCAGAAATCTCACGAAAGTCCCAGGCTGCTGATTAAATACGCTTCCCAGA
GTATTAGTGGTATCCCCTCACGATTTTCTGGCAGCGGGAGCGGTAGTGACTTCAC
TCTTTCTATAAACTCCGTCGAGCCAGAAGACGTGGGGGTGTATCTTTGCCAAAAT
GGACACAATTTTCCACCAACCTTTGGTGGGGGCACCAAACTCGAAATAAAGggtgg
cggagggagcggcggtggaggaagcggaggcggaggttccGAGGTTCAGCTTGAGGAGAGTGGGGGA
GGTTTGGTAATGCCAGGTGGGTCTTTGAAACTCAGTTGCGCGGCGTCAGGCTTCG
CATTTTCCTCCTACGATATGTCCTGGGTCAGACAGACACCCGAGAAGCGGCTGG
AATGGGTCGCTTACATTTCCGGGGGAGGATTCACGTACTACCCGGATACAGTAA
AGGGGAGATTTACTCTGAGCCGGGACAACGCTAAGAATACCCTCTATCTCCAGA
TGTCCTCTTTGAAGAGTGAAGACACAGCGATGTATTACTGTGCGAGACAAGGGG
CCAATTGGGAGCTGGTTTACTGGGGCCAGGGGACGACATTGACGGTTTCTAGCtcc
gga CD2-MEDI507L2H-3043 CAR (SEQ ID NO: 7)
ggatccGACGTTGTGATGACGCAAAGTCCCCGTCACTCCTTGTTACTCTCGGCCAG
CCAGCGTCTATCTCTTGCCGGTCAAGCCAGAGCTTGCTCCACTCTAGTGGTAACA
CGTATTTGAACTGGTTGCTGCAAAGGCCTGGACAATCTCCTCAGCCCCTGATCTA
TTTGGTTAGCAAACTGGAAAGTGGTGTTCCAGACAGATTTTCAGGGTCTGGATCA
GGCACTGATTTCACTCTGAAGATCTCCGGGGTAGAGGCCGAGGACGTGGGAGTC
TATTACTGCATGCAGTTTACTCACTATCCTTATACCTTTGGTCAAGGGACGAAAC
TGGAGATCAAAggtggcggagggagcggcggtggaggaagcggaggcggaggttccCAAGTCCAACTGG
TGCAATCAGGCGCAGAAGTCCAACGACCGGGGGCCAGTGTTAAAGTGTCTTGTA
AAGCCTCCGGGTACATTTTTACTGAGTACTATATGTACTGGGTCAGACAGGCCCC
AGGGCAAGGTTTGGAACTTGTCGGACGCATAGATCCCGAAGACGGTTCTATAGA
TTACGTTGAGAAGTTCAAAAAGAAAGTCACACTTACTGCGGACACATCTAGTAG
CACCGCATATATGGAACTGAGCAGTCTCACCTCAGACGACACCGCAGTGTACTA
TTGCGCTCGCGGAAAGTTTAACTATAGGTTCGCGTACTGGGGACAGGGGACACT
GGTGACTGTTAGCAGCtccgga CD5-17L2H-3045 CAR (SEQ ID NO: 8)
ggatccAACATTGTACTGACGCAAAGCCCCTCATCTTTGTCTGAGTCACTCGGCGGC
AAAGTAACCATCACATGCAAGGCCAGTCAAGACATCAATAAATATATTGCTTGG
TATCAGTATAAACCCGGCAAGGGGCCGCGACTGCTGATTCACTACACGAGTACC
TTGCAACCGGGCATTCCGAGCCGATTTAGTGGCAGTGGCTCAGGTCGCGATTACT
CATTCTCAATAAGTAATCTCGAACCGGAAGACATAGCTACTTATTATTGCTTGCA
GTACGATAATTTGTGGACCTTCGGGGGTGGTACAAAGTTGGAAATAAAGggtggcgg
agggagcggcggtggaggaagcggaggcggaggttccGAGGTCCAACTCGTAGAATCAGGTCCCGG
ATTGGTGCAACCATCCCAGAGCCTCTCTATTACATGCACGGTCTCTGGATTTAGT
CTGACCAATTACGATGTGCATTGGGTGCGCCAGTCTCCCGGCAAGGGGTTGGAA
TGGCTTGCGTTATATGGAACTACGGAATACAGACTATAACGCCGCGTTTATCT
CTCGGCTGAGTATACGGAAAGACAGTAGTAAATCCCAGGTCTTTTTTACGATGTC
ATCCCTGCAAACGCCAGATACCGCAATATATTACTGCGCCAGGAACCACGGTGA
TGGTTATTATAATTGGTACTTCGATGTGTGGGGTACTGGCACTACAGTCACAGTA
TCTTCAtctaga CD5-9H2L-3048 CAR (SEQ ID NO: 9)
ggatcc CAG GTC CAG CTG AAA GAA AGC GGT CCA GAG CTG AAA AAA CCC
GGT GCG AGC GTC AAA ATA TCA TGT AAA GCA AGC GGG TAT TCA TTC ACC
GCG TAC TCT ATG AAC TGG GTT AAG CAA AAC AAC GGT ATG TCC TTG GAG
TGG ATA GGG TCT ATC GAC CCG TAT TAT GGG GAC ACA AAA TAC GCG CAG
AAA TTC AAG GGG AAG GCC ACC CTG ACC GTA GAT AAA GCT AGT TCT ACT
GCG TAC TTG CAA CTG AAA AGC CTC ACT TCT GAG GAC TCT GCC GTC TAC
TAC TGT GCT CGG CGA ATG ATA ACG ACG GGG GAC TGG TAT TTC GAT GTT
TGG GGT ACA GGG ACT ACG GTG ACT GTC AGT
AGCggtggcggagggagcggcggtggaggaagcggaggcggaggttcc CAT ATC GTC TTG ACT CAA
TCA CCT AGT TCT TTG TCT GCG TCC CTT GGC GAC CGA GTC ACC ATA TCT
TGC AGA GCG TCA CAG GAC ATT TCA ACG TAC CTC AAC TGG TAT CAG CAA
AAA CCG GAC GGG ACT GTC AAG CTC TTG ATC TTC TAC ACT TCC AGA CTC
CAC GCC GGG GTG CCA AGC AGA TTT AGT GGC TCT GGC AGC GGG ACA CAC
CAT AGT CTT ACA ATC AGC AAT CTT GAG CAA GAA GAC ATA GCC ACG TAT
TTC TGC CAG CAA GGT AAC TCA CTT CCG TTC ACG TTT GGT AGT GGC ACC
AAA CTG GAG ATA AAA tccgga CD5-9L2H-3049 CAR (SEQ ID NO: 10)
Ggatcc CAT ATC GTC TTG ACT CAA TCA CCT AGT TCT TTG TCT GCG TCC CTT
GGC GAC CGA GTC ACC ATA TCT TGC AGA GCG TCA CAG GAC ATT TCA ACG
TAC CTC AAC TGG TAT CAG CAA AAA CCG GAC GGG ACT GTC AAG CTC TTG
ATC TTC TAC ACT TCC AGA CTC CAC GCC GGG GTG CCA AGC AGA TTT AGT
GGC TCT GGC AGC GGG ACA CAC CAT AGT CTT ACA ATC AGC AAT CTT GAG
CAA GAA GAC ATA GCC ACG TAT TTC TGC CAG CAA GGT AAC TCA CTT CCG
TTC ACG TTT GGT AGT GGC ACC AAA CTG GAG ATA AAA
ggtggcggagggagcggcggtggaggaagcggaggcggaggttcc CAG GTC CAG CTG AAA GAA AGC
GGT CCA GAG CTG AAA AAA CCC GGT GCG AGC GTC AAA ATA TCA TGT AAA
GCA AGC GGG TAT TCA TTC ACC GCG TAC TCT ATG AAC TGG GTT AAG CAA
AAC AAC GGT ATG TCC TTG GAG TGG ATA GGG TCT ATC GAC CCG TAT TAT
GGG GAC ACA AAA TAC GCG CAG AAA TTC AAG GGG AAG GCC ACC CTG ACC
GTA GAT AAA GCT AGT TCT ACT GCG TAC TTG CAA CTG AAA AGC CTC ACT
TCT GAG GAC TCT GCC GTC TAC TAC TGT GCT CGG CGA ATG ATA ACG ACG
GGG GAC TGG TAT TTC GAT GTT TGG GGT ACA GGG ACT ACG GTG ACT GTC
AGT AGC tccgga CD5-34H2L-3052 CAR (SEQ ID NO: 11)
ggatccGAGGTTAAACTCGTGGAGAGCGGTGCCGAACTCGTCCGAAGTGGTGCTTC
CGTTAAACTCAGTTGTGCCGCGTCAGGATTTAACATAAAAGATTACTACATTCAC
TGGGTCAAACAGCGCCCGGAGCAGGGGCTTGAATGGATCGGTGGATTGATCCT
GAAAACGGGCGCACCGAATATGCTCCCAAGTTCCAGGGCAAAGCTACTATGACC
GCTGACACCTCTAGTAACACTGCCTACCTGCAGTTGAGCTCTCTTACGTCTGAGG
ATACCGCTGTGTACTACTGTAATAACGGAAATTATGTACGACACTATTACTTCGA
CTACTGGGGGCAGGGCACTACTGTGACTGTATCTAGCggtggcggagggagcggcggtggagg
aagcggaggcggaggttccGATTGGCTCACACAATCCCCTGCAATCCTGAGTGCATCTCCA
GGCGAGAAAGTAACTATGACTTGCAGAGCTATAAGCTCTGTGTCCTACATGCACT
GGTATCAGCAGAAGCCAGGTTCTTCCCCGAAGCCGTGGATATATGCTACAAGCA
ATTTGGCATCCGGTGTTCCCGCCCGGTTTAGTGGCTCCGGTTCTGGGACAAGTTA -continued
```
CTCCCTCACGATCAGCAGGGTTGAAGCCGAGGACGCTGCCACTTACTATTGCCA
ACAGTGGTCAAGTAACCCCAGGACTTTCGGGGGAGGAACTAAACTTGAAATCAA
Atctaga
```

CD5-34L2H-3053 CAR (SEQ ID NO: 12)
```
Ggatcc GAT TGG CTC ACA CAA TCC CCT GCA ATC CTG AGT GCA TCT CCA GGC
GAG AAA GTA ACT ATG ACT TGC AGA GCT ATA AGC TCT GTG TCC TAC ATG
CAC TGG TAT CAG CAG AAG CCA GGT TCT TCC CCG AAG CCG TGG ATA TAT
GCT ACA AGC AAT TTG GCA TCC GGT GTT CCC GCC CGG TTT AGT GGC TCC
GGT TCT GGG ACA AGT TAC TCC CTC ACG ATC AGC AGG GTT GAA GCC GAG
GAC GCT GCC ACT TAC TAT TGC CAA CAG TGG TCA AGT AAC CCC AGG ACT
TTC GGG GGA GGA ACT AAA CTT GAA ATC AAA
Ggtggcggagggagcggcggtggaggaagcggaggcggaggttcc GAG GTT AAA CTC GTG GAG AGC
GGT GCC GAA CTC GTC CGA AGT GGT GCT TCC GTT AAA CTC AGT TGT GCC
GCG TCA GGA TTT AAC ATA AAA GAT TAC TAC ATT CAC TGG GTC AAA CAG
CGC CCG GAG CAG GGG CTT GAA TGG ATC GGG TGG ATT GAT CCT GAA AAC
GGG CGC ACC GAA TAT GCT CCC AAG TTC CAG GGC AAA GCT ACT ATG ACC
GCT GAC ACC TCT AGT AAC ACT GCC TAC CTG CAG TTG AGC TCT CTT ACG
TCT GAG GAT ACC GCT GTG TAC TAC TGT AAT AAC GGA AAT TAT GTA CGA
CAC TAT TAC TTC GAC TAC TGG GGG CAG GGC ACT ACT GTG ACT GTA TCT
AGC tCTAGA
```

CD5-17H2L-3054 CAR (SEQ ID NO: 13)
```
ggatccGAGGTCCAACTCGTAGAATCAGGTCCCGGATTGGTGCAACCATCCCAGAG
CCTCTCTATTACATGCACGGTCTCTGGATTTAGTCTGACCAATTACGATGTGCATT
GGGTGCGCCAGTCTCCCGGCAAGGGGTTGGAATGGCTTGGCGTTATATGAACT
ACGGAAATACAGACTATAACGCCGCGTTTATCTCTCGGCTGAGTATACGGAAAG
ACAGTAGTAAATCCCAGGTCTTTTTTACGATGTCATCCCTGCAAACGCCAGATAC
CGCAATATATTACTGCGCCAGGAACCACGGTGATGGTTATTATAATTGGTACTTC
GATGTGTGGGGTACTGGCACTACAGTCACAGTATCTTCAggtggcggagggagcggcggtgg
aggaagcggaggcggaggttccAACATTGTACTGACGCAAAGCCCCTCATCTTTGTCTGAGT
CACTCGGCGGCAAAGTAACCATCACATGCAAGGCCAGTCAAGACATCAATAAAT
ATATTGCTTGGTATCAGTATAAACCCGGCAAGGGGCCGCGACTGCTGATTCACTA
CACGAGTACCTTGCAACCGGGCATTCCGAGCCGATTTAGTGGCAGTGGCTCAGG
TCGCGATTACTCATTCTCAATAAGTAATCTCGAACCGGAAGACATAGCTACTTAT
TATTGCTTGCAGTACGATAATTTGTGGACCTTCGGGGGTGGTACAAAGTTGGAAA
TAAAGtctaga
```

CD8 Transmembrane domain nucleic acid sequence (SEQ ID NO: 14):
```
atctacatct gggcgcccct ggccgggact tgtggggtcc ttctcctgtc actggttatc
accctttact gc
```

CD8 Transmembrane domain amino acid sequence (SEQ ID NO: 15):
IYIWAPLAGTCGVLLLSLVITLYC CD8 hinge domain nucleic acid sequence (SEQ ID NO: 16):
```
accacgacgc cagcgccgcg accaccaaca ccggcgccca ccatcgcgtc gcagcccctg
tccctgcgcc cagaggcgtg ccggccagcg gcggggggcg cagtgcacac gagggggctg
gacttcgcct gtgat
```

CD8 hinge domain amino acid sequence (SEQ ID NO: 17):
TTTPAPRPPTPAPTIASQPLSLRPEACRPAAGGAVHTRGLDFACD 4-1BB nucleic acid sequence (SEQ ID NO: 18)
```
aaacggggca gaaagaaact cctgtatata ttcaaacaac catttatgag accagtacaa
actactcaag aggaagatgg ctgtagctgc cgatttccaa agaagaaga aggaggatgt
gaactg
```

CD3-zeta nucleic acid sequence (SEQ ID NO: 19)
```
agagtgaagt tcagcaggag cgcagacgcc cccgcgtaca agcagggcca gaaccagctc
tataacgagc tcaatctagg acgaagagag gagtacgatg ttttggacaa gagacgtggc
cgggaccctg agatgggggg aaagccgaga aggaagaacc ctcaggaagg cctgtacaat
gaactgcaga agataagat ggcggaggcc tacagtgaga ttgggatgaa aggcgagcgc
cggaggggca aggggcacga tggcctttac caggtctca gtacagccac caaggacacc
tacgacgccc ttcacatgca ggccctgccc cctcgc
```

4-1BB amino acid sequence (SEQ ID NO: 20):
KRGRKKLLYIFKQPFMRPVQTTQEEDGCSCRFPEEEEGGCEL CD3-zeta amino acid sequence (SEQ ID NO: 21):
RVKFSRSADAPAYKQGQNQLYNELNLGRREEYDVLDKRRGRDPEMGGKPRRKNPQ
EGLYNELQKDKMAEAYSEIGMKGERRRGKGHDGLYQGLSTATKDTYDALHMQAL
PPR CD2-MEDI507H2L-3028 CAR amino acid sequence (SEQ ID NO: 25)
MALPVTALLLPLALLLHAARPGSQVQLVQSGAEVQRPGASVKVSCKASGYIFTEYY
MYWVRQAPGQGLELVGRIDPEDGSIDYVEKFKKKVTLTADTSSSTAYMELSSLTSD
DTAVYYCARGKFNYRFAYWGQGTLVTVSSGGGGSGGGGSGGGGSDVVMTQSPPSL
LVTLGQPASISCRSSQSLLHSSGNTYLNWLLQRPGQSPQPLIYLVSKLESGVPDRFSGS
GSGTDFTLKISGVEAEDVGVYYCMQFTHYPYTFGQGTKLEIKSGTTTPAPRPPTPAPT
IASQPLSLRPEACRPAAGGAVHTRGLDFACDIYIWAPLAGTCGVLLLSLVITLYCKRG

```
RKKLLYIFKQPFMRPVQTTQEEDGCSCRFPEEEEGGCELRVKFSRSADAPAYKQGQN
QLYNELNLGRREEYDVLDKRRGRDPEMGGKPRRKNPQEGLYNELQKDKMAEAYSE
IGMKGERRRGKHDGLYQGLSTATKDTYDALHMQALPPR

CD2-MEDI507L2H-3043 CAR amino acid sequence (SEQ ID NO: 26)
MALPVTALLLPLALLLHAARPGSDVVMTQSPPSLLVTLGQPASISCRSSQSLLHSSGN
TYLNWLLQRPGQSPQPLIYLVSKLESGVPDRFSGSGSGTDFTLKISGVEAEDVGVYY
CMQFTHYPYTFGQGTKLEIKGGGGSGGGGSGGGGSQVQLVQSGAEVQRPGASVKV
SCKASGYIFTEYYMYWVRQAPGQGLELVGRIDPEDGSIDYVEKFKKKVTLTADTSSS
TAYMELSSLTSDDTAVYYCARGKFNYRFAYWGQGTLVTVSSSGTTTPAPRPPTPAPT
IASQPLSLRPEACRPAAGGAVHTRGLDFACDIYIWAPLAGTCGVLLLSLVITLYCKRG
RKKLLYIFKQPFMRPVQTTQEEDGCSCRFPEEEEGGCELRVKFSRSADAPAYKQGQN
QLYNELNLGRREEYDVLDKRRGRDPEMGGKPRRKNPQEGLYNELQKDKMAEAYSE
IGMKGERRRGKHDGLYQGLSTATKDTYDALHMQALPPR CD2-MEDI507H2L-3028 scFv amino acid sequence (SEQ ID NO: 27)
GSQVQLVQSGAEVQRPGASVKVSCKASGYIFTEYYMYWVRQAPGQGLELVGRIDPE
DGSIDYVEKFKKKVTLTADTSSSTAYMELSSLTSDDTAVYYCARGKFNYRFAYWGQ
GTLVTVSSGGGGSGGGGSGGGGSDVVMTQSPPSLLVTLGQPASISCRSSQSLLHSSG
NTYLNWLLQRPGQSPQPLIYLVSKLESGVPDRFSGSGSGTDFTLKISGVEAEDVGVY
YCMQFTHYPYTFGQGTKLEIKSG CD2-MEDI507L2H-3043 scFv amino acid sequence (SEQ ID NO: 28)
GSDVVMTQSPPSLLVTLGQPASISCRSSQSLLHSSGNTYLNWLLQRPGQSPQPLIYLV
SKLESGVPDRFSGSGSGTDFTLKISGVEAEDVGVYYCMQFTHYPYTFGQGTKLEIKG
GGGSGGGGSGGGGSQVQLVQSGAEVQRPGASVKVSCKASGYIFTEYYMYWVRQAP
GQGLELVGRIDPEDGSIDYVEKFKKKVTLTADTSSSTAYMELSSLTSDDTAVYYCAR
GKFNYRFAYWGQGTLVTVSSSG CD2-MEDI507 VH amino acid sequence (SEQ ID NO: 29)
QVQLVQSGAEVQRPGASVKVSCKASGYIFTEYYMYWVRQAPGQGLELVGRIDPED
GSIDYVEKFKKKVTLTADTSSSTAYMELSSLTSDDTAVYYCARGKFNYRFAYWGQG
TLVTVSS CD2-MEDI507 VL amino acid sequence (SEQ ID NO: 30)
DVVMTQSPPSLLVTLGQPASISCRSSQSLLHSSGNTYLNWLLQRPGQSPQPLIYLVSK
LESGVPDRFSGSGSGTDFTLKISGVEAEDVGVYYCMQFTHYPYTFGQGTKLEIK

CD2-MEDI507 HCDR1 (SEQ ID NO: 31)
EYYMY

CD2-MEDI507 HCDR2 (SEQ ID NO: 32)
RIDPEDGSIDYVEKFKK

CD2-MEDI507 HCDR3 (SEQ ID NO: 33)
GKFNYRFAY

CD2-MEDI507 LCDR1 (SEQ ID NO: 34)
RSSQSLLHSSGNTYLN

CD2-MEDI507 LCDR2 (SEQ ID NO: 35)
LVSKLES

CD2-MEDI507 LCDR3 (SEQ ID NO: 36)
MQFTHYPYT

CD2-OKT11H2L-3029 CAR amino acid sequence (SEQ ID NO: 37)
MALPVTALLLPLALLLHAARPGSQVQLQQPGAELVRPGTSVKLSCKASGYTFTSYW
MHWIKQRPEQGLEWIGRIDPYDSETHYNEKFKDKAILSVDKSSSTAYIQLSSLTSDDS
AVYYCSRRDAKYDGYALDYWGQGTTLTVSSGGGGSGGGGSGGGGSDIVMTQAAP
SVPVTPGESVSISCRSSKTLLHSNGNTYLYWFLQRPGQSPQVLIYRMSNLASGVPNRF
SGSGSETTFTLRISRVEAEDVGIYYCMQHLEYPYTFGGGTKLEIKSGTTTPAPRPPTPA
PTIASQPLSLRPEACRPAAGGAVHTRGLDFACDIYIWAPLAGTCGVLLLSLVITLYCK
RGRKKLLYIFKQPFMRPVQTTQEEDGCSCRFPEEEEGGCELRVKFSRSADAPAYKQG
QNQLYNELNLGRREEYDVLDKRRGRDPEMGGKPRRKNPQEGLYNELQKDKMAEA
YSEIGMKGERRRGKHDGLYQGLSTATKDTYDALHMQALPPR CD2-OKT11L2H-3030 CAR amino acid sequence (SEQ ID NO: 38)
MALPVTALLLPLALLLHAARPGSDIVMTQAAPSVPVTPGESVSISCRSSKTLLHSNGN
TYLYWFLQRPGQSPQVLIYRMSNLASGVPNRFSGSGSETTFTLRISRVEAEDVGIYYC
MQHLEYPYTFGGGTKLEIKGGGGSGGGGSGGGGSQVQLQQPGAELVRPGTSVKLSC
KASGYTFTSYWMHWIKQRPEQGLEWIGRIDPYDSETHYNEKFKDKAILSVDKSSSTA
YIQLSSLTSDDSAVYYCSRRDAKYDGYALDYWGQGTTLTVSSSGTTTPAPRPPTPAP
TIASQPLSLRPEACRPAAGGAVHTRGLDFACDIYIWAPLAGTCGVLLLSLVITLYCKR
GRKKLLYIFKQPFMRPVQTTQEEDGCSCRFPEEEEGGCELRVKFSRSADAPAYKQGQ
NQLYNELNLGRREEYDVLDKRRGRDPEMGGKPRRKNPQEGLYNELQKDKMAEAY
SEIGMKGERRRGKHDGLYQGLSTATKDTYDALHMQALPPR CD2-OKT11H2L-3029 scFv amino acid sequence (SEQ ID NO: 39)
GSQVQLQQPGAELVRPGTSVKLSCKASGYTFTSYWMHWIKQRPEQGLEWIGRIDPY
DSETHYNEKFKDKAILSVDKSSSTAYIQLSSLTSDDSAVYYCSRRDAKYDGYALDY
```

-continued
```
WGQGTTLTVSSGGGGSGGGGSGGGGSDIVMTQAAPSVPVTPGESVSISCRSSKTLLH
SNGNTYLYWFLQRPGQSPQVLIYRMSNLASGVPNRFSGSGSETTFTLRISRVEAEDV
GIYYCMQHLEYPYTFGGGTKLEIKSG CD2-OKT11L2H-3030 scFv amino acid sequence (SEQ ID NO: 40)
GSDIVMTQAAPSVPVTPGESVSISCRSSKTLLHSNGNTYLYWFLQRPGQSPQVLIYRM
SNLASGVPNRFSGSGSETTFTLRISRVEAEDVGIYYCMQHLEYPYTFGGGTKLEIKGG
GGSGGGGSGGGGSQVQLQQPGAELVRPGTSVKLSCKASGYTFTSYWMHWIKQRPE
QGLEWIGRIDPYDSETHYNEKFKDKAILSVDKSSSTAYIQLSSLTSDDSAVYYCSRRD
AKYDGYALDYWGQGTTLTVSSSG CD2-OKT11 VH amino acid sequence (SEQ ID NO: 41)
QVQLQQPGAELVRPGTSVKLSCKASGYTFTSYWMHWIKQRPEQGLEWIGRIDPYDS
ETHYNEKFKDKAILSVDKSSSTAYIQLSSLTSDDSAVYYCSRRDAKYDGYALDYWG
QGTTLTVSS CD2-OKT11 VL amino acid sequence (SEQ ID NO: 42)
DIVMTQAAPSVPVTPGESVSISCRSSKTLLHSNGNTYLYWFLQRPGQSPQVLIYRMSN
LASGVPNRFSGSGSETTFTLRISRVEAEDVGIYYCMQHLEYPYTFGGGTKLEIK

CD2-OKT11 HCDR1 (SEQ ID NO: 43)
SYWMH

CD2-OKT11 HCDR2 (SEQ ID NO: 44)
RIDPYDSETHYNEKFKD

CD2-OKT11 HCDR3 (SEQ ID NO: 45)
RDAKYDGYALDY

CD2-OKT11 LCDR1 (SEQ ID NO: 46)
RSSKTLLHSNGNTYLY

CD2-OKT11 LCDR2 (SEQ ID NO: 47)
RMSNLAS

CD2-OKT11 LCDR3 (SEQ ID NO: 48)
MQHLEYPYT

CD2-T11-2-H2L-3031 CAR amino acid sequence (SEQ ID NO: 49)
MALPVTALLLPLALLLHAARPGSQVQLQQPGAELVRPGASVKLSCKASGYTFTTFW
MNWVKQRPGQGLEWIGMIDPSDSEAHYNQMFKDKATLTVDKSSSTAYMQLSSLTS
EDSAVYYCARGRGYDDGDAMDYWGQGTSVTVSSGGGGSGGGGSGGGGSDIVMTQ
SPASLAVSLGQRATISYRASKSVSTSGYSYMHWNQQKPGQPPRLLIYLVSNLESGVP
ARFSGSGSGTDFTLNIHPVEEEDAATYYCMQFTHYPYTFGGGTKLEIKSGTTTPAPRP
PTPAPTIASQPLSLRPEACRPAAGGAVHTRGLDFACDIYIWAPLAGTCGVLLLSLVITL
YCKRGRKKLLYIFKQPFMRPVQTTQEEDGCSCRFPEEEEGGCELRVKFSRSADAPAY
KQGQNQLYNELNLGRREEYDVLDKRRGRDPEMGGKPRRKNPQEGLYNELQKDKM
AEAYSEIGMKGERRRGKGHDGLYQGLSTATKDTYDALHMQALPPR CD2-T11-2-H2L-3031 scFv amino acid sequence (SEQ ID NO: 50)
GSQVQLQQPGAELVRPGASVKLSCKASGYTFTTFWMNWVKQRPGQGLEWIGMIDP
SDSEAHYNQMFKDKATLTVDKSSSTAYMQLSSLTSEDSAVYYCARGRGYDDGDAM
DYWGQGTSVTVSSGGGGSGGGGSGGGGSDIVMTQSPASLAVSLGQRATISYRASKS
VSTSGYSYMHWNQQKPGQPPRLLIYLVSNLESGVPARFSGSGSGTDFTLNIHPVEEE
DAATYYCMQFTHYPYTFGGGTKLEIKSG CD2-T11-2-H2L-3031 VH amino acid sequence (SEQ ID NO: 51)
QVQLQQPGAELVRPGASVKLSCKASGYTFTTFWMNWVKQRPGQGLEWIGMIDPSD
SEAHYNQMFKDKATLTVDKSSSTAYMQLSSLTSEDSAVYYCARGRGYDDGDAMD
YWGQGTSVTVSS CD2-T11-2-H2L-3031 VL amino acid sequence (SEQ ID NO: 52)
DIVMTQSPASLAVSLGQRATISYRASKSVSTSGYSYMHWNQQKPGQPPRLLIYLVSN
LESGVPARFSGSGSGTDFTLNIHPVEEEDAATYYCMQFTHYPYTFGGGTKLEIK

CD2-T11-2 HCDR1 (SEQ ID NO: 53)
TFWMN

CD2-T11-2 HCDR2 (SEQ ID NO: 54)
MIDPSDSEAHYNQMFKD

CD2-T11-2 HCDR3 (SEQ ID NO: 55)
GRGYDDGDAMDY

CD2-T11-2 LCDR1 (SEQ ID NO: 56)
RASKSVSTSGYSYMH

CD2-T11-2 LCDR2 (SEQ ID NO: 57)
LVSNLES
```

CD2-T11-2 LCDR3 (SEQ ID NO: 58)
MQFTHYPYT

CD2-TS2-18.1.1-H2L-3032 CAR amino acid sequence (SEQ ID NO: 59)
MALPVTALLLPLALLLHAARPGSEVQLEESGGGLVMPGGSLKLSCAASGFAFSSYD
MSWVRQTPEKRLEWVAYISGGGFTYYPDTVKGRFTLSRDNAKNTLYLQMSSLKSE
DTAMYYCARQGANWELVYWGQGTTLTVSSGGGGSGGGGSGGGGSDIVMTQSPAT
LSVTPGDRVFLSCRASQSISDFLHWYQQKSHESPRLLIKYASQSISGIPSRFSGSGSGSD
FTLSINSVEPEDVGVYLCQNGHNFPPTFGGGTKLEIKSGTTTPAPRPPTPAPTIASQPLS
LRPEACRPAAGGAVHTRGLDFACDIYIWAPLAGTCGVLLLSLVITLYCKRGRKKLLY
IFKQPFMRPVQTTQEEDGCSCRFPEEEEGGCELRVKFSRSADAPAYKQGQNQLYNEL
NLGRREEYDVLDKRRGRDPEMGGKPRRKNPQEGLYNELQKDKMAEAYSEIGMKGE
RRRGKGHDGLYQGLSTATKDTYDALHMQALPPR CD2-TS2-18.1.1-L2H-3033 CAR amino acid sequence (SEQ ID NO: 60)
MALPVTALLLPLALLLHAARPGSDIVMTQSPATLSVTPGDRVFLSCRASQSISDFLHW
YQQKSHESPRLLIKYASQSISGIPSRFSGSGSGSDFTLSINSVEPEDVGVYLCQNGHNF
PPTFGGGTKLEIKGGGGSGGGGSGGGGSEVQLEESGGGLVMPGGSLKLSCAASGFA
FSSYDMSWVRQTPEKRLEWVAYISGGGFTYYPDTVKGRFTLSRDNAKNTLYLQMSS
LKSEDTAMYYCARQGANWELVYWGQGTTLTVSSSGTTTPAPRPPTPAPTIASQPLSL
RPEACRPAAGGAVHTRGLDFACDIYIWAPLAGTCGVLLLSLVITLYCKRGRKKLLYI
FKQPFMRPVQTTQEEDGCSCRFPEEEEGGCELRVKFSRSADAPAYKQGQNQLYNEL
NLGRREEYDVLDKRRGRDPEMGGKPRRKNPQEGLYNELQKDKMAEAYSEIGMKGE
RRRGKGHDGLYQGLSTATKDTYDALHMQALPPR CD2-TS2-18.1.1-H2L-3032 scFv amino acid sequence (SEQ ID NO: 61)
GSEVQLEESGGGLVMPGGSLKLSCAASGFAFSSYDMSWVRQTPEKRLEWVAYISGG
GFTYYPDTVKGRFTLSRDNAKNTLYLQMSSLKSEDTAMYYCARQGANWELVYWG
QGTTLTVSSGGGGSGGGGSGGGGSDIVMTQSPATLSVTPGDRVFLSCRASQSISDFL
HWYQQKSHESPRLLIKYASQSISGIPSRFSGSGSGSDFTLSINSVEPEDVGVYLCQNGH
NFPPTFGGGTKLEIKSG CD2-TS2-18.1.1-L2H-3033 scFv amino acid sequence (SEQ ID NO: 62)
GSDIVMTQSPATLSVTPGDRVFLSCRASQSISDFLHWYQQKSHESPRLLIKYASQSISG
IPSRFSGSGSGSDFTLSINSVEPEDVGVYLCQNGHNFPPTFGGGTKLEIKGGGGSGGG
GSGGGGSEVQLEESGGGLVMPGGSLKLSCAASGFAFSSYDMSWVRQTPEKRLEWV
AYISGGGFTYYPDTVKGRFTLSRDNAKNTLYLQMSSLKSEDTAMYYCARQGANWE
LVYWGQGTTLTVSSSG CD2-TS2-18.1.1 VH amino acid sequence (SEQ ID NO: 63)
EVQLEESGGGLVMPGGSLKLSCAASGFAFSSYDMSWVRQTPEKRLEWVAYISGGGF
TYYPDTVKGRFTLSRDNAKNTLYLQMSSLKSEDTAMYYCARQGANWELVYWGQG
TTLTVSS CD2-TS2-18.1.1 VL amino acid sequence (SEQ ID NO: 64)
DIVMTQSPATLSVTPGDRVFLSCRASQSISDFLHWYQQKSHESPRLLIKYASQSISGIP
SRFSGSGSGSDFTLSINSVEPEDVGVYLCQNGHNFPPTFGGGTKLEIK

CD2-TS2-18.1.1 HCDR1 (SEQ ID NO: 65)
SYDMS

CD2-TS2-18.1.1 HCDR2 (SEQ ID NO: 66)
YISGGGFTYYPDTVKG

CD2-TS2-18.1.1 HCDR3 (SEQ ID NO: 67)
QGANWELVY

CD2-TS2-18.1.1 LCDR1 (SEQ ID NO: 68)
RASQSISDFLH

CD2-TS2-18.1.1 LCDR2 (SEQ ID NO: 69)
YASQSIS

CD2-TS2-18.1.1 LCDR3 (SEQ ID NO: 70)
QNGHNFPPT

CD5-17L2H-3045 CAR amino acid sequence (SEQ ID NO: 71)
MALPVTALLLPLALLLHAARPGSNIVLTQSPSSLSESLGGKVTITCKASQDINKYIAW
YQYKPGKGPRLLIHYTSTLQPGIPSRFSGSGSGRDYSFSISNLEPEDIATYYCLQYDNL
WTFGGGTKLEIKGGGGSGGGGSGGGGSEVQLVESGPGLVQPSQSLSITCTVSGFSLT
NYDVHWVRQSPGKGLEWLGVIWNYGNTDYNAAFISRLSIRKDSSKSQVFFTMSSLQ
TPDTAIYYCARNHGDGYYNWYFDVWGTGTTVTVSSRTTTPAPRPPTPAPTIASQPL
SLRPEACRPAAGGAVHTRGLDFACDIYIWAPLAGTCGVLLLSLVITLYCHMKRGRK
KLLYIFKQPFMRPVQTTQEEDGCSCRFPEEEEGGCELTSRVKFSRSADAPAYQQGQN
QLYNELNLGRREEYDVLDKRRGRDPEMGGKPRRKNPQEGLYNELQKDKMAEAYSE
IGMKGERRRGKGHDGLYQGLSTATKDTYDALHMQALPPR CD5-17H2L-3054 CAR amino acid sequence (SEQ ID NO: 72)
MALPVTALLLPLALLLHAARPGSEVQLVESGPGLVQPSQSLSITCTVSGFSLTNYDVH
WVRQSPGKGLEWLGVIWNYGNTDYNAAFISRLSIRKDSSKSQVFFTMSSLQTPDTAI

```
-continued
YYCARNHGDGYYNWYFDVWGTGTTVTVSSGGGGSGGGGSGGGGSNIVLTQSPSSL
SESLGGKVTITCKASQDINKYIAWYQYKPGKGPRLLIHYTSTLQPGIPSRFSGSGSGR
DYSFSISNLEPEDIATYYCLQYDNLWTFGGGTKLEIKSRTTTPAPRPPTPAPTIASQPLS
LRPEACRPAAGGAVHTRGLDFACDIYIWAPLAGTCGVLLLSLVITLYCHMKRGRKK
LLYIFKQPFMRPVQTTQEEDGCSCRFPEEEEGGCELTSRVKFSRSADAPAYQQGQNQ
LYNELNLGRREEYDVLDKRRGRDPEMGGKPRRKNPQEGLYNELQKDKMAEAYSEI
GMKGERRRGKGHDGLYQGLSTATKDTYDALHMQALPPR CD5-17L2H-3045 scFv amino acid sequence (SEQ ID NO: 73)
NIVLTQSPSSLSESLGGKVTITCKASQDINKYIAWYQYKPGKGPRLLIHYTSTLQPGIP
SRFSGSGSGRDYSFSISNLEPEDIATYYCLQYDNLWTFGGGTKLEIKGGGGSGGGGS
GGGGSEVQLVESGPGLVQPSQSLSITCTVSGFSLTNYDVHWVRQSPGKGLEWLGVI
WNYGNTDYNAAFISRLSIRKDSSKSQVFFTMSSLQTPDTAIYYCARNHGDGYYNWY
FDVWGTGTTVTVSS CD5-17H2L-3054 scFv amino acid sequence (SEQ ID NO: 74)
EVQLVESGPGLVQPSQSLSITCTVSGFSLTNYDVHWVRQSPGKGLEWLGVIWNYGN
TDYNAAFISRLSIRKDSSKSQVFFTMSSLQTPDTAIYYCARNHGDGYYNWYFDVWG
TGTTVTVSSGGGGSGGGGSGGGGSNIVLTQSPSSLSESLGGKVTITCKASQDINKYIA
WYQYKPGKGPRLLIHYTSTLQPGIPSRFSGSGSGRDYSFSISNLEPEDIATYYCLQYDN
LWTFGGGTKLEIK CD5-17 VH amino acid sequence (SEQ ID NO: 75)
EVQLVESGPGLVQPSQSLSITCTVSGFSLTNYDVHWVRQSPGKGLEWLGVIWNYGN
TDYNAAFISRLSIRKDSSKSQVFFTMSSLQTPDTAIYYCARNHGDGYYNWYFDVWG
TGTTVTVSS CD5-17 VL amino acid sequence (SEQ ID NO: 76)
NIVLTQSPSSLSESLGGKVTITCKASQDINKYIAWYQYKPGKGPRLLIHYTSTLQPGIP
SRFSGSGSGRDYSFSISNLEPEDIATYYCLQYDNLWTFGGGTKLEIK CD5-9H2L-3048 CAR amino acid sequence (SEQ ID NO: 77)
MALPVTALLLPLALLLHAARPGSQVQLKESGPELEKPGASVKISCKASGYSFTAYSM
NWVKQNNGMSLEWIGSIDPYYGDTKYAQKFKGKATLTVDKASSTAYLQLKSLTSE
DSAVYYCARRMITTGDWYFDVWGTGTTVTVSSGGGGSGGGGSGGGGSHIVLTQSP
SSLSASLGDRVTISCRASQDISTYLNWYQQKPDGTVKLLIFYTSRLHAGVPSRFSGSG
SGTHHSLTISNLEQEDIATYFCQQGNSLPFTFGSGTKLEIKSGTTTPAPRPPTPAPTIAS
QPLSLRPEACRPAAGGAVHTRGLDFACDIYIWAPLAGTCGVLLLSLVITLYCKRGRK
KLLYIFKQPFMRPVQTTQEEDGCSCRFPEEEEGGCELRVKFSRSADAPAYKQGQNQL
YNELNLGRREEYDVLDKRRGRDPEMGGKPRRKNPQEGLYNELQKDKMAEAYSEIG
MKGERRRGKGHDGLYQGLSTATKDTYDALHMQALPPR CD5-9L2H-3049 CAR amino acid sequence (SEQ ID NO: 78)
MALPVTALLLPLALLLHAARPGSHIVLTQSPSSLSASLGDRVTISCRASQDISTYLNW
YQQKPDGTVKLLIFYTSRLHAGVPSRFSGSGSGTHHSLTISNLEQEDIATYFCQQGNS
LPFTFGSGTKLEIKGGGGSGGGGSGGGGSQVQLKESGPELEKPGASVKISCKASGYSF
TAYSMNWVKQNNGMSLEWIGSIDPYYGDTKYAQKFKGKATLTVDKASSTAYLQLK
SLTSEDSAVYYCARRMITTGDWYFDVWGTGTTVTVSSSGTTTPAPRPPTPAPTIASQP
LSLRPEACRPAAGGAVHTRGLDFACDIYIWAPLAGTCGVLLLSLVITLYCKRGRKKL
LYIFKQPFMRPVQTTQEEDGCSCRFPEEEEGGCELRVKFSRSADAPAYKQGQNQLYN
ELNLGRREEYDVLDKRRGRDPEMGGKPRRKNPQEGLYNELQKDKMAEAYSEIGMK
GERRRGKGHDGLYQGLSTATKDTYDALHMQALPPR CD5-9H2L-3048 scFv amino acid sequence (SEQ ID NO: 79)
GSQVQLKESGPELEKPGASVKISCKASGYSFTAYSMNWVKQNNGMSLEWIGSIDPY
YGDTKYAQKFKGKATLTVDKASSTAYLQLKSLTSEDSAVYYCARRMITTGDWYFD
VWGTGTTVTVSSGGGGSGGGGSGGGGSHIVLTQSPSSLSASLGDRVTISCRASQDIST
YLNWYQQKPDGTVKLLIFYTSRLHAGVPSRFSGSGSGTHHSLTISNLEQEDIATYFCQ
QGNSLPFTFGSGTKLEIKSG CD5-9L2H-3049 scFv amino acid sequence (SEQ ID NO: 80)
HIVLTQSPSSLSASLGDRVTISCRASQDISTYLNWYQQKPDGTVKLLIFYTSRLHAGV
PSRFSGSGSGTHHSLTISNLEQEDIATYFCQQGNSLPFTFGSGTKLEIKGGGGSGGGGS
GGGGSQVQLKESGPELEKPGASVKISCKASGYSFTAYSMNWVKQNNGMSLEWIGSI
DPYYGDTKYAQKFKGKATLTVDKASSTAYLQLKSLTSEDSAVYYCARRMITTGDW
YFDVWGTGTTVTVSS CD5-9 VH amino acid sequence (SEQ ID NO: 81)
QVQLKESGPELEKPGASVKISCKASGYSFTAYSMNWVKQNNGMSLEWIGSIDPYYG
DTKYAQKFKGKATLTVDKASSTAYLQLKSLTSEDSAVYYCARRMITTGDWYFDVW
GTGTTVTVSS CD5-9 VL amino acid sequence (SEQ ID NO: 82)
HIVLTQSPSSLSASLGDRVTISCRASQDISTYLNWYQQKPDGTVKLLIFYTSRLHAGV
PSRFSGSGSGTHHSLTISNLEQEDIATYFCQQGNSLPFTFGSGTKLEIK

CD5-9 HCDR1 (SEQ ID NO: 83)
AYSMN

CD5-9 HCDR2 (SEQ ID NO: 84)
SIDPYYGDTKYAQKFKG
```

-continued

CD5-9 HCDR3 (SEQ ID NO: 85)
RMITTGDWYFDV

CD5-9 LCDR1 (SEQ ID NO: 86)
RASQDISTYLN

CD5-9 LCDR2 (SEQ ID NO: 87)
YTSRLHA

CD5-9 LCDR3 (SEQ ID NO: 88)
QQGNSLPFT

CD5-34H2L-3052 CAR amino acid sequence (SEQ ID NO: 89)
MALPVTALLLPLALLLHAARPGSEVKLVESGAELVRSGASVKLSCAASGFNIKDYYI
HWVKQRPEQGLEWIGWIDPENGRTEYAPKFQGKATMTADTSSNTAYLQLSSLTSED
TAVYYCNNGNYVRHYYFDYWGQGTTVTVSSGGGGSGGGGSGGGGSDWLTQSPAI
LSASPGEKVTMTCRAISSVSYMHWYQQKPGSSPKPWIYATSNLASGVPARFSGSGSG
TSYSLTISRVEAEDAATYYCQQWSSNPRTFGGGTKLEIKSRTTTPAPRPPTPAPTIASQ
PLSLRPEACRPAAGGAVHTRGLDFACDIYIWAPLAGTCGVLLLSLVITLYCHMKRGR
KKLLYIFKQPFMRPVQTTQEEDGCSCRFPEEEEGGCELTSRVKFSRSADAPAYQQGQ
NQLYNELNLGRREEYDVLDKRRGRDPEMGGKPRRKNPQEGLYNELQKDKMAEAY
SEIGMKGERRRGKGHDGLYQGLSTATKDTYDALHMQALPPR CD5-34L2H-3053 CAR amino acid sequence (SEQ ID NO: 90)
MALPVTALLLPLALLLHAARPGSDWLTQSPAILSASPGEKVTMTCRAISSVSYMHW
YQQKPGSSPKPWIYATSNLASGVPARFSGSGSGTSYSLTISRVEAEDAATYYCQQWS
SNPRTFGGGTKLEIKGGGGSGGGGSGGGGSEVKLVESGAELVRSGASVKLSCAASG
FNIKDYYIHWVKQRPEQGLEWIGWIDPENGRTEYAPKFQGKATMTADTSSNTAYLQ
LSSLTSEDTAVYYCNNGNYVRHYYFDYWGQGTTVTVSSSRTTTPAPRPPTPAPTIAS
QPLSLRPEACRPAAGGAVHTRGLDFACDIYIWAPLAGTCGVLLLSLVITLYCHMKRG
RKKLLYIFKQPFMRPVQTTQEEDGCSCRFPEEEEGGCELTSRVKFSRSADAPAYQQG
QNQLYNELNLGRREEYDVLDKRRGRDPEMGGKPRRKNPQEGLYNELQKDKMAEA
YSEIGMKGERRRGKGHDGLYQGLSTATKDTYDALHMQALPPR CD5-34H2L-3052 scFv amino acid sequence (SEQ ID NO: 91)
EVKLVESGAELVRSGASVKLSCAASGFNIKDYYIHWVKQRPEQGLEWIGWIDPENG
RTEYAPKFQGKATMTADTSSNTAYLQLSSLTSEDTAVYYCNNGNYVRHYYFDYW
QGTTVTVSSGGGGSGGGGSGGGGSDWLTQSPAILSASPGEKVTMTCRAISSVSYMH
WYQQKPGSSPKPWIYATSNLASGVPARFSGSGSGTSYSLTISRVEAEDAATYYCQQ
WSSNPRTFGGGTKLEIK CD5-34L2H-3053 scFv amino acid sequence (SEQ ID NO: 92)
DWLTQSPAILSASPGEKVTMTCRAISSVSYMHWYQQKPGSSPKPWIYATSNLASGVP
ARFSGSGSGTSYSLTISRVEAEDAATYYCQQWSSNPRTFGGGTKLEIKGGGGSGGGG
SGGGGSEVKLVESGAELVRSGASVKLSCAASGFNIKDYYIHWVKQRPEQGLEWIGW
IDPENGRTEYAPKFQGKATMTADTSSNTAYLQLSSLTSEDTAVYYCNNGNYVRHYY
FDYWGQGTTVTVSS CD5-34 VH amino acid sequence (SEQ ID NO: 93)
EVKLVESGAELVRSGASVKLSCAASGFNIKDYYIHWVKQRPEQGLEWIGWIDPENG
RTEYAPKFQGKATMTADTSSNTAYLQLSSLTSEDTAVYYCNNGNYVRHYYFDYWG
QGTTVTVSS CD5-34 VL amino acid sequence (SEQ ID NO: 94)
DWLTQSPAILSASPGEKVTMTCRAISSVSYMHWYQQKPGSSPKPWIYATSNLASGVP
ARFSGSGSGTSYSLTISRVEAEDAATYYCQQWSSNPRTFGGGTKLEIKSR

CD5-34 HCDR1 (SEQ ID NO: 95)
DYYIH

CD5-34 HCDR2 (SEQ ID NO: 96)
WIDPENGRTEYAPKFQG

CD5-34 HCDR3 (SEQ ID NO: 97)
GNYVRHYYFDY

CD5-34 LCDR1 (SEQ ID NO: 98)
RAISSVSYMH

CD5-34 LCDR2 (SEQ ID NO: 99)
ATSNLAS

CD5-34 LCDR3 (SEQ ID NO: 100)
QQWSSNPRT

CRISPR/Cas

Certain embodiments of the invention include cells that have been modified by a CRISPR/Cas system. CRISPR/Cas systems include, but are not limited to, the CRISPR/Cas9 system and the CRISPR/Cpf1 system. In certain embodiments, the invention includes cells that have been modified using the CRISPR/Cas9 system. In certain embodiments, the modifications include knocking-out or mutating an endogenous gene, e.g. CD2, CD5, or CD7.

The CRISPR/Cas9 system is a facile and efficient system for inducing targeted genetic alterations. Target recognition by the Cas9 protein requires a 'seed' sequence within the guide RNA (gRNA or sgRNA) and a conserved tri-nucleotide containing protospacer adjacent motif (PAM) sequence upstream of the gRNA-binding region. The CRISPR/Cas9 system can thereby be engineered to cleave virtually any DNA sequence by redesigning the gRNA for use in cell lines (such as 293T cells), primary cells, and CAR T cells. The CRISPR/Cas system can simultaneously target multiple genomic loci by co-expressing a single Cas9 protein with two or more gRNAs, making this system uniquely suited for multiple gene editing or synergistic activation of target genes.

One example of a CRISPR/Cas system used to inhibit gene expression, CRISPRi, is described in U.S. Publication No. US2014/0068797, which is incorporated herein by reference in its entirety. CRISPRi induces permanent gene disruption that utilizes the RNA-guided Cas9 endonuclease to introduce DNA double stranded breaks which trigger error-prone repair pathways to result in frame shift mutations. A catalytically dead Cas9 lacks endonuclease activity. When coexpressed with a guide RNA, a DNA recognition complex is generated that specifically interferes with transcriptional elongation, RNA polymerase binding, or transcription factor binding. This CRISPRi system efficiently represses expression of targeted genes.

CRISPR/Cas gene disruption occurs when a guide nucleic acid sequence specific for a target gene and a Cas endonuclease are introduced into a cell and form a complex that enables the Cas endonuclease to introduce a double strand break at the target gene. In certain embodiments, the CRISPR system comprises an expression vector, such as, but not limited to, an pAd5F35-CRISPR vector. In other embodiments, the Cas expression vector induces expression of Cas9 endonuclease. Other endonucleases may also be used, including but not limited to Cpf1, T7, Cas3, Cas8a, Cas8b, Cas10d, Cse1, Csy1, Csn2, Cas4, Cas10, Csm2, Cmr5, Fok1, other nucleases known in the art, and any combination thereof.

In certain embodiments, inducing the Cas expression vector comprises exposing the cell to an agent that activates an inducible promoter in the Cas expression vector. In such embodiments, the Cas expression vector includes an inducible promoter, such as one that is inducible by exposure to an antibiotic (e.g., by tetracycline or a derivative of tetracycline, for example doxycycline). However, it should be appreciated that other inducible promoters can be used. The inducing agent can be a selective condition (e.g., exposure to an agent, for example an antibiotic) that results in induction of the inducible promoter. This results in expression of the Cas expression vector.

The guide nucleic acid sequence is specific for a gene and targets that gene for Cas endonuclease-induced double strand breaks. The sequence of the guide nucleic acid sequence may be within a loci of the gene. In one embodiment, the guide nucleic acid sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40 or more nucleotides in length.

The guide nucleic acid sequence may be specific for any gene, e.g. CD2, CD5, CD7. The guide nucleic acid sequence includes a RNA sequence, a DNA sequence, a combination thereof (a RNA-DNA combination sequence), or a sequence with synthetic nucleotides. The guide nucleic acid sequence can be a single molecule or a double molecule. In one embodiment, the guide nucleic acid sequence comprises a single guide RNA.

In the context of formation of a CRISPR complex, "target sequence" refers to a sequence to which a guide sequence is designed to have some complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In certain embodiments, a target sequence is located in the nucleus or cytoplasm of a cell. In other embodiments, the target sequence may be within an organelle of a eukaryotic cell, for example, mitochondrion or nucleus. Typically, in the context of an endogenous CRISPR system, formation of a CRISPR complex (comprising a guide sequence hybridized to a target sequence and complexed with one or more Cas proteins) results in cleavage of one or both strands in or near (e.g., within about 1, 2, 3, 4, 5, 6, 7, 8, 9, 10, 20, 50 or more base pairs) the target sequence. As with the target sequence, it is believed that complete complementarity is not needed, provided this is sufficient to be functional. In certain embodiments, the tracr sequence has at least 50%, 60%, 70%, 80%, 90%, 95% or 99% of sequence complementarity along the length of the tracr mate sequence when optimally aligned.

In other embodiments, one or more vectors driving expression of one or more elements of a CRISPR system are introduced into a host cell, such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In certain embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron).

In certain embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Additional domains that may form part of a fusion protein comprising a CRISPR enzyme are described in US20110059502, incorporated herein by reference. In certain embodiments, a tagged CRISPR enzyme is used to identify the location of a target sequence.

Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Another delivery mode for the CRISPR/Cas9 comprises a combination of RNA and purified Cas9 protein in the form of a Cas9-guide RNA ribonucleoprotein (RNP) complex. (Lin et al., 2014, ELife 3:e04766). Viral vector delivery systems include DNA and RNA viruses, which have either episomal or integrated genomes after delivery to the cell (Anderson, 1992, Science 256:808-813; and Yu et al., 1994, Gene Therapy 1:13-26).

In certain embodiments, the CRISPR/Cas is derived from a type II CRISPR/Cas system. In other embodiments, the CRISPR/Cas system is derived from a Cas9 protein. The Cas9 protein can be from *Streptococcus pyogenes, Streptococcus thermophilus*, or other species. In certain embodiments, Cas9 can include: spCas9, Cpf1, CasY, CasX, or saCas9.

In general, CRISPR/Cas proteins comprise at least one RNA recognition and/or RNA binding domain. RNA recognition and/or RNA binding domains interact with the guiding RNA. CRISPR/Cas proteins can also comprise nuclease domains (i.e., DNase or RNase domains), DNA binding domains, helicase domains, RNAse domains, protein-protein interaction domains, dimerization domains, as well as other domains. The CRISPR/Cas proteins can be modified to increase nucleic acid binding affinity and/or specificity, alter an enzymatic activity, and/or change another property of the protein. In certain embodiments, the CRISPR/Cas-like protein of the fusion protein can be derived from a wild type Cas9 protein or fragment thereof. In other embodiments, the CRISPR/Cas can be derived from modified Cas9 protein. For example, the amino acid sequence of the Cas9 protein can be modified to alter one or more properties (e.g., nuclease activity, affinity, stability, and so forth) of the protein. Alternatively, domains of the Cas9 protein not involved in RNA-guided cleavage can be eliminated from the protein such that the modified Cas9 protein is smaller than the wild type Cas9 protein. In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-stranded break in DNA. (Jinek et al., 2012, Science, 337:816-821). In certain embodiments, the Cas9-derived protein can be modified to contain only one functional nuclease domain (either a RuvC-like or a HNH-like nuclease domain). For example, the Cas9-derived protein can be modified such that one of the nuclease domains is deleted or mutated such that it is no longer functional (i.e., the nuclease activity is absent). In some embodiments in which one of the nuclease domains is inactive, the Cas9-derived protein is able to introduce a nick into a double-stranded nucleic acid (such protein is termed a "nickase"), but not cleave the double-stranded DNA. In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

In one non-limiting embodiment, a vector drives the expression of the CRISPR system. The art is replete with suitable vectors that are useful in the present invention. The vectors to be used are suitable for replication and, optionally, integration in eukaryotic cells. Typical vectors contain transcription and translation terminators, initiation sequences, and promoters useful for regulation of the expression of the desired nucleic acid sequence. The vectors of the present invention may also be used for nucleic acid standard gene delivery protocols. Methods for gene delivery are known in the art (U.S. Pat. Nos. 5,399,346, 5,580,859 & 5,589,466, incorporated by reference herein in their entireties).

Further, the vector may be provided to a cell in the form of a viral vector. Viral vector technology is well known in the art and is described, for example, in Sambrook et al. (4$^{th}$ Edition, Molecular Cloning: A Laboratory Manual, Cold Spring Harbor Laboratory, New York, 2012), and in other virology and molecular biology manuals. Viruses, which are useful as vectors include, but are not limited to, retroviruses, adenoviruses, adeno-associated viruses, herpes viruses, Sindbis virus, gammaretrovirus and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

Introduction of Nucleic Acids

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Moreover, the nucleic acids may be introduced by any means, such as transducing the expanded T cells, transfecting the expanded T cells, and electroporating the expanded T cells. One nucleic acid may be introduced by one method and another nucleic acid may be introduced into the T cell by a different method.

RNA

In one embodiment, the nucleic acids introduced into the T cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a chimeric membrane protein. By way of example, the template encodes an antibody, a fragment of an antibody or a portion of an antibody. By way of another example, the template comprises an extracellular domain comprising a single chain variable domain of an antibody, such as anti-CD3, and an intracellular domain of a co-stimulatory molecule. In one embodiment, the template for the RNA chimeric membrane protein encodes a chimeric membrane protein comprising an extracellular domain comprising an antigen binding domain derived from an antibody to a co-stimulatory molecule, and an intracellular domain derived from a portion of an intracellular domain of CD28 and 4-1BB.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the RNA is electroporated into the cells, such as in vitro transcribed RNA.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct is delivered into the cells by electroporation. Sec, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171, 264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993, 434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

In certain embodiments, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° ° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

Expansion of T Cells

In certain embodiments, the T cells disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the electroporated population.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

Pharmaceutical Compositions

Pharmaceutical compositions of the present invention may comprise the modified cell or population of cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The cells of the invention to be administered may be autologous, allogeneic or xenogeneic with respect to the subject undergoing therapy.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It can generally be stated that a pharmaceutical composition comprising the modified T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the modified cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described.

| Target | gRNA ID | DNA seq | Position | Strand | Sequence | PAM | On |
|--------|---------|---------|----------|--------|----------|-----|------|
| CD2 | #8 | Ex3 | 116760612 | − | ACAGCTGACAGGCTCGACAC (SEQ ID NO: 22) | TGG | 63.4 |
| CD5 | #4 | Ex2-In2 | 61115090 | + | CGGCTCAGCTGGTATGACCC (SEQ ID NO: 23) | AGG | 66.7 |
| CD7 | #85 | Ex2 | 670 | − | GGAGCAGGTGATGTTGACGG (SEQ ID NO: 24) | AGG | 74.9 | sgRNAs were designed to target CD2, CD5, or CD7 (e.g. SEQ ID NOs: 22-24, respectively) and synthesized using the GeneArt Precision sgRNA synthesis kit. Cas9 expression plasmid (pGEM-Cas9) was amplified and linearized. Cas9 RNA was synthesized using the mMessage mMachine T7 Ultra kit. CRISPR editing was performed in Jurkat cells: CD2/CD5/CD7 sgRNAs and Cas9 were transfected into Jurkat cells by electroporation. Expression of CD2/CD5/

CD7 on Jurkat cells was detected by flow cytometry and the most effective CD2/CD5/CD7 sgRNAs were determined. CRISPR editing was then performed in primary human T cells using the most efficient CD2/CD5/CD7 sgRNA: the chosen sgRNA and Cas9 RNA were electroporated into primary human T cells. CD2/CD5/CD7 expression was detected on the primary human T cells by flow cytometry to validate the knock-out/editing efficiency.

Specifically, fresh CD4/CD8 T cells were obtained and incubated with dynabeads on day 0. On day 4, cells were de-beaded then electroporated with Cas9 and sgRNA. Conditioned media (TCM (X-vivo15, human serum 5%, Glutamine), IL-7 10 ng/ml, and IL-15 10 ng/ml) was added to the cells. On day 6, cells were transduced with CAR lentivirus. On day 9, CAR expression was assessed. Cells were fed to 0.8e6/ml and frozen when volume <300 fl (FIG. 22).

CAR constructs: All constructs were generated using the lentiviral pTRPE 4-1BB CD3zeta backbone. OKT11 CARs and TS2/18.1.1 CARs were constructed using scFvs from antibodies generated from hybridomas purchased from ATCC (ATCC® CRL-8027™ and ATCC® HB-195™, respectively). The T11-2 CAR was constructed using an scFv from an antibody generated from a hybridoma that was received from Ellis Reinherz. All CD5 CARs were constructed using scFvs from antibody sequences published in WO 2010/022737 A1, contents of which are incorporated by reference in their entirety herein.

The results of the experiments are now described.

Figure 1:
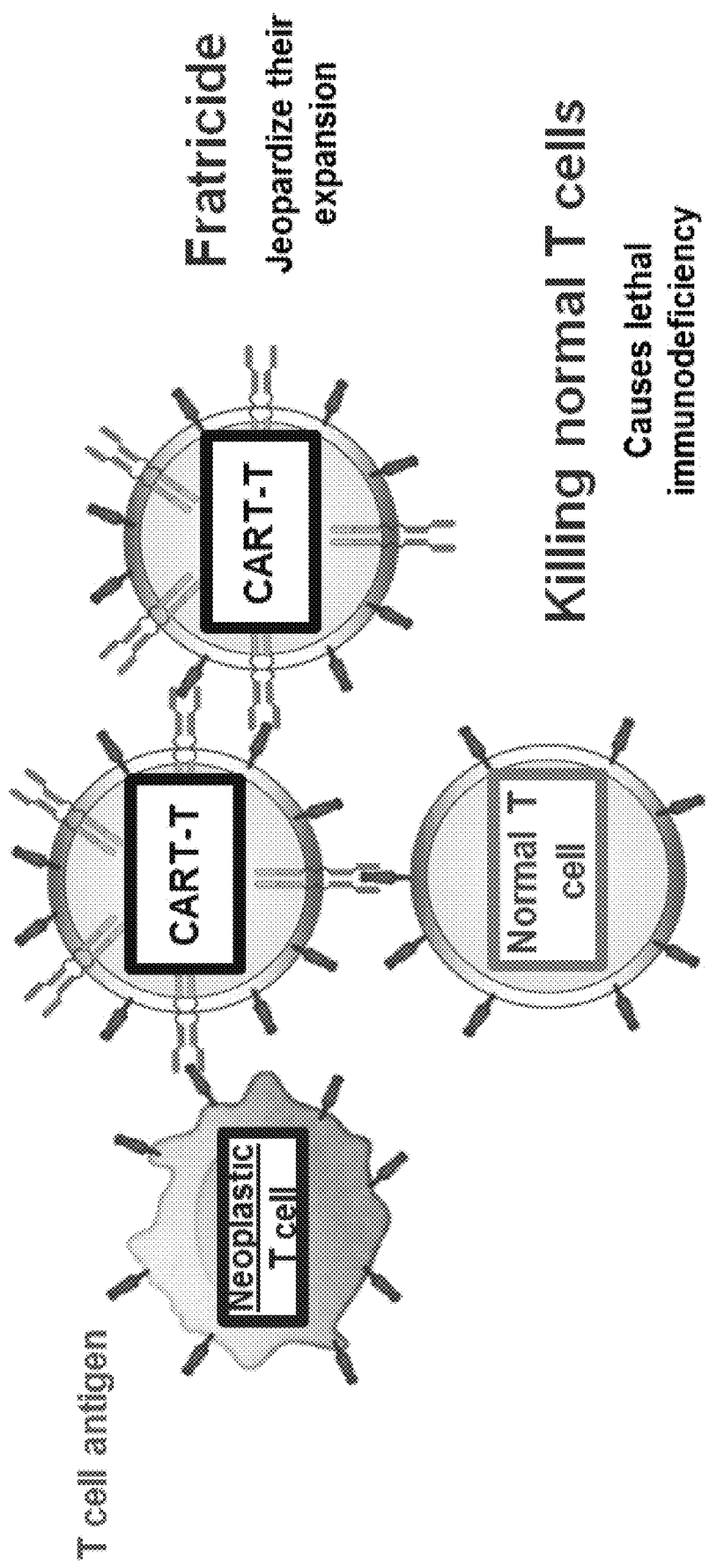
FIG. 1 is a schematic illustrating current issues with CART therapy for T cell neoplasms.
Figure 2:
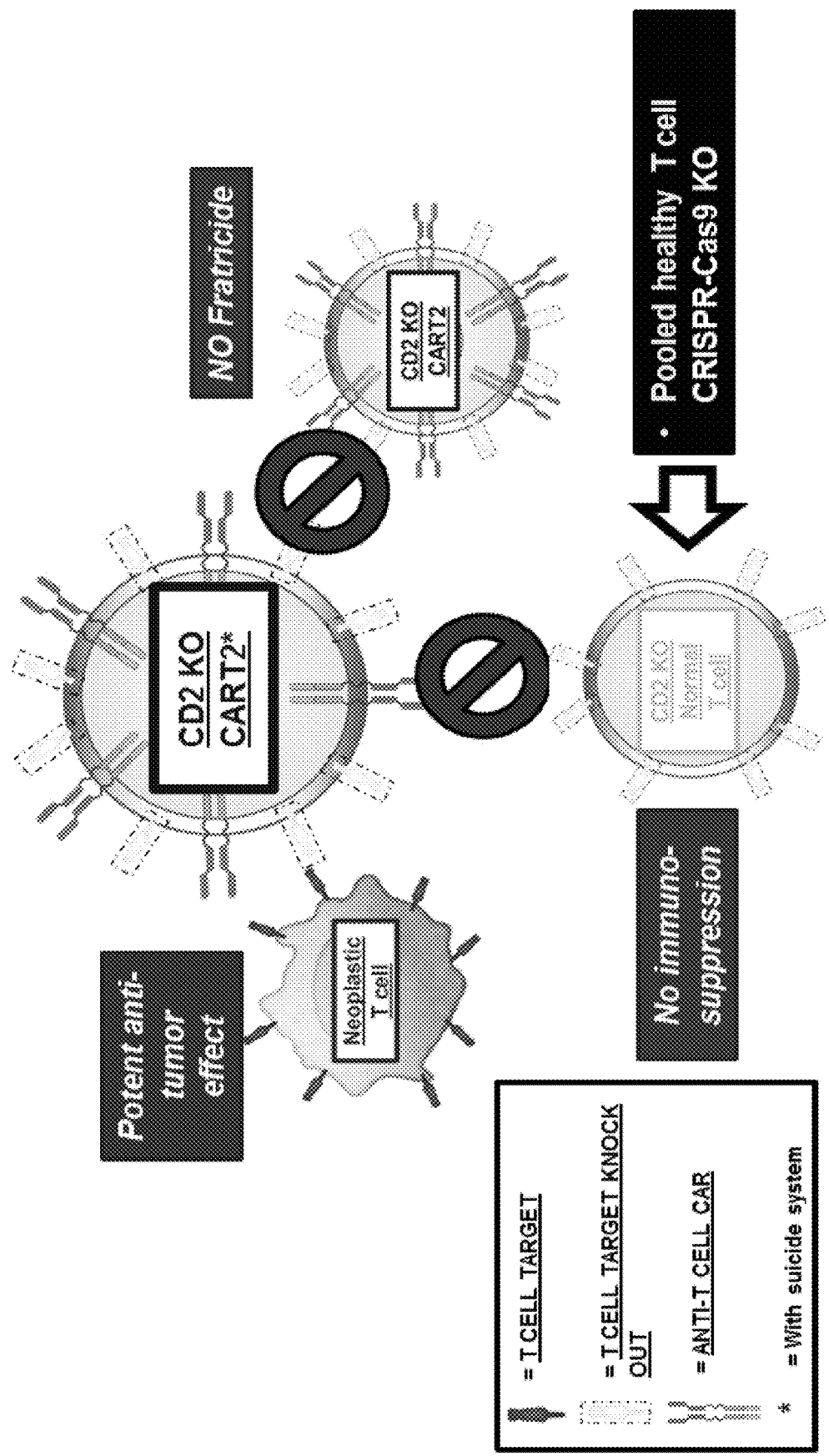
FIG. 2 is a schematic illustrating development of an innovative strategy where: i. a tumor target is removed from normal T cells using gene-editing and thereby avoids fratricide during manufacturing; ii. a second T cell product containing normal T cells wherein the T cell target is knocked-out (KO) that is co-infused with an anti-T cell neoplasm CART to provide T cell immunity that is not affected by CART killing.

Example 1: A Novel Approach to Target T Cell Lymphomas and Leukemias without Causing T Cell Toxicity T-cell lymphomas and leukemias have an overall very poor prognosis, and there are few therapeutic options available for these patients. Chimeric antigen receptor T cell (CART) immunotherapy has led to unprecedented results in CD19+B-cell non-Hodgkin lymphoma (B-NHL). Herein, another successful "CART19-like" product was designed to target T-NHL. As CD19 is not expressed in T-NHL, additional targets like CD2, CD5, CD7 and others were evaluated for CART therapy. However, all these targets are also expressed by normal T cells, leading to unacceptable clinical toxicity (T cell aplasia—immunodeficiency) (FIG. 1). Herein, a safe and effective CART strategy was developed for the treatment of T-cell lymphomas by editing the normal T cells to be resistant to CART killing (FIG. 2). CART therapy against T-cell lymphomas and leukemias was feasible when the CART target (CD2, CD5, CD7) was temporarily removed from normal T cells, thus avoiding CART-mediated killing and immunodeficiency (FIG. 2).

Example 2: Anti-CD5 CAR T Cells (CART5) and CD5 Knocked-Out (KO) Normal T Cells

Figure 3:
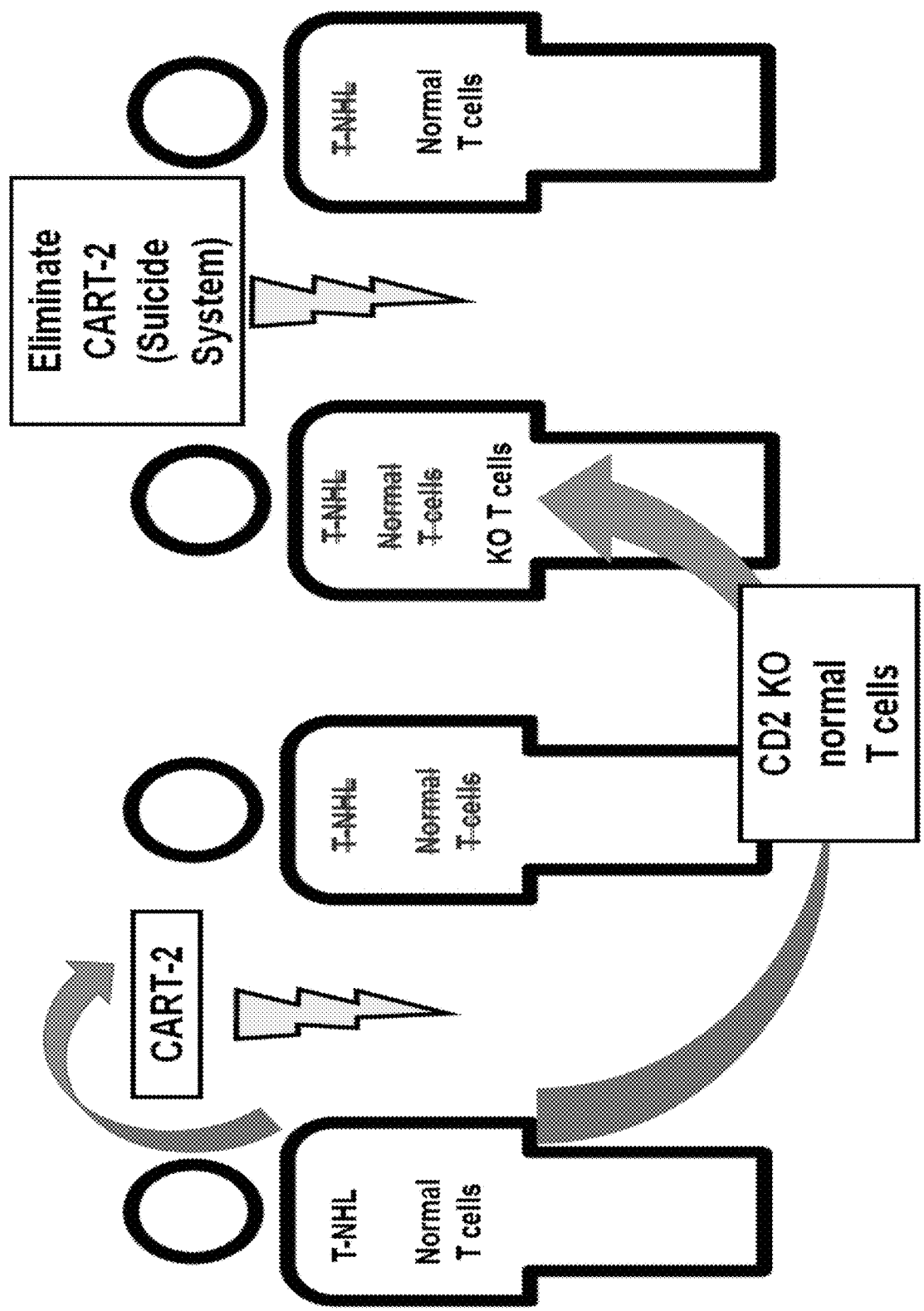
FIG. 3 is a schematic illustrating a novel approach to target T cell lymphomas without causing T cell toxicity. A two-pronged immunotherapy is used that includes anti-T-

A two-pronged immunotherapy is disclosed herein that includes anti-CD5 CAR T cells (CART5) and CD5 knocked-out (KO) normal T cells (FIG. 3). The CART5 destroys T cell lymphoma (e.g. T-NHL) or T cell leukemia cells but also kills normal T cells. The infusion of CD5 KO normal T cells provides CART-resistant T cell immunity until CART5 cells are depleted, in some cases by using a suicide gene (e.g. iCasp9, CD20/rituximab or others).

CD5 was selected as a T-NHL target due to high expression on T-NHL cells and absent expression in other tissues besides T cells and a minor B cell subset. Six anti-CD5 CAR constructs were generated using single-chain variable fragments (scFv) with different affinity (#17, #34, #9 with high, medium, low affinity respectively (Klitgaard J L, et al. (2013) *British journal of haematology* 163:182-93)) and expressed in T cells (FIGS. 4-5). Intriguingly, anti-CD5 CART did not require the knockout of CD5 to manufacture CART5 cells despite CD5 being expressed in 100% of CART cells (Mamonkin M, et. al. (2015) Blood 126:983-92), although CD5 expression was lower as compared to control T cells (FIG. 8). Without CRISPR-Cas9 KO of CD5, the CD5 mean fluorescence intensity (MFI) was 10 fold less in CART5 as compared to control T cells, while there was no change in another pan T-cell marker such as CD2 (FIG. 8).

In vitro and in vivo activity of the different CART5 constructs were compared. Construct C3054, which was derived from the high-affinity scFv #17, demonstrated the best in vivo killing. Jurkat cells were transduced with different CAR5 constructs (FIG. 13, targeted epitope and affinity shown to the left) and with a GFP-NFAT reporter then co-cultured with CD5+ tumor cells (or controls) for 24 hours. The lead CART5 (C3054) shows increased NFAT activation (FIG. 13).

The lead anti-CD5 CART was implemented using a suicide system, and its function was tested in vitro and in vivo. Without wishing to be bound by specific theory, removal of CD5 (CRISPR-Cas9 KO) further increases CART5 anti-tumor effect by eliminating the possible in cis surface interaction between CAR5 and CD5 on the CART5.

Insertion of a suicide system in the lead CART5 product: The lead candidate CART5 (C3054) products are engineered to express a suicide system (FIG. 26). A P2A bicistronic vector encoding for both the CAR5 and the inducible-caspase9 suicide system (Di Stasi A, et al. (2011) 365:1673-83) (iCART5) is developed. Both orientations are cloned, CAR5-P2A-iCasp9 and iCasp9-P2A-CAR5 (FIG. 26), to define the most efficient one (higher % double-expressing cells and lower % CAR5+ iCasp9—for safety). iCART5 is efficiently eliminated using the clinical-grade compound rimiducid (AP1903, Bellicum Pharmaceuticals).

In vitro testing of iCART5: The newly generated iCART5 is compared to WT CART5 to confirm their efficacy (in vitro luciferase-based killing) and phenotype/function upon antigen stimulation (CD5+ Jurkat T-leukemia cells) (flow cytometry phenotype, 30-plex cytokine analysis by Luminex assay, CFSE proliferation and CD107a degranulation). Importantly, in vitro depletion is tested by co-culturing iCART5 with different concentrations of rimiducid (0, 0.03, 0.3, 3, 10 nM) and checking killing at 15', 30' and at 2, 6, 12 and 24 hours. iCART5 is also tested against primary T-NHL cells using an established killing assay using primary CFSE-labelled Sezary cells.

In vivo testing of iCART5: In vivo xenograft models (Ruella M, et al. (2016) *J Clin Invest*) [using the click-beetle green (CBG)+T-leukemia cell line Jurkat cell line and click-beetle red (CBR)+ iCART5] are used to test the ability of rimiducid (50 ug/mouse 23) to deplete iCART5 vs. WT CART5 in vivo. NOD SCID gamma-deficient mice (NSG) mice (8 per group) are injected with $2\times10e^6$ CART5 cells/mouse. Tumor burden over time is assessed as bioluminescence (CBG) and T cell phenotype is studied by flow cytometry and expansion by bioluminescence (CBR) at multiple time points (hours/days). Mice are kept long-term (3-4 months) for survival and monitoring of relapse. A human T-NHL xenograft model was previously established by injecting primary Sezary cells i.v. This model is used to test the iCART5 for both anti-tumor and depletion efficacies.

Evaluation of the role of CD5 KO in CART5: Preliminary data demonstrated that CD5 CART5 are more effective than WT CART5 in vivo. CD5 is knocked out on CART5 cells using CRISPR-Cas9. The CRISPR-Cas9 CART expansion protocol was previously optimized. Wild-type CART5 is compared to CD5 KO CART5 in vitro by testing CART5 viability, antigen-driven proliferation (using CFSE labeling), cytokine production (by 30-plex Luminex), degranulation (CD107a assessment by flow cytometry), cytotoxicity (luciferase-based), and phenotype (memory subsets, Th1/Th2). Both cell lines (e.g., Jurkat) and primary samples are used as targets. In vivo comparison of CD5 KO vs. WT CART5 (1×10e6 cells/mouse) is performed in NSG mice bearing Jurkat and monitoring expansion and phenotype in the peripheral blood at day 10 and 14.

Mechanism of enhancement of CART5 function by CD5 KO: Having proven that CD5KO improves CART5 activity, additional studies are performed to understand the mechanism: i. confocal imaging to analyze the localization of CAR5 and CD5 on CART5 cells; ii. single-molecule imaging (ONI nanoimager) to prove that CAR5 binds in cis to CD5; iii. expressing CAR5 in CD5+ Jurkat and show that CART5 fail to kill CAR5+ Jurkat because the CD5 epitope is masked (by CAR5); and iv. as CD5 as an inhibitory role on T cell activation, we will study CART5 activation in the presence or not of CD5 (phospo-flow cytometry).

Generating CART-resistant normal T cells to avoid T cell aplasia: CART5 are unable to distinguish neoplastic versus normal T cells as both express similar levels of CD5. CART-resistant normal T cells are developed to be co-infused with the anti-T-NHL CART to ensure immunity during CART anti-tumor activity. CRISPR-Cas9 gene-editing is used to knock out CD5 in normal T cells thus making them invisible to CART5. A highly efficient CRISPR-Cas9 gRNA (#4) was generated that can KO ~95% of CD5 in normal T cells using an optimized CART expansion protocol. Data show that CD5 KO T cells were resistant to CART5 while WT T cells (CD5+) were potently killed within 24 hours.

Manufacturing of CD5 KO normal T cells: CD5 KO normal T cells are developed using a highly efficient gRNA (#4) that is electroporated together with Cas9 protein (ThermoFisher v2) using a Lonza 4D Nucleofector. CRISPR-Cas9 KO is performed on day 1, then cells are cultured at 30° C. for 2 days to increase gene-editing, then activated with anti-CD3/CD28 Dynabeads (beads:1 T cells) and expanded until they reach a cell volume <300 fl.

In vitro evaluation of CD5 KO normal T cell resistance to iCART5 killing: Resistance of CD5 KO normal T cells to CART5 is tested in vitro by performing killing assays (CFSE labeling of target T cells). Preliminary results showed that CD5 KO confers resistance. Three additional T cell donors will be tested.

In vivo evaluation of CD5 KO normal T cell resistance to iCART5 in an autologous xenograft model: NSG mice (8 mice/group) are engrafted with luciferase+CD5 KO normal T cells or WT, and after two days autologous iCART5 is injected. The effect of iCART5 on CD5 ko and WT normal T cells is assessed by bioluminescence. Once WT T cells are completely eliminated by iCART5 (luminescence) rimiducid is administered to deplete iCART5. Then WT T cells are reinjected to demonstrate that normal T cells can repopulate the host. Mice are bled weekly to assess CART expansion.

Evaluation of the role of CD5 KO on normal T cell functions: The role of CD5 KO is investigated in normal T cells by carefully studying T cell effector functions. After TCR-specific stimulation (anti-CD3/CD28 beads) cytokine production (30-plex Luminex), proliferation (CFSE) and activation of CD5KO T cells vs. WT are measured. Also tested are whether CD5KO T cells proliferate and produce similarly to WT when exposed to common infections.

Defining the optimal CD5KO normal T cell dose for clinical use: Using both in silico and experimental approaches (TCR sequencing and tetramer staining of TCRs specific for infectious agents) the minimum number of cells to be infused in relapsed or refractor (r/r) T-NHL patients is defined in order to ensure sufficient T cell immunity to the most common infections.

Testing the concurrent infusion of iCART5 and CD5 KO normal T cells in a phase 1 pilot clinical trial for patients with advanced T cell lymphoma: An Investigation New Drug (IND) package is developed and submitted to the FDA. A phase 1 clinical trial is started to test the anti-T-NHL CART approach in patients. The IND package is based on preliminary results and further data from experiments described herein.

Clinical trial protocol design: The phase 1 clinical trial includes patients with r/r T-NHL that are treated using a 3+3 protocol design. From a single apheresis, two products are generated using enriched T cells: #1. CRISPR-Cas9 CD5 KO normal T cells and #2. iCART5. The first product to be infused is the KO normal T cells followed the next day by iCART5. The first cohort of patients receives lymphodepletion [cyclophosphamide (60 mg/kg×2 days) and fludarabine (25 mg/m2×5 days)] and product #1. If no dose-limiting toxicity (DLT) is observed, Cohort 2 receives lymphodepletion, product #1 and 1-5×10e$^7$ total iCART5 (product #2) over 3 days (10%, 30%, 60% of the total dose); 1-5×10e$^7$ total CART5 is a suboptimal dose based on CART19 experiments in B-NHL8. If no DLT is observed in cohort 2, cohort 3 receives lymphodepletion, product #1 and 1-5×10e8 total CART5 (full dose). Patient from cohort #1 will is allowed to proceed to cohort #2 if no toxicity is observed within the first 4 weeks. Based on tumor clearance (and maximum at month 6) the iCART5 cells are depleted using the dimerizing agent rimiducid (NCT02744287) to prevent possible long-term T cell toxicity.

Preparation of IND package and FDA submission: Optimization of clinical-grade manufacturing is run in collaboration with the Clinical Vaccine and Cell Production Facility (CVPF). The results of all described preclinical experiments together with the clinical trial protocol are formatted to fit an IND application. Extensive support for the IND preparation is available within the CCI and ACC.

Patient enrollment and treatment: After successful submission of the IND and approval from all the regulatory agencies, the phase 1 trial is started at the University of Pennsylvania, within the Lymphoma Program (Director: Dr. Stephen Schuster; Scientific Director: Dr. Marco Ruella). The Lymphoma program has a dedicated clinical research unit (CRU) with extensive experience managing early-stage studies. Dr. Ruella is the Principal Investigator of this trial with Dr. Carl June being the Scientific Protocol Advisor. Manufacturing of the 2 products is performed at the CVPF.

Correlative studies: Patient samples (peripheral blood) are analyzed at multiple time points (apheresis, day −1, 0, 7, 14, 28, 60, 90) to test CART expansion (qPCR and flow cytometry), CART phenotype (CyTOF), CART gene expression profiling (GEP) (NanoString, single-cell RNAseq 10× Genomics) and cytokine levels in the serum (Luminex, 30-plex array). Additional studies are performed on tumor biopsies pre-treatment and post-treatment when available (RNAseq and Hyperion analysis of the tumor microenvironment).

This trial will be a key milestone in the development of novel combined immunotherapies as it represents an innovative immunotherapeutic approach to treat T cell non-Hodgkin lymphomas avoiding toxicity. Anti-CD5 CAR T cells kill tumor T cells but unavoidably also normal T cells due to similar CD5 expression. However, the strategy described herein includes the co-infusion of normal T cells that have been knocked out for CD5, thereby ensuring T cell immunological protection during CART5 anti-tumor activity. CART5 cells are then depleted using a suicide system to ensure normal immunological reconstitution long term. This is one of the first CART trials for T-NHL and the only one including a two-pronged approach addressing the issue of toxicity. T-NHL have a very poor prognosis, and there are currently no active immunotherapies available. Therefore the development of such an innovative strategy represents a vertical advance in the field of hematology and immunotherapy. Based on the clinical results of the phase 1 trials and the findings of the correlative studies this strategy can also be implemented to targeting multiple targets at the same time to avoid antigen-loss escape (e.g., CART5+ CART7) or combine CART with small molecules that can enhance CART-mediated killing.

Example 3: Anti-CD2 CAR T Cells (CART2) and CD2 Knocked-Out (KO) Normal T Cells

A two-pronged immunotherapy approach is disclosed herein that includes anti-CD2 CAR T cells (CART2) and CD2 knocked-out (KO) normal T cells (FIG. 3). The CART2 destroys T cell lymphoma (e.g. T-NHL) or T cell leukemia cells, but also kills normal T cells. Infusion of CD2 KO normal T cells provides CART-resistant T cell immunity until CART2 cells are depleted, in some cases by using a suicide gene (e.g. iCasp9).

Guide RNAs were designed to knock out the CD2 gene (and CD5) using the CRISPR/Cas9 system. CD2 was effectively knocked out 78% of the T cell population. Second generation anti-CD2 and anti-CD5 CARs (CART2 and CART5, respectively) were generated (FIG. 4). Knock out cells (CD2KO and CD5KO) were incubated with their corresponding CART cells (CART2 and CART5, respectively), stimulated, and population doublings measured (FIG. 7). Mock electroporated cells that did not contain gRNA were used as a control for comparison. Without CD2 KO CART2 cells would not expand (FIG. 7). With KO CART2 and CART5 reach about 5-8 population doublings (FIG. 7).

Jurkat cells were transduced with the different CAR2 constructs and with a GFP-NFAT reporter then co-cultured with CD2+ tumor cells (or controls) for 24 hours. The lead CART2 (C3043) shows increased NFAT activation (FIG. 14).

The CART expansion protocol was optimized CART2 and CART5 cells continued to expand up to 18 days when incubated with CD2KO or CD5 KO cells (FIG. 9).

Example 4: CART2 and CART5 Testing

FIG. 6 illustrates the CD5 (or CD2, or CD7) KO manufacturing process and CRISPR-Cas9 KO efficiency.

The 6 different CAR2 and 6 CAR5 constructs were challenged in vitro by co-culturing them with luciferase+ Jurkat cells (T-cell leukemia cell line). At 24 hrs, total killing was measured as relative reduction in luminescence. For CART2 only #3029, #3030 and #3043 show anti-tumor effect. (FIG. 10). For CART5, all the constructs demonstrated anti-tumor effects (FIG. 11). Lead CART candidates (CART2 C3043 and CART5 C3054) were selected and tested. The effects of CD2 or CD5 knock-out on CART function was tested). CART2- and CART5-resistant T cells were successfully generated (. CD5 and CD2 were knocked-out in normal T cells.

CART2 and CART5 activity against cutaneous T cell lymphoma was tested. Twenty-four hour killing assays were performed. CART2 cells were active against primary Sezary cells (leukemic Cutaneous T Cell Lymphoma) and the HH Sezary cell line (FIG. 15). Also CART5 were active against HH cells (FIG. 15).

In vivo efficacy of CART2 and CART5 was measured. NSG mice were engrafted with Luciferase+ Jurkat cells and mice were randomized to receive control T cells or CART2 or CART5 ($1\times10^6$) at day 7. Mice were imaged weekly using the IVIS Xenogen Spectrum and analyzed with LivingImage software. CART2 C3043 and CART5 C3054 were the most effective (FIG. 12).

CART2 and CART5 were demonstrated to recognize normal T cells (autologous and allogeneic) and kill them (FIG. 16).

It was also demonstrated that removal of the CAR target protects normal T cells from CART killing (FIG. 17). CD5 KO but not WT normal T cells were resistant to CART5 killing. Normal resting T cells are recognized and killed by CART2 (FIG. 17, top) and CART5 (FIG. 17, bottom). Efficient KO of CD2 or CD5 from normal T cells using CRISPR-Cas9 led to resistance to CART2 or CART5 killing respectively (FIG. 17).

CMV-specific T cells were present in CD2KO and CD5KO normal T cell products (FIG. 18). CD2 and CD5 KO normal T cells maintained the ability to recognize CMV peptides and produce cytokines (FIG. 18; HLA-A-02:01-CMV PP65 NLVPMVATV dextramer (SEQ ID NO: 101); ICS after 4 h exposure to CETF peptides. After secondary culture with CMV-peptide pulsed APC).

Example 5: Anti-CD7 CAR T Cells (CART7) and CD7 Knocked-Out (KO) Normal T Cells

A two-pronged immunotherapy approach is disclosed herein that includes anti-CD7 CAR T cells (CART7) and CD7 knocked-out (KO) normal T cells. The CART7 destroys T cell lymphoma (e.g. T-NHL) or T cell leukemia cells, but also kills normal T cells. Infusion of CD7 KO normal T cells provides CART-resistant T cell immunity until CART7 cells are depleted, in some cases by using a suicide gene (e.g. iCasp9).

Guide RNAs were designed to knock out the CD7 gene using the CRISPR/Cas9 system. CD7 was effectively knocked out 79% of the T cell population (FIG. 25). Six anti-CD7 CARs were generated (FIG. 25).

Example 6: Dual Specific CAR T Cells

Two lentiviral constructs were generated that included CAR5 (C3054) and CAR2 (C3043) linked by a P2A sequence (FIG. 19). Gene expression was driven by an EF1alpha promoter. The CAR5 construct has 4-1BB costimulatory and CD3zeta signaling domains. Efficient knock-out of both CD2 and CD5 in normal T cells was demonstrated (FIGS. 20A-20B).

Example 6: CD5 KO Enhances CART Immunotherapy

It was demonstrated that CD5 KO CART5s are more effective than CD5+ CART5s in vivo. CD5 KO increased CART5 anti-tumor efficacy (FIG. 21). In a Jurkat T-ALL xenograft model using NSG mice, CD5 KO CART5 ($2\times10^6$ cells/mouse) lead to complete long-term responses and longer survival as compared to WT CART5 (FIG. 21).

CD5 KO CART19 were also more effective than CD5+ CART19 in vivo. CD5 KO increased CART19 anti-tumor efficacy (FIG. 22). In a NALM6 B-ALL xenograft model CD5 KO CART19 exhibited drastically higher tumor control as compared to WT CART19 (FIG. 22).

CART5 and CART2 were also capable of targeting 20% of AML. CART2 cells were co-cultured with CD2+ AML cells and showed significant killing at 24 hours (FIGS. 23A-23B).

CART5 also targeted 100% of CLL and MCL. A cytotoxicity assay was performed and demonstrated that CART5 cells can recognize and kill CD5+ MCL cell lines (Jeko-1 and Mino) (FIG. 24).

These data demonstrate that knocking out CD5 enhances CART therapy when treating with an anti-CD5 CAR, or surprisingly when treating with a different CAR T cell (e.g. a CD19 CART cell).

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

SEQUENCE LISTING

```
Sequence total quantity: 101
SEQ ID NO: 1            moltype = DNA  length = 747
FEATURE                 Location/Qualifiers
misc_feature            1..747
                        note = CD2-MEDI507H2L-3028 CAR
source                  1..747
                        mol_type = other DNA
                        organism = synthetic construct
SEQUENCE: 1
ggatcccaag tccaactggt gcaatcaggc gcagaagtcc aacgaccggg ggccagtgtt   60
aaagtgtctt gtaaagcctc cgggtacatt tttactgagt actatatgta ctgggtcaga  120
caggccccag ggcaaggttt ggaacttgtc ggacgcatag atcccgaaga cggttctata  180
gattacgttg agaagttcaa aaagaaagtc acacttactg cggacacatc tagtagcacc  240
gcatatatgt aactgagcag tctcacctca gacgacaccg cagtgtacta ttgcgctcgc  300
ggaaagttta actataggtt cgcgtactgg ggacagggga cactggtgac tgttagcagc  360
ggtggcggag ggagcggcgg tggaggaagc ggaggcggag gttccgacgt tgtgatgacg  420
caaagtcccc cgtcactcct tgttactctc ggccagccag cgtctatctc ttgccggtca  480
agccagagct tgctccactc tagtggtaac acgtatttga actggttgct gcaaaggcct  540
ggacaatctc ctcagcccct gatctatttg gttagcaaac tggaaagtgg tgttccagac  600
agattttcag ggtctggatc aggcactgat ttcactctga agatctccgg ggtagaggcc  660
gaggacgtgg gagtctatta ctgcatgcag tttactcact atccttatac ctttggtcaa  720
gggacgaaac tggagatcaa atccgga                                      747

SEQ ID NO: 2            moltype = DNA  length = 756
FEATURE                 Location/Qualifiers
misc_feature            1..756
                        note = CD2-OKT11H2L-3029
source                  1..756
                        mol_type = other DNA
                        organism = synthetic construct
SEQUENCE: 2
ggatcccaag ttcagcttca gcaaccaggt gctgaattgg tccgccctgg aactagcgtt   60
aaactgtctt gtaaggcatc cggttatacg tttacaagtt attggatgca ctggattaag  120
caaaggcccg aacaaggcct tgaatggatt gggagaattg atccctacga tagcgagaca  180
cactacaatg aaaaatttaa agataaggcc atcctcagcg tagataagag cagttctacc  240
gcatacatac agctctcaag cctgacgtca gatgactcag ccgtttatta ttgctcaagg  300
cgggacgcta aatacgacgg ctatgcgctt gactactggg gacaaggcac cactttgaca  360
gtctccagtg gtggcggagg gagcggcggt ggaggaagcg gaggcggagg ttccgatata  420
gttatgacgc aagcagcacc ctctgtacct gtgacaccgg gtgaatccgt tagtatctca  480
tgccgctctt ctaaaaccct cttgcattct aacggcaata catatttgta ttggttcctt  540
caacgaccag gacaatcacc gcaagtgctt atttatagga tgtctaactt ggctagtggg  600
gtgccaaata ggttcagtgg gtctggatct gagacaactt tcacgttgag aataagtagg  660
gtggaagctg aagacgtcgg tatatactac tgtatgcagc atttggagta cccttacact  720
ttcggggag gtactaagct cgaaattaaa tccgga                             756

SEQ ID NO: 3            moltype = DNA  length = 756
FEATURE                 Location/Qualifiers
misc_feature            1..756
                        note = CD2-OKT11L2H-3030 CAR
```

```
source                          1..756
                                mol_type = other DNA
                                organism = synthetic construct
SEQUENCE: 3
ggatccgata tagttatgac gcaagcagca ccctctgtac ctgtgacacc gggtgaatcc   60
gttagtatct catgccgctc ttctaaaacc ctcttgcatt ctaacggcaa tacatatttg  120
tattggttcc ttcaacgacc aggacaatca ccgcaagtgc ttatttatag gatgtctaac  180
ttggctagtg gggtgccaaa taggttcagt gggtctggat ctgagacaac tttcacgttg  240
agaataagta gggtggaagc tgaagacgtc ggtatatact actgtatgca gcatttggag  300
taccttaca ctttcggggg aggtactaag ctcgaaatta aaggtggcgg agggagcggc  360
ggtggaggaa gcggaggcgg aggttcccaa gttcagcttc agcaaccagg tgctgaattg  420
gtccgccctg gaactagcgt taaactgtct tgtaaggcat ccggttatac gtttacaagt  480
tattggatgc actggattaa gcaaaggccc gaacaaggcc ttgaatggat tgggagaatt  540
gatccctacg atagcgagac acactacaat gaaaaattta aagataaggc catcctcagc  600
gtagataaga gcagttctac cgcatacata cagctctcaa gcctgacgtc agatgactca  660
gccgtttatt attgctcaag gcgggacgct aaatacgacg gctatgcgct tgactactgg  720
ggacaaggca ccactttgac agtctccagt tccgga                            756

SEQ ID NO: 4                    moltype = DNA  length = 753
FEATURE                         Location/Qualifiers
misc_feature                    1..753
                                note = CD2-T11-2-H2L-3031 CAR
source                          1..753
                                mol_type = other DNA
                                organism = synthetic construct
SEQUENCE: 4
ggatcccaag ttcaattgca gcaaccgggt gccgagttgg taaggcccgg tgcgtcagtc   60
aaacttagtt gtaaagctag tgggtacact tttactacgt tctggatgaa ttgggtgaag  120
caacgaccag gccaaggtct ggaatggatc ggcatgattg accgtctga ctcagaagct   180
cattacaacc agatgttcaa ggacaaggcg actctgactg ttgataaaag ctcaagcacc  240
gcctacatgc agctcagtag cctcacatcc gaggattccg cagtgtacta ttgcgcgagg  300
ggacgagggt atgatgacgg cgatgcgatg gactattggg gacaggggac cagcgtaaca  360
gtcagtagtg gtggcggagg gagcggcggt ggaggaagcg gaggcggagg ttccgatata  420
gttatgaccc agtctcccgc ctctctggcc gttagcttgg acaacgcgc taccatctct  480
taccgagcgt ctaagtccgt cagtaccaagc ggttatagtt acatgcactg gaaccagcaa  540
aagcccggac aacctccgag actcctgatt tatttggtct ctaaccttga gtcaggtgtc  600
ccagccagat tctccggctc tggaagcggc actgactttta cattgaacat tcaccccgtg  660
gaggaggaag acgctgctac ctactattgc atgcaattca cgcactatcc ctacacattc  720
ggggggggca cgaaattgga aatcaaatcc gga                               753

SEQ ID NO: 5                    moltype = DNA  length = 729
FEATURE                         Location/Qualifiers
misc_feature                    1..729
                                note = CD2-TS2-18.1.1-H2L-3032 CAR
source                          1..729
                                mol_type = other DNA
                                organism = synthetic construct
SEQUENCE: 5
ggatccgagg ttcagcttga ggagagtggg ggaggtttgg taatgccagg tgggtctttg   60
aaactcagtt gcgcggcgtc aggcttcgca ttttcctcct acgatatgtc ctgggtcaga  120
cagacaccg agaagcggct ggaatgggtc gcttacattt ccggggagg attcacgtac  180
taccgggata cagtaaaggg gagatttact ctgagccggg acaacgctaa gaataccctc  240
tatctccaga gtgtcctcttt gaagagtgaa gacacagcga tgtattactg tgcgagacaa  300
ggggccaatt gggagctggt ttactgggc aggggacga cattgacggt ttctagcggt  360
ggcggaggga gcggcggtgg aggaagcgga ggcggaggtt ccgacattgt aatgacacaa  420
tcacctgcta cacttagcgt gactccaggt gatcgggtat tcctgagctg ccgcgcatca  480
caaagtatat ccgacttcct gcactggtat cagcagaaat ctcacgaaag tcccaggctg  540
ctgattaaat acgcttccca gagtattagt ggtatcccct cacgattttc tggcagcggg  600
agcggtagtg acttcactct ttctataaac tccgtcgagc cagaagacgt gggggtgtat  660
ctttgccaaa atgacacaa ttttccacca acctttggtg gggcaccaa actcgaaata  720
aagtccgga                                                          729

SEQ ID NO: 6                    moltype = DNA  length = 729
FEATURE                         Location/Qualifiers
misc_feature                    1..729
                                note = CD2-TS2-18.1.1-L2H-3033 CAR
source                          1..729
                                mol_type = other DNA
                                organism = synthetic construct
SEQUENCE: 6
ggatccgaca ttgtaatgac acaatcaccct gctacactta gcgtgactcc aggtgatcgg   60
gtattcctga gctgccgcgc atcacaaagt atatccgact cctgcactg gtatcagcag  120
aaatctcacg aaagtcccag gctgctgatt aaatacgctt cccagagtat tagtggtatc  180
ccctcacgat tttctggcag cgggagcggt agtgacttca ctctttctat aaactccttt  240
gagccagaag acgtggggt gtatctttgc caaaatggac acaatttttcc accaaccttt  300
ggtgggggca ccaaactcga aataaagggt ggcgagga gcgcggtgg aggaagcgga  360
ggcggaggtt ccgaggttca gcttgaggag agtgggggag gtttggtaat gccaggtggg  420
tctttgaaac tcagttgcgc ggcgtcaggc ttcgcatttt cctcctacga tatgtcctgg  480
gtcagacaga cacccgagaa gcggctgaa tgggtcgctt acatttccgg gggaggattc  540
```

```
acgtactacc cggatacagt aaaggggaga tttactctga gccgggacaa cgctaagaat    600
accctctatc tccagatgtc ctctttgaag agtgaagaca cagcgatgta ttactgtgcg    660
agacaagggg ccaattggga gctggtttac tggggccagg ggacgacatt gacggtttct    720
agctccgga                                                             729

SEQ ID NO: 7           moltype = DNA   length = 747
FEATURE                Location/Qualifiers
misc_feature           1..747
                       note = CD2-MEDI507L2H-3043 CAR
source                 1..747
                       mol_type = other DNA
                       organism = synthetic construct
SEQUENCE: 7
ggatccgacg ttgtgatgac gcaaagtccc ccgtcactcc ttgttactct cggccagcca    60
gcgtctatct cttgccggtc aagccagagc ttgctccact ctagtggtaa cacgtatttg    120
aactggttgc tgcaaaggcc tggacaatct cctcagcccc tgatctattt ggttagcaaa    180
ctggaaagtg gtgttccaga cagattttca gggtctggat caggcactga tttcactctg    240
aagatctccg gggtagaggc cgaggacgtg ggagtctatt actgcatgca gtttactcac    300
tatccttata cctttggtca agggacgaaa ctggagatca aggtggcgg aggggagcggc    360
ggtggaggaa gcgaggcgg aggttcccaa gtccaactgg tgcaatcagg cgcagaagtc    420
caacgaccgg gggccagtgt aaagtgtctt tgtaaagcct ccgggtacat tttactgag    480
tactatatgt actgggtcag acaggcccca gggcaagtt tggaacttgt cgacgcata    540
gatcccgaag acgttctat agattacgtt gagaagttca aaaagaaagt cacacttact    600
gcggacacat ctagtagcac cgcatatatg gaactgagca gtctcacctc agacgacacc    660
gcagtgtact attgcgctcg cggaaagttt aactataggt tcgcgtactg ggggacagggg    720
acactggtga ctgttagcag ctccgga                                         747

SEQ ID NO: 8           moltype = DNA   length = 738
FEATURE                Location/Qualifiers
misc_feature           1..738
                       note = CD5-17L2H-3045 CAR
source                 1..738
                       mol_type = other DNA
                       organism = synthetic construct
SEQUENCE: 8
ggatccaaca ttgtactgac gcaaagcccc tcatctttgt ctgagtcact cggcggcaaa    60
gtaaccatca catgcaaggc cagtcaagac atcaataaat atattgcttg gtatcagtat    120
aaaccccggca agggggccgcg actgctgatt cactacacga gtaccttgca accgggcatt    180
ccgagccgat ttagtggcag tggctcaggt cgcgattact cattctcaat aagtaatctc    240
gaaccggaag acatagctac ttattattgc ttgcagtacg ataatttgtg gaccttcggg    300
ggtggtacaa agttggaaat aaagggtggc ggagggagcg cggtggagg aagcggaggc    360
ggaggttccg aggtccaact cgtagaatca ggtcccggat tggtgcaacc atcccagagc    420
ctctctatta catgcacggt ctctggattt agtctgacca attacgatgt gcattgggtg    480
cgccagtctc ccggcaaggg gttggaatgg cttggcgtta tatggaacta cggaaataca    540
gactataacc ccgcgtttat ctctcggctg agtatacgga aagacagtag taaatcccag    600
gtctttttta cgatgtcatc cctgcaaacg ccagataccg caatatatta ctgcgccagg    660
aaaccacggtg atggttatta taattggtac ttcgatgtgt gggtactgg cactacagtc    720
acagtatctt catctaga                                                   738

SEQ ID NO: 9           moltype = DNA   length = 741
FEATURE                Location/Qualifiers
misc_feature           1..741
                       note = CD5-9H2L-3048 CAR
source                 1..741
                       mol_type = other DNA
                       organism = synthetic construct
SEQUENCE: 9
ggatcccagg tccagctgaa agaaagcggt ccagagctgg aaaaacccgg tgcgagcgtc    60
aaatatcat gtaaagcaag cgggtattca ttcaccgcgt actctatgaa ctgggttaag    120
caaaacaacg gtatgtcctt ggagtggata gggtctatcg acccgtatta tgggacaca    180
aaatacgcgc agaaattcaa ggggaaggcc accctgaccg tagataaagc tagttctact    240
gcgtacttgc aactgaaaag cctcacttct gaggactctg ccgtctacta ctgtgctcgg    300
cgaatgataa cgacgggga ctggtatttc gatgtttggg gtacagggac tacggtgact    360
gtcagtagcg gtggcggagg gagcggcggt ggaggaagcg gaggcggagg ttcccatatc    420
gtcttgactc aatcacctag ttctttgtct cgtccttg cgaccgagt caccatatct    480
tgcagagcgt cacaggacat ttcaacgtac ctcaactggt atcagcaaaa accggacggg    540
actgtcaagc tcttgatctt ctacacttcc agactccacg ccggggtgcc aagcagattt    600
agtggctctg gcagcgggac acaccatagt cttacaatca gcaatgttga gcaagaagac    660
atagccacgt atttctgcca gcaagtaac tcacttccgt tcacgtttgg tagtggcacc    720
aaaactggaga taaatccgg a                                               741

SEQ ID NO: 10          moltype = DNA   length = 741
FEATURE                Location/Qualifiers
misc_feature           1..741
                       note = CD5-9L2H-3049 CAR
source                 1..741
                       mol_type = other DNA
                       organism = synthetic construct
```

```
SEQUENCE: 10
ggatcccata tcgtcttgac tcaatcacct agttctttgt ctgcgtccct tggcgaccga    60
gtcaccatat cttgcagagc gtcacaggac atttcaacgt acctcaactg gtatcagcaa   120
aaaccggacg ggactgtcaa gctcttgatc ttctacactt ccagactcca cgccggggtg   180
ccaagcagat ttagtggctc tggcagcggg acacaccaga gtcttacaat cagcaatctt   240
gagcaagaag acatagccac gtatttctgc cagcaaggta actcacttcc gttcacgttt   300
ggtagtggca ccaaactgga gataaaaggt ggcggaggga gcggcggtgg aggaagcgga   360
ggcggaggtt cccaggtcca gctgaaagaa agcggtccag agctggaaaa acccggtgcg   420
agcgtcaaaa tatcatgtaa agcaagcggg tattcattca ccgctactc tatgaactgg   480
gttaagcaaa acaacggtat gtccttggag tggataggt ctatcgaccc gtattatggg   540
gacacaaaat acgcgcagaa attcaagggg aaggccaccc tgaccgtaga taaagctagt   600
tctactgcgt acttgcaact gaaaagcctc acttctgagg actctgccgt ctactactgt   660
gctcggcgaa tgataacgac gggggactgg tatttcgatg tttggggtac agggactacg   720
gtgactgtca gtagctccgg a                                             741

SEQ ID NO: 11           moltype = DNA   length = 732
FEATURE                 Location/Qualifiers
misc_feature            1..732
                        note = CD5-34H2L-3052 CAR
source                  1..732
                        mol_type = other DNA
                        organism = synthetic construct
SEQUENCE: 11
ggatccgagg ttaaactcgt ggagagcggt gccgaactcg tccgaagtgg tgcttccgtt    60
aaactcagtt gtgccgcgtc aggatttaac ataaaagatt actacattca ctgggtcaaa   120
cagcgcccgg agcaggggct tgaatggatc gggtggattg atcctgaaaa cgggcgcacc   180
gaatatgctc ccaagttcca gggcaaagct actatgaccg ctgacacctc tagtaacact   240
gcctacctgc agttgagctc tcttacgtct gaggataccg ctgtgtacta ctgtaataac   300
ggaaattatg tacgacacta ttacttcgac tactgggggc agggcactac tgtgactgta   360
tctagcggtg gcggagggag cggcggtgga ggaagcggaa cggaggttc cgattggtcc   420
acacaatccc ctgcaatcct gagtgcatct ccaggcgaga agtaactat gacttgcaga   480
gctataagct ctgtgtccta catgcactgg tatcagcaga agccaggttc ttccccgaag   540
ccgtggatat atgctacaag caatttggca tccgtgttc cgcccggtt tagtggctcc   600
ggttctggga caagttactc cctcacgatc agcagggttg aagccgagga cgctgccact   660
tactattgcc aacagtggtc aagtaacccc aggactttcg ggggaggaac taaacttgaa   720
atcaaatcta ga                                                       732

SEQ ID NO: 12           moltype = DNA   length = 732
FEATURE                 Location/Qualifiers
misc_feature            1..732
                        note = CD5-34L2H-3053 CAR
source                  1..732
                        mol_type = other DNA
                        organism = synthetic construct
SEQUENCE: 12
ggatccgatt ggctcacaca atccctgca atcctgagtg catctccagg cgagaaagta    60
actatgactt gcagagctat aagctctgtg tcctacatgc actggtatca gcagaagcca   120
ggttcttccc cgaagccgtg gatatatgct acaagcaatt tggcatccgg tgttcccgcc   180
cggtttagtg gctccggttc tgggacaagt tactccctca cgatcagcag ggttgaagcc   240
gaggacgctg ccacttacta ttgccaacag tggtcaagta ccccaggac tttcggggga   300
ggaactaaac ttgaaatcaa aggtggcgga gggagcggca gtggaggaag cggaggcgga   360
ggttccgagg ttaaactcgt ggagagcggt gccgaactcg tccgaagtgg tgcttccgtt   420
aaactcagtt gtgccgcgtc aggatttaac ataaaagatt actacattca ctgggtcaaa   480
cagcgcccgg agcaggggct tgaatggatc gggtggattg atcctgaaaa cgggcgcacc   540
gaatatgctc ccaagttcca gggcaaagct actatgaccg ctgacacctc tagtaacact   600
gcctacctgc agttgagctc tcttacgtct gaggataccg ctgtgtacta ctgtaataac   660
ggaaattatg tacgacacta ttacttcgac tactgggggc agggcactac tgtgactgta   720
tctagctcta ga                                                       732

SEQ ID NO: 13           moltype = DNA   length = 738
FEATURE                 Location/Qualifiers
misc_feature            1..738
                        note = CD5-17H2L-3054 CAR
source                  1..738
                        mol_type = other DNA
                        organism = synthetic construct
SEQUENCE: 13
ggatccgagg tccaactcgt agaatcaggt cccggattgg tgcaaccatc ccagagcctc    60
tctattacat gcacggtctc tggatttagt ctgaccaatt acgatgtgca ttgggtgcgc   120
cagtctcccg gcaggggtt ggaatggctt ggcgttatat ggaactacgg aaatacagac   180
tataacgccc gtttatctc tcggctgagt atacggaaaa cagtagtaa atcccaggtc   240
ttttttacga tgtcatccct gcaaacgcca gataccgcaa tatattactg cgccaggaac   300
cacggtgatg ttattataa ttggtacttc gatgtgtggg gtactggcac tacagtcaca   360
gtatcttcag gtgcggagg gagcggcggt ggaggaagcg gaggcggagg ttccaacatt   420
gtactgacgc aaagccctc atctttgtct gagtcactcg gcggcaaagt aaccatcaca   480
tgcaaggcca gtcaagacat caataaatat attgcttggt atcagtataa acccggcaag   540
gggccgcgac tgctgattca ctacacgagt accttgcaac cgggcattcc gagccgattt   600
```

```
agtggcagtg gctcaggtcg cgattactca ttctcaataa gtaatctcga accggaagac    660
atagctactt attattgctt gcagtacgat aatttgtgga ccttcggggg tggtacaaag    720
ttggaaataa agtctaga                                                  738

SEQ ID NO: 14           moltype = DNA  length = 72
FEATURE                 Location/Qualifiers
misc_feature            1..72
                        note = CD8 transmembrane domain
source                  1..72
                        mol_type = other DNA
                        organism = synthetic construct
SEQUENCE: 14
atctacatct gggcgccctt ggccgggact tgtggggtcc ttctcctgtc actggttatc    60
accctttact gc                                                        72

SEQ ID NO: 15           moltype = AA   length = 24
FEATURE                 Location/Qualifiers
REGION                  1..24
                        note = CD8 transmembrane domain
source                  1..24
                        mol_type = protein
                        organism = synthetic construct
SEQUENCE: 15
IYIWAPLAGT CGVLLLSLVI TLYC                                           24

SEQ ID NO: 16           moltype = DNA  length = 135
FEATURE                 Location/Qualifiers
misc_feature            1..135
                        note = CD8 hinge domain
source                  1..135
                        mol_type = other DNA
                        organism = synthetic construct
SEQUENCE: 16
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                    135

SEQ ID NO: 17           moltype = AA   length = 45
FEATURE                 Location/Qualifiers
REGION                  1..45
                        note = CD8 hinge domain
source                  1..45
                        mol_type = protein
                        organism = synthetic construct
SEQUENCE: 17
TTTPAPRPPT PAPTIASQPL SLRPEACRPA AGGAVHTRGL DFACD                    45

SEQ ID NO: 18           moltype = DNA  length = 126
FEATURE                 Location/Qualifiers
misc_feature            1..126
                        note = 4-1BB
source                  1..126
                        mol_type = other DNA
                        organism = synthetic construct
SEQUENCE: 18
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

SEQ ID NO: 19           moltype = DNA  length = 336
FEATURE                 Location/Qualifiers
misc_feature            1..336
                        note = CD3-zeta
source                  1..336
                        mol_type = other DNA
                        organism = synthetic construct
SEQUENCE: 19
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc   240
cggaggggca aggggcacga tggcctttac caggtctca gtacagccac caaggacacc   300
tacgacgccc tcacatgca ggccctgccc cctcgc                              336

SEQ ID NO: 20           moltype = AA   length = 42
FEATURE                 Location/Qualifiers
REGION                  1..42
                        note = 4-1BB
```

|  |  |  |
|---|---|---|
| source | 1..42<br>mol_type = protein<br>organism = synthetic construct | |
| SEQUENCE: 20 | | |
| KRGRKKLLYI FKQPFMRPVQ TTQEEDGCSC RFPEEEEGGC EL | | 42 |

```
SEQ ID NO: 21          moltype = AA   length = 112
FEATURE                Location/Qualifiers
REGION                 1..112
                       note = CD3-zeta
source                 1..112
                       mol_type = protein
                       organism = synthetic construct
SEQUENCE: 21
RVKFSRSADA PAYKQGQNQL YNELNLGRRE EYDVLDKRRG RDPEMGGKPR RKNPQEGLYN   60
ELQKDKMAEA YSEIGMKGER RRGKGHDGLY QGLSTATKDT YDALHMQALP PR          112

SEQ ID NO: 22          moltype = DNA   length = 20
FEATURE                Location/Qualifiers
misc_feature           1..20
                       note = gRNA
source                 1..20
                       mol_type = other DNA
                       organism = synthetic construct
SEQUENCE: 22
acagctgaca ggctcgacac                                               20

SEQ ID NO: 23          moltype = DNA   length = 20
FEATURE                Location/Qualifiers
misc_feature           1..20
                       note = gRNA
source                 1..20
                       mol_type = other DNA
                       organism = synthetic construct
SEQUENCE: 23
cggctcagct ggtatgaccc                                               20

SEQ ID NO: 24          moltype = DNA   length = 20
FEATURE                Location/Qualifiers
misc_feature           1..20
                       note = gRNA
source                 1..20
                       mol_type = other DNA
                       organism = synthetic construct
SEQUENCE: 24
ggagcaggtg atgttgacgg                                               20

SEQ ID NO: 25          moltype = AA   length = 493
FEATURE                Location/Qualifiers
REGION                 1..493
                       note = CD2-MEDI507H2L-3028 CAR
source                 1..493
                       mol_type = protein
                       organism = synthetic construct
SEQUENCE: 25
MALPVTALLL PLALLLHAAR PGSQVQLVQS GAEVQRPGAS VKVSCKASGY IFTEYYMYWV   60
RQAPGQGLEL VGRIDPEDGS IDYVEKFKKK VTLTADTSSS TAYMELSSLT SDDTAVYYCA  120
RGKFNYRFAY WGQGTLVTVS SGGGGSGGGG SGGGGSDVVM TQSPPSLLVT LGQPASISCR  180
SSQSLLHSSG NTYLNWLLQR PGQSPQPLIY LVSKLESGVP DRFSGSGSGT DFTLKISGVE  240
AEDVGVYYCM QFTHYPYTFG QGTKLEIKSG TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYKQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                     493

SEQ ID NO: 26          moltype = AA   length = 493
FEATURE                Location/Qualifiers
REGION                 1..493
                       note = CD2-MEDI507L2H-3043 CAR
source                 1..493
                       mol_type = protein
                       organism = synthetic construct
SEQUENCE: 26
MALPVTALLL PLALLLHAAR PGSDVVMTQS PPSLLVTLGQ PASISCRSSQ SLLHSSGNTY   60
LNWLLQRPGQ SPQPLIYLVS KLESGVPDRF SGSGSGTDFT LKISGVEAED VGVYYCMQFT  120
HYPYTFGQGT KLEIKGGGGS GGGGSGGGGS QVQLVQSGAE VQRPGASVKV SCKASGYIFT  180
EYYMYWVRQA PGQGLELVGR IDPEDGSIDY VEKFKKKVTL TADTSSSTAY MELSSLTSDD  240
TAVYYCARGK FNYRFAYWGQ GTLVTVSSSG TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
```

```
TQEEDGCSCR FPEEEEGGCE LRVKFSRSAD APAYKQGQNQ LYNELNLGRR EEYDVLDKRR    420
GRDPEMGGKP RRKNPQEGLY NELQKDKMAE AYSEIGMKGE RRRGKGHDGL YQGLSTATKD    480
TYDALHMQAL PPR                                                       493

SEQ ID NO: 27          moltype = AA  length = 249
FEATURE                Location/Qualifiers
REGION                 1..249
                       note = CD2-MEDI507H2L-3028 scFv
source                 1..249
                       mol_type = protein
                       organism = synthetic construct
SEQUENCE: 27
GSQVQLVQSG AEVQRPGASV KVSCKASGYI FTEYYMYWVR QAPGQGLELV GRIDPEDGSI     60
DYVEKFKKKV TLTADTSSST AYMELSSLTS DDTAVYYCAR GKFNYRFAYW GQGTLVTVSS    120
GGGGSGGGGS GGGGSDVVMT QSPPSLLVTL GQPASISCRS SQSLLHSSGN TYLNWLLQRP    180
GQSPQPLIYL VSKLESGVPD RFSGSGSGTD FTLKISGVEA EDVGVYYCMQ FTHYPYTFGQ    240
GTKLEIKSG                                                           249

SEQ ID NO: 28          moltype = AA  length = 249
FEATURE                Location/Qualifiers
REGION                 1..249
                       note = CD2-MEDI507L2H-3043 scFv
source                 1..249
                       mol_type = protein
                       organism = synthetic construct
SEQUENCE: 28
GSDVVMTQSP PSLLVTLGQP ASISCRSSQS LLHSSGNTYL NWLLQRPGQS PQPLIYLVSK     60
LESGVPDRFS GSGSGTDFTL KISGVEAEDV GVYYCMQFTH YPYTFGQGTK LEIKGGGGSG    120
GGGSGGGGSQ VQLVQSGAEV QRPGASVKVS CKASGYIFTE YYMYWVRQAP GQGLELVGRI    180
DPEDGSIDYV EKFKKKVTLT ADTSSSTAYM ELSSLTSDDT AVYYCARGKF NYRFAYWGQG    240
TLVTVSSSG                                                           249

SEQ ID NO: 29          moltype = AA  length = 118
FEATURE                Location/Qualifiers
REGION                 1..118
                       note = CD2-MEDI507 VH
source                 1..118
                       mol_type = protein
                       organism = synthetic construct
SEQUENCE: 29
QVQLVQSGAE VQRPGASVKV SCKASGYIFT EYYMYWVRQA PGQGLELVGR IDPEDGSIDY     60
VEKFKKKVTL TADTSSSTAY MELSSLTSDD TAVYYCARGK FNYRFAYWGQ GTLVTVSS     118

SEQ ID NO: 30          moltype = AA  length = 112
FEATURE                Location/Qualifiers
REGION                 1..112
                       note = CD2-MEDI507 VL
source                 1..112
                       mol_type = protein
                       organism = synthetic construct
SEQUENCE: 30
DVVMTQSPPS LLVTLGQPAS ISCRSSQSLL HSSGNTYLNW LLQRPGQSPQ PLIYLVSKLE     60
SGVPDRFSGS GSGTDFTLKI SGVEAEDVGV YYCMQFTHYP YTFGQGTKLE IK           112

SEQ ID NO: 31          moltype = AA  length = 5
FEATURE                Location/Qualifiers
REGION                 1..5
                       note = CD2-MEDI507 HCDR1
source                 1..5
                       mol_type = protein
                       organism = synthetic construct
SEQUENCE: 31
EYYMY                                                                 5

SEQ ID NO: 32          moltype = AA  length = 17
FEATURE                Location/Qualifiers
REGION                 1..17
                       note = CD2-MEDI507 HCDR2
source                 1..17
                       mol_type = protein
                       organism = synthetic construct
SEQUENCE: 32
RIDPEDGSID YVEKFKK                                                   17

SEQ ID NO: 33          moltype = AA  length = 9
FEATURE                Location/Qualifiers
REGION                 1..9
                       note = CD2-MEDI507 HCDR3
```

```
source                  1..9
                        mol_type = protein
                        organism = synthetic construct
SEQUENCE: 33
GKFNYRFAY                                                                9

SEQ ID NO: 34           moltype = AA   length = 16
FEATURE                 Location/Qualifiers
REGION                  1..16
                        note = CD2-MEDI507 LCDR1
source                  1..16
                        mol_type = protein
                        organism = synthetic construct
SEQUENCE: 34
RSSQSLLHSS GNTYLN                                                       16

SEQ ID NO: 35           moltype = AA   length = 7
FEATURE                 Location/Qualifiers
REGION                  1..7
                        note = CD2-MEDI507 LCDR2
source                  1..7
                        mol_type = protein
                        organism = synthetic construct
SEQUENCE: 35
LVSKLES                                                                  7

SEQ ID NO: 36           moltype = AA   length = 9
FEATURE                 Location/Qualifiers
REGION                  1..9
                        note = CD2-MEDI507 LCDR3
source                  1..9
                        mol_type = protein
                        organism = synthetic construct
SEQUENCE: 36
MQFTHYPYT                                                                9

SEQ ID NO: 37           moltype = AA   length = 496
FEATURE                 Location/Qualifiers
REGION                  1..496
                        note = CD2-OKT11H2L-3029 CAR
source                  1..496
                        mol_type = protein
                        organism = synthetic construct
SEQUENCE: 37
MALPVTALLL PLALLLHAAR PGSQVQLQQP GAELVRPGTS VKLSCKASGY TFTSYWMHWI        60
KQRPEQGLEW IGRIDPYDSE THYNEKFKDK AILSVDKSSS TAYIQLSSLT SDDSAVYYCS       120
RRDAKYDGYA LDYWGQGTTL TVSSGGGGSG GGGSGGGGSD IVMTQAAPSV PVTPGESVSI       180
SCRSSKTLLH SNGNTYLYWF LQRPGQSPQV LIYRMSNLAS GVPNRFSGSG SETTFTLRIS       240
RVEAEDVGIY YCMQHLEYPY TFGGGTKLEI KSGTTTPAPR PPTPAPTIAS QPLSRPEAC        300
RPAAGGAVHT RGLDFACDIY IWAPLAGTCG VLLLSLVITL YCKRGRKKLL YIFKQPFMRP       360
VQTTQEEDGC SCRFPEEEEG GCELRVKFSR SADAPAYKQG QNQLYNELNL GRREEYDVLD       420
KRRGRDPEMG GKPRRKNPQE GLYNELQKDK MAEAYSEIGM KGERRRGKGH DGLYQGLSTA       480
TKDTYDALHM QALPPR                                                      496

SEQ ID NO: 38           moltype = AA   length = 496
FEATURE                 Location/Qualifiers
REGION                  1..496
                        note = CD2-OKT11L2H-3030 CAR
source                  1..496
                        mol_type = protein
                        organism = synthetic construct
SEQUENCE: 38
MALPVTALLL PLALLLHAAR PGSDIVMTQA APSVPVTPGE SVSISCRSSK TLLHSNGNTY        60
LYWFLQRPGQ SPQVLIYRMS NLASGVPNRF SGSGSETTFT LRISRVEAED VGIYYCMQHL       120
EYPYTFGGGT KLEIKGGGGS GGGGSGGGGS QVQLQQPGAE LVRPGTSVKL SCKASGYTFT       180
SYWMHWIKQR PEQGLEWIGR IDPYDSETHY NEKFKDKAIL SVDKSSSTAY IQLSSLTSDD       240
SAVYYCSRRD AKYDGYALDY WGQGTTLTVS SGTTTPAPR PPTPAPTIAS QPLSRPEAC         300
RPAAGGAVHT RGLDFACDIY IWAPLAGTCG VLLLSLVITL YCKRGRKKLL YIFKQPFMRP       360
VQTTQEEDGC SCRFPEEEEG GCELRVKFSR SADAPAYKQG QNQLYNELNL GRREEYDVLD       420
KRRGRDPEMG GKPRRKNPQE GLYNELQKDK MAEAYSEIGM KGERRRGKGH DGLYQGLSTA       480
TKDTYDALHM QALPPR                                                      496

SEQ ID NO: 39           moltype = AA   length = 252
FEATURE                 Location/Qualifiers
REGION                  1..252
                        note = CD2-OKT11H2L-3029 scFv
source                  1..252
                        mol_type = protein
                        organism = synthetic construct
```

```
SEQUENCE: 39
GSQVQLQQPG AELVRPGTSV KLSCKASGYT FTSYWMHWIK QRPEQGLEWI GRIDPYDSET      60
HYNEKFKDKA ILSVDKSSST AYIQLSSLTS DDSAVYYCSR RDAKYDGYAL DYWGQGTTLT     120
VSSGGGGSGG GGSGGGGSDI VMTQAAPSVP VTPGESVSIS CRSSKTLLHS NGNTYLYWFL    180
QRPGQSPQVL IYRMSNLASG VPNRFSGSGS ETTFTLRISR VEAEDVGIYY CMQHLEYPYT    240
FGGGTKLEIK SG                                                         252

SEQ ID NO: 40           moltype = AA  length = 252
FEATURE                 Location/Qualifiers
REGION                  1..252
                        note = CD2-OKT11L2H-3030 scFv
source                  1..252
                        mol_type = protein
                        organism = synthetic construct
SEQUENCE: 40
GSDIVMTQAA PSVPVTPGES VSISCRSSKT LLHSNGNTYL YWFLQRPGQS PQVLIYRMSN      60
LASGVPNRFS GSGSETTFTL RISRVEAEDV GIYYCMQHLE YPYTFGGGTK LEIKGGGGSG    120
GGGSGGGGSQ VQLQQPGAEL VRPGTSVKLS CKASGYTFTS YWMHWIKQRP EQGLEWIGRI    180
DPYDSETHYN EKFKDKAILS VDKSSSTAYI QLSSLTSDDS AVYYCSRRDA KYDGYALDYW    240
GQGTTLTVSS SG                                                         252

SEQ ID NO: 41           moltype = AA  length = 121
FEATURE                 Location/Qualifiers
REGION                  1..121
                        note = CD2-OKT11 VH
source                  1..121
                        mol_type = protein
                        organism = synthetic construct
SEQUENCE: 41
QVQLQQPGAE LVRPGTSVKL SCKASGYTFT SYWMHWIKQR PEQGLEWIGR IDPYDSETHY      60
NEKFKDKAIL SVDKSSSTAY IQLSSLTSDD SAVYYCSRRD AKYDGYALDY WGQGTTLTVS    120
S                                                                     121

SEQ ID NO: 42           moltype = AA  length = 112
FEATURE                 Location/Qualifiers
REGION                  1..112
                        note = CD2-OKT11 VL
source                  1..112
                        mol_type = protein
                        organism = synthetic construct
SEQUENCE: 42
DIVMTQAAPS VPVTPGESVS ISCRSSKTLL HSNGNTYLYW FLQRPGQSPQ VLIYRMSNLA      60
SGVPNRFSGS GSETTFTLRI SRVEAEDVGI YYCMQHLEYP YTFGGGTKLE IK             112

SEQ ID NO: 43           moltype = AA  length = 5
FEATURE                 Location/Qualifiers
REGION                  1..5
                        note = CD2-OKT11 HCDR1
source                  1..5
                        mol_type = protein
                        organism = synthetic construct
SEQUENCE: 43
SYWMH                                                                   5

SEQ ID NO: 44           moltype = AA  length = 17
FEATURE                 Location/Qualifiers
REGION                  1..17
                        note = CD2-OKT11 HCDR2
source                  1..17
                        mol_type = protein
                        organism = synthetic construct
SEQUENCE: 44
RIDPYDSETH YNEKFKD                                                     17

SEQ ID NO: 45           moltype = AA  length = 12
FEATURE                 Location/Qualifiers
REGION                  1..12
                        note = CD2-OKT11 HCDR3
source                  1..12
                        mol_type = protein
                        organism = synthetic construct
SEQUENCE: 45
RDAKYDGYAL DY                                                          12

SEQ ID NO: 46           moltype = AA  length = 16
FEATURE                 Location/Qualifiers
REGION                  1..16
                        note = CD2-OKT11 LCDR1
```

```
source                  1..16
                        mol_type = protein
                        organism = synthetic construct
SEQUENCE: 46
RSSKTLLHSN GNTYLY                                                      16

SEQ ID NO: 47           moltype = AA   length = 7
FEATURE                 Location/Qualifiers
REGION                  1..7
                        note = CD2-OKT11 LCDR2
source                  1..7
                        mol_type = protein
                        organism = synthetic construct
SEQUENCE: 47
RMSNLAS                                                                 7

SEQ ID NO: 48           moltype = AA   length = 9
FEATURE                 Location/Qualifiers
REGION                  1..9
                        note = CD2-OKT11 LCDR3
source                  1..9
                        mol_type = protein
                        organism = synthetic construct
SEQUENCE: 48
MQHLEYPYT                                                               9

SEQ ID NO: 49           moltype = AA   length = 495
FEATURE                 Location/Qualifiers
REGION                  1..495
                        note = CD2-T11-2-H2L-3031 CAR
source                  1..495
                        mol_type = protein
                        organism = synthetic construct
SEQUENCE: 49
MALPVTALLL PLALLLHAAR PGSQVQLQQP GAELVRPGAS VKLSCKASGY TFTTFWMNWV        60
KQRPGQGLEW IGMIDPSDSE AHYNQMFKDK ATLTVDKSSS TAYMQLSSLT SEDSAVYYCA       120
RGRGYDDGDA MDYWGQGTSV TVSSGGGGSG GGGSGGGGSD IVMTQSPASL AVSLGQRATI       180
SYRASKSVST SGYSYMHWNQ QKPGQPPRLL IYLVSNLESG VPARFSGSGS GTDFTLNIHP       240
VEEEDAATYY CMQFTHYPYT FGGGTKLEIK SGTTTPAPRP PTPAPTIASQ PLSLRPEACR       300
PAAGGAVHTR GLDFACDIYI WAPLAGTCGV LLLSLVITLY CKRGRKKLLY IPKQPFMRPV       360
QTTQEEDGCS CRFPEEEEGG CELRVKFSRS ADAPAYKQGQ NQLYNELNLG RREEYDVLDK       420
RRGRDPEMGG KPRRKNPQEG LYNELQKDKM AEAYSEIGMK GERRRGKGHD GLYQGLSTAT       480
KDTYDALHMQ ALPPR                                                       495

SEQ ID NO: 50           moltype = AA   length = 251
FEATURE                 Location/Qualifiers
REGION                  1..251
                        note = CD2-T11-2-H2L-3031 scFv
source                  1..251
                        mol_type = protein
                        organism = synthetic construct
SEQUENCE: 50
GSQVQLQQPG AELVRPGASV KLSCKASGYT FTTFWMNWVK QRPGQGLEWI GMIDPSDSEA        60
HYNQMFKDKA TLTVDKSSST AYMQLSSLTS EDSAVYYCAR GRGYDDGDAM DYWGQGTSVT       120
VSSGGGGSGG GGSGGGGSDI VMTQSPASLA VSLGQRATIS YRASKSVSTS GYSYMHWNQQ       180
KPGQPPRLLI YLVSNLESGV PARFSGSGSG TDFTLNIHPV EEEDAATYYC MQFTHYPYTF       240
GGGTKLEIKS G                                                           251

SEQ ID NO: 51           moltype = AA   length = 121
FEATURE                 Location/Qualifiers
REGION                  1..121
                        note = CD2-T11-2-H2L-3031 VH
source                  1..121
                        mol_type = protein
                        organism = synthetic construct
SEQUENCE: 51
QVQLQQPGAE LVRPGASVKL SCKASGYTFT TFWMNWVKQR PGQGLEWIGM IDPSDSEAHY        60
NQMFKDKATL TVDKSSSTAY MQLSSLTSED SAVYYCARGR GYDDGDAMDY WGQGTSVTVS       120
S                                                                      121

SEQ ID NO: 52           moltype = AA   length = 111
FEATURE                 Location/Qualifiers
REGION                  1..111
                        note = CD2-T11-2-H2L-3031 VL
source                  1..111
                        mol_type = protein
                        organism = synthetic construct
```

-continued

```
SEQUENCE: 52
DIVMTQSPAS LAVSLGQRAT ISYRASKSVS TSGYSYMHWN QQKPGQPPRL LIYLVSNLES    60
GVPARFSGSG SGTDFTLNIH PVEEEDAATY YCMQFTHYPY TFGGGTKLEI K            111

SEQ ID NO: 53           moltype = AA  length = 5
FEATURE                 Location/Qualifiers
REGION                  1..5
                        note = CD2-T11-2 HCDR1
source                  1..5
                        mol_type = protein
                        organism = synthetic construct
SEQUENCE: 53
TFWMN                                                                5

SEQ ID NO: 54           moltype = AA  length = 17
FEATURE                 Location/Qualifiers
REGION                  1..17
                        note = CD2-T11-2 HCDR2
source                  1..17
                        mol_type = protein
                        organism = synthetic construct
SEQUENCE: 54
MIDPSDSEAH YNQMFKD                                                  17

SEQ ID NO: 55           moltype = AA  length = 12
FEATURE                 Location/Qualifiers
REGION                  1..12
                        note = CD2-T11-2 HCDR3
source                  1..12
                        mol_type = protein
                        organism = synthetic construct
SEQUENCE: 55
GRGYDDGDAM DY                                                       12

SEQ ID NO: 56           moltype = AA  length = 15
FEATURE                 Location/Qualifiers
REGION                  1..15
                        note = CD2-T11-2 LCDR1
source                  1..15
                        mol_type = protein
                        organism = synthetic construct
SEQUENCE: 56
RASKSVSTSG YSYMH                                                    15

SEQ ID NO: 57           moltype = AA  length = 7
FEATURE                 Location/Qualifiers
REGION                  1..7
                        note = CD2-T11-2 LCDR2
source                  1..7
                        mol_type = protein
                        organism = synthetic construct
SEQUENCE: 57
LVSNLES                                                              7

SEQ ID NO: 58           moltype = AA  length = 9
FEATURE                 Location/Qualifiers
REGION                  1..9
                        note = CD2-T11-2 LCDR3
source                  1..9
                        mol_type = protein
                        organism = synthetic construct
SEQUENCE: 58
MQFTHYPYT                                                            9

SEQ ID NO: 59           moltype = AA  length = 487
FEATURE                 Location/Qualifiers
REGION                  1..487
                        note = CD2-TS2-18.1.1-H2L-3032 CAR
source                  1..487
                        mol_type = protein
                        organism = synthetic construct
SEQUENCE: 59
MALPVTALLL PLALLLHAAR PGSEVQLEES GGGLVMPGGS LKLSCAASGF AFSSYDMSWV    60
RQTPEKRLEW VAYISGGGFT YYPDTVKGRF TLSRDNAKNT LYLQMSSLKS EDTAMYYCAR   120
QGANWELVYW GQGTTLTVSS GGGGSGGGGS GGGGSDIVMT QSPATLSVTP GDRVFLSCRA   180
SQSISDFLHW YQQKSHESPR LLIKYASQSI SGIPSRFSGS GSGSDFTLSI NSVEPEDVGV   240
YLCQNGHNFP PTFGGGTKLE IKSGTTTPAP RPPTPAPTIA SQPLSLRPEA CRPAAGGAVH   300
TRGLDFACDI YIWAPLAGTC GVLLLSLVIT LYCKRGRKKL LYIFKQPFMR PVQTTQEEDG   360
CSCRFPEEEE GGCELRVKFS RSADAPAYKQ GQNQLYNELN LGRREEYDVL DKRRGRDPEM   420
```

```
                            GGKPRRKNPQ EGLYNELQKD KMAEAYSEIG MKGERRRGKG HDGLYQGLST ATKDTYDALH    480
MQALPPR                                                                                        487

SEQ ID NO: 60           moltype = AA  length = 487
FEATURE                 Location/Qualifiers
REGION                  1..487
                        note = CD2-TS2-18.1.1-L2H-3033 CAR
source                  1..487
                        mol_type = protein
                        organism = synthetic construct
SEQUENCE: 60
MALPVTALLL PLALLLHAAR PGSDIVMTQS PATLSVTPGD RVFLSCRASQ SISDFLHWYQ    60
QKSHESPRLL IKYASQSISG IPSRFSGSGS GSDFTLSINS VEPEDVGVYL CQNGHNFPPT    120
FGGGTKLEIK GGGGSGGGGS GGGGSEVQLE ESGGGLVMPG GSLKLSCAAS GFAFSSYDMS    180
WVRQTPEKRL EWVAYISGGG FTYYPDTVKG RFTLSRDNAK NTLYLQMSSL KSEDTAMYYC    240
ARQGANWELV YWGQGTTLTV SSSGTTTPAP RPPTPAPTIA SQPLSLRPEA CRPAAGGAVH    300
TRGLDFACDI YIWAPLAGTC GVLLLSLVIT LYCKRGRKKL LYIFKQPFMR PVQTTQEEDG    360
CSCRFPEEEE GGCELRVKFS RSADAPAYKQ GQNQLYNELN LGRREEYDVL DKRRGRDPEM    420
GGKPRRKNPQ EGLYNELQKD KMAEAYSEIG MKGERRRGKG HDGLYQGLST ATKDTYDALH    480
MQALPPR                                                             487

SEQ ID NO: 61           moltype = AA  length = 243
FEATURE                 Location/Qualifiers
REGION                  1..243
                        note = CD2-TS2-18.1.1-H2L-3032 scFv
source                  1..243
                        mol_type = protein
                        organism = synthetic construct
SEQUENCE: 61
GSEVQLEESG GGLVMPGGSL KLSCAASGFA FSSYDMSWVR QTPEKRLEWV AYISGGGFTY    60
YPDTVKGRFT LSRDNAKNTL YLQMSSLKSE DTAMYYCARQ GANWELVYWG QGTTLTVSSG    120
GGGSGGGGSG GGGSDIVMTQ SPATLSVTPG DRVFLSCRAS QSISDFLHWY QQKSHESPRL    180
LIKYASQSIS GIPSRFSGSG SGSDFTLSIN SVEPEDVGVY LCQNGHNFPP TFGGGTKLEI    240
KSG                                                                 243

SEQ ID NO: 62           moltype = AA  length = 243
FEATURE                 Location/Qualifiers
REGION                  1..243
                        note = CD2-TS2-18.1.1-L2H-3033 scFv
source                  1..243
                        mol_type = protein
                        organism = synthetic construct
SEQUENCE: 62
GSDIVMTQSP ATLSVTPGDR VFLSCRASQS ISDFLHWYQQ KSHESPRLLI KYASQSISGI    60
PSRFSGSGSG SDFTLSINSV EPEDVGVYLC QNGHNFPPTF GGGTKLEIKG GGGSGGGGSG    120
GGGSEVQLEE SGGGLVMPGG SLKLSCAASG FAFSSYDMSW VRQTPEKRLE WVAYISGGGF    180
TYYPDTVKGR FTLSRDNAKN TLYLQMSSLK SEDTAMYYCA RQGANWELVY WGQGTTLTVS    240
SSG                                                                 243

SEQ ID NO: 63           moltype = AA  length = 117
FEATURE                 Location/Qualifiers
REGION                  1..117
                        note = CD2-TS2-18.1.1 VH
source                  1..117
                        mol_type = protein
                        organism = synthetic construct
SEQUENCE: 63
EVQLEESGGG LVMPGGSLKL SCAASGFAFS SYDMSWVRQT PEKRLEWVAY ISGGGFTYYP    60
DTVKGRFTLS RDNAKNTLYL QMSSLKSEDT AMYYCARQGA NWELVYWGQG TTLTVSS       117

SEQ ID NO: 64           moltype = AA  length = 107
FEATURE                 Location/Qualifiers
REGION                  1..107
                        note = CD2-TS2-18.1.1 VL
source                  1..107
                        mol_type = protein
                        organism = synthetic construct
SEQUENCE: 64
DIVMTQSPAT LSVTPGDRVF LSCRASQSIS DFLHWYQQKS HESPRLLIKY ASQSISGIPS    60
RFSGSGSGSD FTLSINSVEP EDVGVYLCQN GHNFPPTFGG GTKLEIK                 107

SEQ ID NO: 65           moltype = AA  length = 5
FEATURE                 Location/Qualifiers
REGION                  1..5
                        note = CD2-TS2-18.1.1 HCDR1
source                  1..5
                        mol_type = protein
                        organism = synthetic construct
```

```
SEQUENCE: 65
SYDMS                                                                    5

SEQ ID NO: 66           moltype = AA  length = 16
FEATURE                 Location/Qualifiers
REGION                  1..16
                        note = CD2-TS2-18.1.1 HCDR2
source                  1..16
                        mol_type = protein
                        organism = synthetic construct
SEQUENCE: 66
YISGGGFTYY PDTVKG                                                        16

SEQ ID NO: 67           moltype = AA  length = 9
FEATURE                 Location/Qualifiers
REGION                  1..9
                        note = CD2-TS2-18.1.1 HCDR3
source                  1..9
                        mol_type = protein
                        organism = synthetic construct
SEQUENCE: 67
QGANWELVY                                                                9

SEQ ID NO: 68           moltype = AA  length = 11
FEATURE                 Location/Qualifiers
REGION                  1..11
                        note = CD2-TS2-18.1.1 LCDR1
source                  1..11
                        mol_type = protein
                        organism = synthetic construct
SEQUENCE: 68
RASQSISDFL H                                                             11

SEQ ID NO: 69           moltype = AA  length = 7
FEATURE                 Location/Qualifiers
REGION                  1..7
                        note = CD2-TS2-18.1.1 LCDR2
source                  1..7
                        mol_type = protein
                        organism = synthetic construct
SEQUENCE: 69
YASQSIS                                                                  7

SEQ ID NO: 70           moltype = AA  length = 9
FEATURE                 Location/Qualifiers
REGION                  1..9
                        note = CD2-TS2-18.1.1 LCDR3
source                  1..9
                        mol_type = protein
                        organism = synthetic construct
SEQUENCE: 70
QNGHNFPPT                                                                9

SEQ ID NO: 71           moltype = AA  length = 494
FEATURE                 Location/Qualifiers
REGION                  1..494
                        note = CD5-17L2H-3045 CAR
source                  1..494
                        mol_type = protein
                        organism = synthetic construct
SEQUENCE: 71
MALPVTALLL PLALLLHAAR PGSNIVLTQS PSSLSESLGG KVTITCKASQ DINKYIAWYQ         60
YKPGKGPRLL IHYTSTLQPG IPSRFSGSGS GRDYSFSISN LEPEDIATYY CLQYDNLWTF        120
GGGTKLEIKG GGGSGGGGSG GGGSEVQLVE SGPGLVQPSQ SLSITCTVSG FSLTNYDVHW        180
VRQSPGKGLE WLGVIWNYGN TDYNAAFISR LSIRKDSSKS QVFFTMSSLQ TPDTAIYYCA        240
RNHGDGYYNW YFDVWGTGTT VTVSSSRTTT PAPRPPTPAP TIASQPLSLR PEACRPAAGG        300
AVHTRGLDFA CDIYIWAPLA GTCGVLLLSL VITLYCHMKR GRKKLLYIFK QPFMRPVQTT        360
QEEDGCSCRF PEEEEGGCEL TSRVKFSRSA DAPAYQQGQN QLYNELNLGR REEYDVLDKR        420
RGRDPEMGGK PRRKNPQEGL YNELQKDKMA EAYSEIGMKG ERRRGKGHDG LYQGLSTATK        480
DTYDALHMQA LPPR                                                         494

SEQ ID NO: 72           moltype = AA  length = 494
FEATURE                 Location/Qualifiers
REGION                  1..494
                        note = CD5-17H2L-3054 CAR
source                  1..494
                        mol_type = protein
                        organism = synthetic construct
```

```
SEQUENCE: 72
MALPVTALLL PLALLLHAAR PGSEVQLVES GPGLVQPSQS LSITCTVSGF SLTNYDVHWV      60
RQSPGKGLEW LGVIWNYGNT DYNAAFISRL SIRKDSSKSQ VFFTMSSLQT PDTAIYYCAR     120
NHGDYYNWY FDVWGTGTTV TVSSGGGGSG GGGSGGGGSN IVLTQSPSSL SESLGGKVTI     180
TCKASQDINK YIAWYQYKPG KGPRLLIHYT STLQPGIPSR FSGSGSGRDY SFSISNLEPE     240
DIATYYCLQY DNLWTFGGGT KLEIKSRTTT PAPRPPTPAP TIASQPLSLR PEACRPAAGG     300
AVHTRGLDFA CDIYIWAPLA GTCGVLLLSL VITLYCHMKR GRKKLLYIFK QPFMRPVQTT     360
QEEDGCSCRF PEEEEGGCEL TSRVKFSRSA DAPAYQQGQN QLYNELNLGR REEYDVLDKR     420
RGRDPEMGGK PRRKNPQEGL YNELQKDKMA EAYSEIGMKG ERRRGKGHDG LYQGLSTATK     480
DTYDALHMQA LPPR                                                       494

SEQ ID NO: 73           moltype = AA  length = 242
FEATURE                 Location/Qualifiers
REGION                  1..242
                        note = CD5-17L2H-3045 scFv
source                  1..242
                        mol_type = protein
                        organism = synthetic construct
SEQUENCE: 73
NIVLTQSPSS LSESLGGKVT ITCKASQDIN KYIAWYQYKP GKGPRLLIHY TSTLQPGIPS      60
RFSGSGSGRD YSFSISNLEP EDIATYYCLQ YDNLWTFGGG TKLEIKGGGG SGGGGSGGGG     120
SEVQLVESGP GLVQPSQSLS ITCTVSGFSL TNYDHVWVRQ SPGKGLEWLG VIWNYGNTDY     180
NAAFISRLSI RKDSSKSQVF FTMSSLQTPD TAIYYCARNH GDGYYNWYFD VWGTGTTVTV     240
SS                                                                    242

SEQ ID NO: 74           moltype = AA  length = 242
FEATURE                 Location/Qualifiers
REGION                  1..242
                        note = CD5-17H2L-3054 scFv
source                  1..242
                        mol_type = protein
                        organism = synthetic construct
SEQUENCE: 74
EVQLVESGPG LVQPSQSLSI TCTVSGFSLT NYDHVWVRQS PGKGLEWLGV IWNYGNTDYN      60
AAFISRLSIR KDSSKSQVFF TMSSLQTPDT AIYYCARNHG DGYYNWYFDV WGTGTTVTVS     120
SGGGGSGGGG SGGGGSNIVL TQSPSSLSES LGGKVTITCK ASQDINKYIA WYQYKPGKGP     180
RLLIHYTSTL QPGIPSRFSG SGSGRDYSFS ISNLEPEDIA TYYCLQYDNL WTFGGGTKLE     240
IK                                                                    242

SEQ ID NO: 75           moltype = AA  length = 121
FEATURE                 Location/Qualifiers
REGION                  1..121
                        note = CD5-17 VH
source                  1..121
                        mol_type = protein
                        organism = synthetic construct
SEQUENCE: 75
EVQLVESGPG LVQPSQSLSI TCTVSGFSLT NYDHVWVRQS PGKGLEWLGV IWNYGNTDYN      60
AAFISRLSIR KDSSKSQVFF TMSSLQTPDT AIYYCARNHG DGYYNWYFDV WGTGTTVTVS     120
S                                                                     121

SEQ ID NO: 76           moltype = AA  length = 106
FEATURE                 Location/Qualifiers
REGION                  1..106
                        note = CD5-17 VL
source                  1..106
                        mol_type = protein
                        organism = synthetic construct
SEQUENCE: 76
NIVLTQSPSS LSESLGGKVT ITCKASQDIN KYIAWYQYKP GKGPRLLIHY TSTLQPGIPS      60
RFSGSGSGRD YSFSISNLEP EDIATYYCLQ YDNLWTFGGG TKLEIK                    106

SEQ ID NO: 77           moltype = AA  length = 491
FEATURE                 Location/Qualifiers
REGION                  1..491
                        note = CD5-9H2L-3048 CAR
source                  1..491
                        mol_type = protein
                        organism = synthetic construct
SEQUENCE: 77
MALPVTALLL PLALLLHAAR PGSQVQLKES GPELEKPGAS VKISCKASGY SFTAYSMNWV      60
KQNNGMSLEW IGSIDPYYGD TKYAQKFKGK ATLTVDKASS TAYLQLKSLT SEDSAVYYCA     120
RRMITTGDWY FDVWGTGTTV TVSSGGGGSG GGGSGGGGSH IVLTQSPSSL SASLGDRVTI     180
SCRASQDIST YLNWYQQKPD GTVKLLIFYT SRLHAGVPSR FSGSGSGTHH SLTISNLEQE     240
DIATYFCQQG NSLPFTFGSG TKLEIKSGTT TPAPRPPTPA PTIASQPLSL RPEACRPAAG     300
GAVHTRGLDF ACDIYIWAPL AGTCGVLLLS LVITLYCKRG RKKLLYIFKQ PPMRPVQTTQ     360
EEDGCSCRFP EEEEGGCELR VKFSRSADAP AYKQGQNQLY NELNLGRREE YDVLDKRRGR     420
DPEMGGKPRR KNPQEGLYNE LQKDKMAEAY SEIGMKGERR RGKGHDGLYQ GLSTATKDTY     480
DALHMQALPP R                                                          491
```

```
SEQ ID NO: 78           moltype = AA  length = 491
FEATURE                 Location/Qualifiers
REGION                  1..491
                        note = CD5-9L2H-3049 CAR
source                  1..491
                        mol_type = protein
                        organism = synthetic construct
SEQUENCE: 78
MALPVTALLL PLALLLHAAR PGSHIVLTQS PSSLSASLGD RVTISCRASQ DISTYLNWYQ    60
QKPDGTVKLL IFYTSRLHAG VPSRFSGSGS GTHHSLTISN LEQEDIATYF CQQGNSLPFT   120
FGSGTKLEIK GGGGSGGGGS GGGGSQVQLK ESGPELEKPG ASVKISCKAS GYSFTAYSMN   180
WVKQNNGMSL EWIGSIDPYY GDTKYAQKFK GKATLTVDKA SSTAYLQLKS LTSEDSAVYY   240
CARRMITTGD WYFDVWGTGT TVTVSSSGTT TPAPRPPTPA PTIASQPLSL RPEACRPAAG   300
GAVHTRGLDF ACDIYIWAPL AGTCGVLLLS LVITLYCKRG RKKLLYIFKQ PFMRPVQTTQ   360
EEDGCSCRFP EEEEGGCELR VKFSRSADAP AYKQGQNQLY NELNLGRREE YDVLDKRRGR   420
DPEMGGKPRR KNPQEGLYNE LQKDKMAEAY SEIGMKGERR RGKGHDGLYQ GLSTATKDTY   480
DALHMQALPP R                                                       491

SEQ ID NO: 79           moltype = AA  length = 247
FEATURE                 Location/Qualifiers
REGION                  1..247
                        note = CD5-9H2L-3048 scFv
source                  1..247
                        mol_type = protein
                        organism = synthetic construct
SEQUENCE: 79
GSQVQLKESG PELEKPGASV KISCKASGYS FTAYSMNWVK QNNGMSLEWI GSIDPYYGDT    60
KYAQKFKGKA TLTVDKASST AYLQLKSLTS EDSAVYYCAR RMITTGDWYF DVWGTGTTVT   120
VSSGGGGSGG GGSGGGGSHI VLTQSPSSLS ASLGDRVTIS CRASQDISTY LNWYQQKPDG   180
TVKLLIFYTS RLHAGVPSRF SGSGSGTHHS LTISNLEQED IATYFCQQGN SLPFTFGSGT   240
KLEIKSG                                                            247

SEQ ID NO: 80           moltype = AA  length = 243
FEATURE                 Location/Qualifiers
REGION                  1..243
                        note = CD5-9L2H-3049 scFv
source                  1..243
                        mol_type = protein
                        organism = synthetic construct
SEQUENCE: 80
HIVLTQSPSS LSASLGDRVT ISCRASQDIS TYLNWYQQKP DGTVKLLIFY TSRLHAGVPS    60
RFSGSGSGTH HSLTISNLEQ EDIATYFCQQ GNSLPFTFGS GTKLEIKGGG GSGGGGSGGG   120
GSQVQLKESG PELEKPGASV KISCKASGYS FTAYSMNWVK QNNGMSLEWI GSIDPYYGDT   180
KYAQKFKGKA TLTVDKASST AYLQLKSLTS EDSAVYYCAR RMITTGDWYF DVWGTGTTVT   240
VSS                                                                243

SEQ ID NO: 81           moltype = AA  length = 121
FEATURE                 Location/Qualifiers
REGION                  1..121
                        note = CD5-9 VH
source                  1..121
                        mol_type = protein
                        organism = synthetic construct
SEQUENCE: 81
QVQLKESGPE LEKPGASVKI SCKASGYSFT AYSMNWVKQN NGMSLEWIGS IDPYYGDTKY    60
AQKFKGKATL TVDKASSTAY LQLKSLTSED SAVYYCARRM ITTGDWYFDV WGTGTTVTVS   120
S                                                                  121

SEQ ID NO: 82           moltype = AA  length = 107
FEATURE                 Location/Qualifiers
REGION                  1..107
                        note = CD5-9 VL
source                  1..107
                        mol_type = protein
                        organism = synthetic construct
SEQUENCE: 82
HIVLTQSPSS LSASLGDRVT ISCRASQDIS TYLNWYQQKP DGTVKLLIFY TSRLHAGVPS    60
RFSGSGSGTH HSLTISNLEQ EDIATYFCQQ GNSLPFTFGS GTKLEIK                 107

SEQ ID NO: 83           moltype = AA  length = 5
FEATURE                 Location/Qualifiers
REGION                  1..5
                        note = CD5-9 HCDR1
source                  1..5
                        mol_type = protein
                        organism = synthetic construct
SEQUENCE: 83
AYSMN                                                                5
```

```
SEQ ID NO: 84            moltype = AA   length = 17
FEATURE                  Location/Qualifiers
REGION                   1..17
                         note = CD5-9 HCDR2
source                   1..17
                         mol_type = protein
                         organism = synthetic construct
SEQUENCE: 84
SIDPYYGDTK YAQKFKG                                                           17

SEQ ID NO: 85            moltype = AA   length = 12
FEATURE                  Location/Qualifiers
REGION                   1..12
                         note = CD5-9 HCDR3
source                   1..12
                         mol_type = protein
                         organism = synthetic construct
SEQUENCE: 85
RMITTGDWYF DV                                                                12

SEQ ID NO: 86            moltype = AA   length = 11
FEATURE                  Location/Qualifiers
REGION                   1..11
                         note = CD5-9 LCDR1
source                   1..11
                         mol_type = protein
                         organism = synthetic construct
SEQUENCE: 86
RASQDISTYL N                                                                 11

SEQ ID NO: 87            moltype = AA   length = 7
FEATURE                  Location/Qualifiers
REGION                   1..7
                         note = CD5-9 LCDR2
source                   1..7
                         mol_type = protein
                         organism = synthetic construct
SEQUENCE: 87
YTSRLHA                                                                       7

SEQ ID NO: 88            moltype = AA   length = 9
FEATURE                  Location/Qualifiers
REGION                   1..9
                         note = CD5-9 LCDR3
source                   1..9
                         mol_type = protein
                         organism = synthetic construct
SEQUENCE: 88
QQGNSLPFT                                                                     9

SEQ ID NO: 89            moltype = AA   length = 492
FEATURE                  Location/Qualifiers
REGION                   1..492
                         note = CD5-34H2L-3052 CAR
source                   1..492
                         mol_type = protein
                         organism = synthetic construct
SEQUENCE: 89
MALPVTALLL PLALLLHAAR PGSEVKLVES GAELVRSGAS VKLSCAASGF NIKDYYIHWV    60
KQRPEQGLEW IGWIDPENGR TEYAPKFQGK ATMTADTSSN TAYLQLSSLT SEDTAVYYCN   120
NGNYVRHYYF DYWGQGTTVT VSSGGGGSGG GGSGGGGSDW LTQSPAILSA SPGEKVTMTC   180
RAISSVSYMH WYQQKPGSSP KPWIYATSNL ASGVPARFSG SGSGTSYSLT ISRVEAEDAA   240
TYYCQQWSSN PRTFGGGTKL EIKSRTTTPA PRPPTPAPTI ASQPLSLRPE ACRPAAGGAV   300
HTRGLDFACD IYIWAPLAGT CGVLLLSLVI TLYCHMKRGR KKLLYIFKQP FMRPVQTTQE   360
EDGCSCRFPE EEEGGCELTS RVKFSRSADA PAYQQGQNQL YNELNLGRRE EYDVLDKRRG   420
RDPEMGGKPR RKNPQEGLYN ELQKDKMAEA YSEIGMKGER RRGKGHDGLY QGLSTATKDT   480
YDALHMQALP PR                                                       492

SEQ ID NO: 90            moltype = AA   length = 492
FEATURE                  Location/Qualifiers
REGION                   1..492
                         note = CD5-34L2H-3053 CAR
source                   1..492
                         mol_type = protein
                         organism = synthetic construct
SEQUENCE: 90
MALPVTALLL PLALLLHAAR PGSDWLTQSP AILSASPGEK VTMTCRAISS VSYMHWYQQK    60
PGSSPKPWIY ATSNLASGVP ARFSGSGSGT SYSLTISRVE AEDAATYYCQ QWSSNPRTFG   120
```

```
                      -continued
GGTKLEIKGG  GGSGGGGSGG  GGSEVKLVES  GAELVRSGAS  VKLSCAASGF  NIKDYYIHWV  180
KQRPEQGLEW  IGWIDPENGR  TEYAPKFQGK  ATMTADTSSN  TAYLQLSSLT  SEDTAVYYCN  240
NGNYVRHYYF  DYWGQGTTVT  VSSSRTTTPA  PRPPTPAPTI  ASQPLSLRPE  ACRPAAGGAV  300
HTRGLDFACD  IYIWAPLAGT  CGVLLLSLVI  TLYCHMKRGR  KKLLYIFKQP  FMRPVQTTQE  360
EDGCSCRFPE  EEEGGCELTS  RVKFSRSADA  PAYQQGQNQL  YNELNLGRRE  EYDVLDKRRG  420
RDPEMGGKPR  RKNPQEGLYN  ELQKDKMAEA  YSEIGMKGER  RRGKGHDGLY  QGLSTATKDT  480
YDALHMQALP  PR                                                         492

SEQ ID NO: 91           moltype = AA   length = 240
FEATURE                 Location/Qualifiers
REGION                  1..240
                        note = CD5-34H2L-3052 scFv
source                  1..240
                        mol_type = protein
                        organism = synthetic construct
SEQUENCE: 91
EVKLVESGAE  LVRSGASVKL  SCAASGFNIK  DYYIHWVKQR  PEQGLEWIGW  IDPENGRTEY  60
APKFQGKATM  TADTSSNTAY  LQLSSLTSED  TAVYYCNNGN  YVRHYYFDYW  GQGTTVTVSS  120
GGGGSGGGGS  GGGGSDWLTQ  SPAILSASPG  EKVTMTCRAI  SSVSYMHWYQ  QKPGSSPKPW  180
IYATSNLASG  VPARFSGSGS  GTSYSLTISR  VEAEDAATYY  CQQWSSNPRT  FGGGTKLEIK  240

SEQ ID NO: 92           moltype = AA   length = 240
FEATURE                 Location/Qualifiers
REGION                  1..240
                        note = CD5-34L2H-3053 scFv
source                  1..240
                        mol_type = protein
                        organism = synthetic construct
SEQUENCE: 92
DWLTQSPAIL  SASPGEKVTM  TCRAISSVSY  MHWYQQKPGS  SPKPWIYATS  NLASGVPARF  60
SGSGSGTSYS  LTISRVEAED  AATYYCQQWS  SNPRTFGGGT  KLEIKGGGGS  GGGGSGGGGS  120
EVKLVESGAE  LVRSGASVKL  SCAASGFNIK  DYYIHWVKQR  PEQGLEWIGW  IDPENGRTEY  180
APKFQGKATM  TADTSSNTAY  LQLSSLTSED  TAVYYCNNGN  YVRHYYFDYW  GQGTTVTVSS  240

SEQ ID NO: 93           moltype = AA   length = 120
FEATURE                 Location/Qualifiers
REGION                  1..120
                        note = CD5-34 VH
source                  1..120
                        mol_type = protein
                        organism = synthetic construct
SEQUENCE: 93
EVKLVESGAE  LVRSGASVKL  SCAASGFNIK  DYYIHWVKQR  PEQGLEWIGW  IDPENGRTEY  60
APKFQGKATM  TADTSSNTAY  LQLSSLTSED  TAVYYCNNGN  YVRHYYFDYW  GQGTTVTVSS  120

SEQ ID NO: 94           moltype = AA   length = 107
FEATURE                 Location/Qualifiers
REGION                  1..107
                        note = CD5-34 VL
source                  1..107
                        mol_type = protein
                        organism = synthetic construct
SEQUENCE: 94
DWLTQSPAIL  SASPGEKVTM  TCRAISSVSY  MHWYQQKPGS  SPKPWIYATS  NLASGVPARF  60
SGSGSGTSYS  LTISRVEAED  AATYYCQQWS  SNPRTFGGGT  KLEIKSR                107

SEQ ID NO: 95           moltype = AA   length = 5
FEATURE                 Location/Qualifiers
REGION                  1..5
                        note = CD5-34 HCDR1
source                  1..5
                        mol_type = protein
                        organism = synthetic construct
SEQUENCE: 95
DYYIH                                                                  5

SEQ ID NO: 96           moltype = AA   length = 17
FEATURE                 Location/Qualifiers
REGION                  1..17
                        note = CD5-34 HCDR2
source                  1..17
                        mol_type = protein
                        organism = synthetic construct
SEQUENCE: 96
WIDPENGRTE  YAPKFQG                                                    17

SEQ ID NO: 97           moltype = AA   length = 11
FEATURE                 Location/Qualifiers
```

```
REGION                  1..11
                        note = CD5-34 HCDR3
source                  1..11
                        mol_type = protein
                        organism = synthetic construct
SEQUENCE: 97
GNYVRHYYFD Y                                                              11

SEQ ID NO: 98           moltype = AA   length = 10
FEATURE                 Location/Qualifiers
REGION                  1..10
                        note = CD5-34 LCDR1
source                  1..10
                        mol_type = protein
                        organism = synthetic construct
SEQUENCE: 98
RAISSVSYMH                                                                10

SEQ ID NO: 99           moltype = AA   length = 7
FEATURE                 Location/Qualifiers
REGION                  1..7
                        note = CD5-34 LCDR2
source                  1..7
                        mol_type = protein
                        organism = synthetic construct
SEQUENCE: 99
ATSNLAS                                                                    7

SEQ ID NO: 100          moltype = AA   length = 9
FEATURE                 Location/Qualifiers
REGION                  1..9
                        note = CD5-34 LCDR3
source                  1..9
                        mol_type = protein
                        organism = synthetic construct
SEQUENCE: 100
QQWSSNPRT                                                                  9

SEQ ID NO: 101          moltype = AA   length = 9
FEATURE                 Location/Qualifiers
REGION                  1..9
                        note = dextramer
source                  1..9
                        mol_type = protein
                        organism = synthetic construct
SEQUENCE: 101
NLVPMVATV                                                                  9
```

What is claimed is:

1. A chimeric antigen receptor comprising an antigen binding domain comprising a heavy chain variable region comprising the HCDR1, HCDR2, and HCDR3 of SEQ ID NO: 75, and a light chain variable region comprising the LCDR1, LCDR2, and LCDR3 of SEQ ID NO: 76.

2. The chimeric antigen receptor of claim 1, wherein the heavy chain variable region comprises an amino acid sequence having at least 90% identity to the amino acid sequence of SEQ ID NO: 75, and the light chain variable region comprises an amino acid sequence having at least 90% identity to the amino acid sequence of SEQ ID NO: 76.

3. A pharmaceutical composition comprising a population of T-cells comprising the chimeric antigen receptor of claim 2.

4. The chimeric antigen receptor of claim 1, wherein the heavy chain variable region comprises an amino acid sequence having at least 95% identity to the amino acid sequence of SEQ ID NO: 75 and the light chain variable region comprises an amino acid sequence having at least 95% identity to the amino acid sequence of SEQ ID NO: 76.

5. A pharmaceutical composition comprising a population of T-cells comprising the chimeric antigen receptor of claim 3.

6. A method of treating T cell lymphoma in a subject in need thereof, the method comprising administering to the subject the pharmaceutical composition of claim 5.

7. The chimeric antigen receptor of claim 1, wherein the heavy chain variable region comprises the amino acid sequence of SEQ ID NO: 75 and the light chain variable region comprises the amino acid sequence of SEQ ID NO: 76.

8. A pharmaceutical composition comprising a population of T-cells comprising the chimeric antigen receptor of claim 4.

9. A method of treating T cell lymphoma in a subject in need thereof, the method comprising administering to the subject the pharmaceutical composition of claim 8.

10. The chimeric antigen receptor of claim 1, wherein the antigen binding domain comprises a single chain variable fragment (scFv) comprising an amino acid sequence having at least 90% identity to the amino acid sequence of SEQ ID NO: 74.

11. A pharmaceutical composition comprising a population of T-cells comprising the chimeric antigen receptor of claim 10.

12. A method of treating T cell lymphoma in a subject in need thereof, the method comprising administering to the subject the pharmaceutical composition of claim 11.

13. The chimeric antigen receptor of claim 1, wherein the antigen binding domain comprises an scFv comprising the amino acid of SEQ ID NO: 74.

14. A pharmaceutical composition comprising a population of T-cells comprising the chimeric antigen receptor of claim 13.

15. A method of treating T cell lymphoma in a subject in need thereof, the method comprising administering to the subject the pharmaceutical composition of claim 14.

16. The chimeric antigen receptor of claim 1, wherein the antigen binding domain comprises an scFv comprising the amino acid of SEQ ID NO: 73.

17. The chimeric antigen receptor of claim 1, wherein the chimeric antigen receptor comprises an amino acid sequence having at least 90% identity to the amino acid sequence of SEQ ID NO: 72.

18. A pharmaceutical composition comprising a population of T-cells comprising the chimeric antigen receptor of claim 17.

19. A method of treating T cell lymphoma in a subject in need thereof, the method comprising administering to the subject the pharmaceutical composition of claim 18.

20. The chimeric antigen receptor of claim 1, wherein the chimeric antigen receptor comprises the amino acid of SEQ ID NO: 72.

21. A pharmaceutical composition comprising a population of T-cells comprising the chimeric antigen receptor of claim 1.

22. A method of treating T cell lymphoma in a subject in need thereof, the method comprising administering to the subject the pharmaceutical composition of claim 21.

\* \* \* \* \*